United States Patent
Ishibashi et al.

(10) Patent No.: US 12,400,758 B2
(45) Date of Patent: Aug. 26, 2025

(54) INFORMATION PROCESSING DEVICE AND INFORMATION PROCESSING METHOD

(71) Applicant: PARAMOUNT BED CO., LTD., Tokyo (JP)

(72) Inventors: Yoshinori Ishibashi, Tokyo (JP); Takashi Ishikawa, Tokyo (JP)

(73) Assignee: PARAMOUNT BED CO., LTD., Tokyo (JP)

( * ) Notice: Subject to any disclaimer, the term of this patent is extended or adjusted under 35 U.S.C. 154(b) by 166 days.

(21) Appl. No.: 18/021,722

(22) PCT Filed: Jun. 29, 2021

(86) PCT No.: PCT/JP2021/024601
§ 371 (c)(1),
(2) Date: Feb. 16, 2023

(87) PCT Pub. No.: WO2022/185558
PCT Pub. Date: Sep. 9, 2022

(65) Prior Publication Data
US 2023/0317273 A1  Oct. 5, 2023

(30) Foreign Application Priority Data
Mar. 1, 2021  (JP) .................. 2021-032143

(51) Int. Cl.
*G16H 40/67* (2018.01)
*A61B 5/00* (2006.01)
(Continued)

(52) U.S. Cl.
CPC .......... *G16H 40/67* (2018.01); *A61B 5/4088* (2013.01); *G16H 20/70* (2018.01); *G16H 40/20* (2018.01)

(58) Field of Classification Search
None
See application file for complete search history.

(56) References Cited

U.S. PATENT DOCUMENTS

| | | | |
|---|---|---|---|
| 2014/0347491 A1* | 11/2014 | Connor | A61B 5/1114 348/158 |
| 2016/0095758 A1* | 4/2016 | Haire | A61B 5/002 600/595 |

(Continued)

FOREIGN PATENT DOCUMENTS

| | | |
|---|---|---|
| JP | 2007-233471 A | 9/2007 |
| JP | 2017-37385 A | 2/2017 |

(Continued)

OTHER PUBLICATIONS

Mathkunti et al. ("Machine learning techniques to identify dementia." SN Computer Science 1.3 (2020): 118.) (Year: 2020).*

*Primary Examiner* — Christopher B Tokarczyk
(74) *Attorney, Agent, or Firm* — BIRCH, STEWART, KOLASCH & BIRCH, LLP

(57) ABSTRACT

The information processing device includes a factor determination unit configured to determine whether the behavior of an assisted person is an abnormal behavior of a dementia factor based on (1) information on a dementia level of the assisted person and (2) at least one of an environmental information, an excretion information, and a sleep information of the assisted person, and a support information output unit configured to output the support information to support an assistance of the assisted person by a caregiver based on the determination result of the factor determination unit and sensor information that is a sensing result about the assisted person or the caregiver assisting the assisted person.

15 Claims, 39 Drawing Sheets

(51) Int. Cl.
    *G16H 20/70*         (2018.01)
    *G16H 40/20*         (2018.01)

(56) References Cited

U.S. PATENT DOCUMENTS

2016/0314255 A1* 10/2016 Cook .................... G06F 16/906
2020/0135319 A1* 4/2020 Vleugels .............. A61B 5/7267

FOREIGN PATENT DOCUMENTS

| JP | 2019-170408 A | 10/2019 |
| KR | 10-1880500 B1 | 8/2018 |
| KR | 10-2202262 B1 | 1/2021 |

* cited by examiner

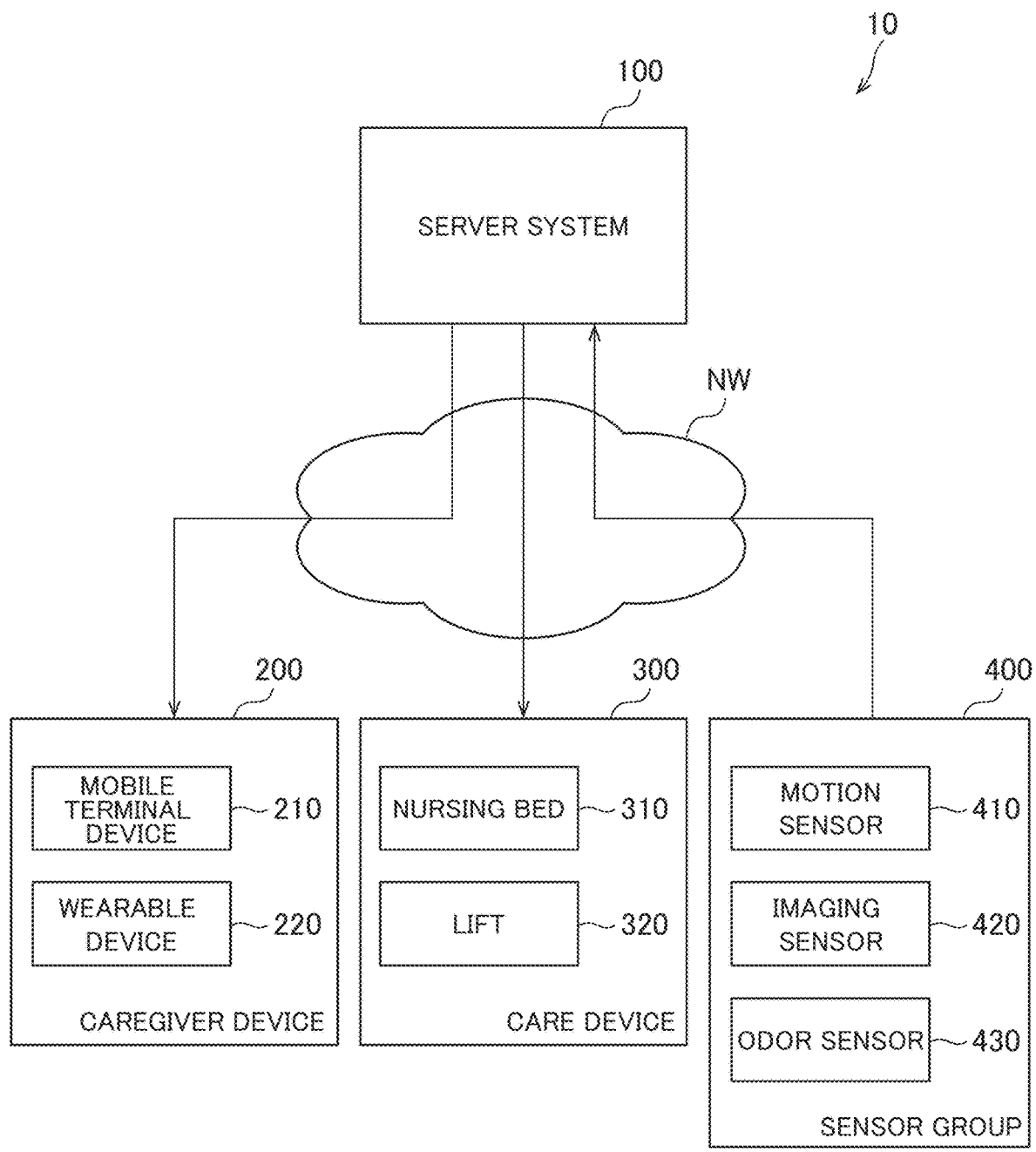

FIG. 11
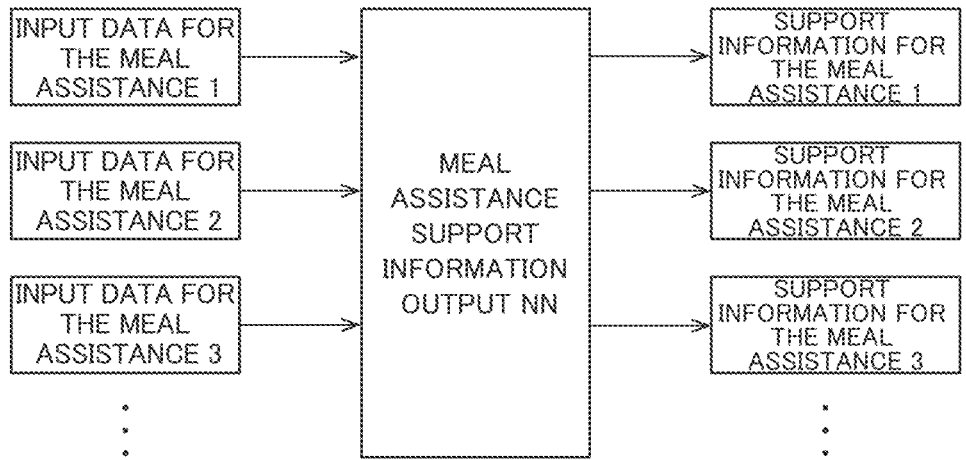
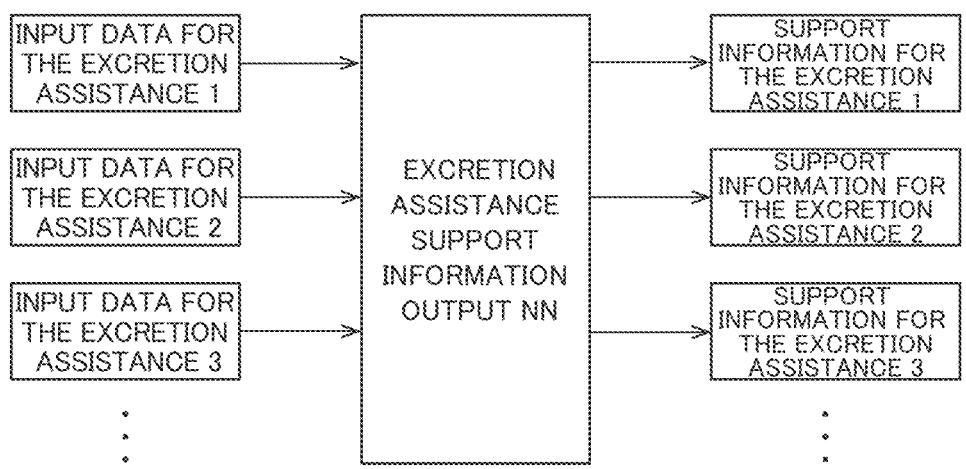
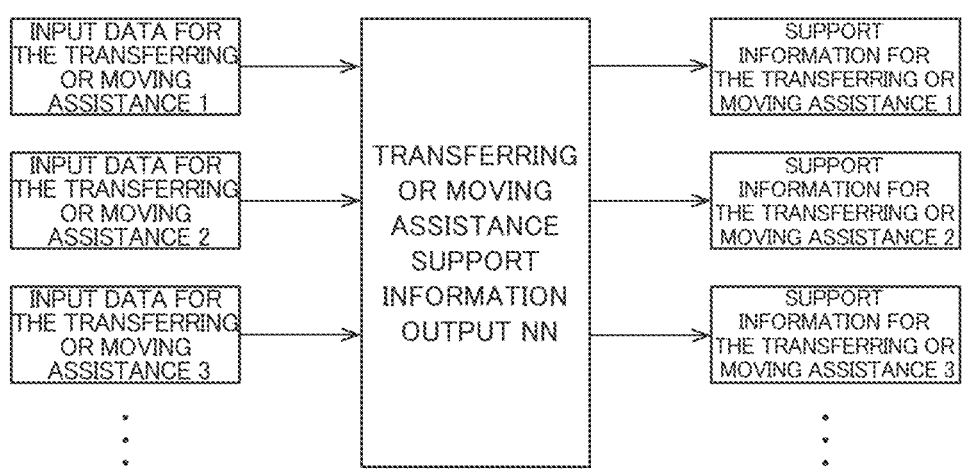

FIG. 14

FIRST ASSOCIATION INFORMATION

| CAREGIVER ID | SUPPORT INFORMATION | OUTPUT SETTING |
|---|---|---|
| abcde | A TIMING OF CHANGING THE DIAPER | ACTIVE |
| abcde | AN AMOUNT OF SERVING WITH A SPOON | CAN'T OUTPUT |
| abcde | A TIMING OF SERVING THE MEAL WITH THE SPOON | INACTIVE |
| fghij | A TIMING OF CHANGING THE DIAPER | INACTIVE |
| ⋮ | ⋮ | ⋮ |

FIG. 15

SECOND ASSOCIATION INFORMATION

| SUPPORT INFORMATION | REQUIRED INPUT DATA GROUP |
|---|---|
| A TIMING OF CHANGING THE DIAPER | MEAL QUANTITY, WATER QUANTITY, A TIME OF THE MEAL, ODOR INFORMATION, SLEEP INFORMATION,⋯ |
| AN AMOUNT OF SERVING WITH A SPOON | TEMPERATURE, WEIGHT, PATIENT'S FACE,⋯ |
| ⋮ | ⋮ |

FIG. 16

THIRD ASSOCIATION INFORMATION

| NURSING HOME ID | OBTAINABLE INPUT DATA GROUP |
|---|---|
| NURSING HOME 1 | AN AMOUNT OF THE MEAL, A WATER AMOUNT, A TIMING OF THE MEAL, ODOR INFORMATION, SLEEP INFORMATION ⋯ |
| NURSING HOME 2 | AN AMOUNT OF THE MEAL, A WATER AMOUNT, HEIGHT, WEIGHT,⋯ |
| ⋮ | ⋮ |

FIG. 28

| NUMBER | DATA ELEMENTS |
|---|---|
| 1 | BED DATA |
| 2 | CONNECTION STATUS |
| 3 | CONNECTION PROTOCOL |
| 4 | LAST KNOWN BED CONNECTION |
| 5 | BED POSITION (HEIGHT) |
| 6 | HEADBOARD POSITION |
| 7 | FOOTBOARD POSITION |
| 8 | HEAD ANGLE |
| 9 | BED POSITION (BACK) |
| 10 | BED POSITION (KNEES) |
| 11 | BED POSITION (LEG) |
| 12 | BED POSITION (TILT) |
| 13 | BACK ANGLE ALARM MODE |
| 14 | BACK ANGLE ALARM AUDIBLE MODE |
| 15 | BACK ANGLE ALARM STATUS |
| 16 | NURSE CALL INDICATOR STATUS |
| 17 | NURSE ANSWER INDICATOR STATUS |
| 18 | BED WASHED/CLEANED STATUS |
| 19 | SERVER INDICATOR STATUS WHEN BED IS AN ONLINE STATUS |
| 20 | BACK ANGLE MOTOR LOCKOUT STATUS |
| 21 | KNEE ANGLE MOTOR LOCKOUT STATUS |
| 22 | LEG ANGLE MOTOR LOCKOUT STATUS |
| 23 | BED HEIGHT MOTOR LOCKOUT STATUS |
| 24 | TILTED ANGLE MOTOR LOCKOUT STATUS |
| 25 | ALL MOTOR LOCKOUT STATUS |
| 26 | BED MODEL NAME |
| 27 | PATIENT ENVIRONMENT FINAL COMMAND |
| 28 | PATIENT HISTORY LAST COMMAND |
| 29 | AC POWER STATUS |
| 30 | BATTERY POWER STATUS |
| 31 | PATIENT POSITIONING ALARM MODE |
| 32 | PATIENT POSITIONING ALARM STATUS |
| 33 | THE MAGNITUDE OF A PATIENT'S MOVEMENT |
| 34 | PATIENT MOVING DIRECTION |
| 35 | SAFETY DISPLAY MODE |
| 36 | SAFE DISPLAY MODE STATUS |
| 37 | SCALE LAST COMMAND |
| 38 | PATIENT MEASURED WEIGHT KG |
| 39 | PATIENT MEASURED WEIGHT LBS |
| 40 | PATIENT WEIGHT RAW VALUE KG |
| 41 | PATIENT WEIGHT RAW VALUE LBS |
| 42 | REQUIRED SERVICE STATUS |
| 43 | NURSE CALL SWITCH STATUS |
| 44 | CPR SWITCH STATUS |
| 45 | BED CLEANED SWITCH STATUS |
| 46 | ROTATION STATUS |
| 47 | PERCUSSION THERAPY STATUS |
| 48 | VIBRATION THERAPY STATUS |
| 49 | BRAKE SWITCH STATUS |
| 50 | BED SERVICE CODE |

FIG. 29

| NUMBER | DATA ELEMENTS |
|---|---|
| 51 | FRAME SERIAL NUMBER |
| 52 | DETECTED PATIENTS |
| 53 | SIDE RAIL SAFETY INDICATION |
| 54 | SAFETY INDICATION PATIENT POSITION |
| 55 | HEAD ANGLE LIMIT EFFECTIVE |
| 56 | PATIENT POSITION CHAIR MODE |
| 57 | SAFE LABEL INCONTINENCE |
| 58 | DISCOVER INCONTINENCE |
| 59 | DETECTED DETERIORATION STATUS |
| 60 | MAC ADDRESS |
| 61 | IP ADDRESS |
| 62 | SIGNAL STRENGTH IN DBM |
| 63 | LOAD CELL DATA |
| 64 | LOG FILE |
| 65 | VITAL (EWS INPUT) |
| 66 | RESPIRATORY RATE |
| 67 | HEART RATE |
| 68 | PULSE RATE |
| 69 | SPO2/SAO2 |
| 70 | BLOOD PRESSURE |
| 71 | TEMPERATURE |
| 72 | HUMIDITY |
| 73 | ILLUMINANCE |
| 74 | VITAL TENDENCY |
| 75 | PAIN SCORE |
| 76 | URINE OUTPUT |
| 77 | RESEARCH |
| 78 | POC BLOOD GLUCOSE |
| 79 | BASIC METABOLISM PANEL (BMP) |
| 80 | BLOOD GLUCOSE LEVEL |
| 81 | URINALYSIS (PANEL) |
| 82 | PH |
| 83 | A SUSPECTED OR PRESENT INFECTION |
| 84 | INTERVENTION |
| 85 | PATIENT'S STATUS |
| 86 | ALLERGY |
| 87 | CAUTIONS (ISOLATION, VIOLENCE, ELOPEMENT, PSYCHOLOGICAL) |
| 88 | DIETARY STATUS |
| 89 | WALKING (NORMAL/BEDRIDDEN/IMMOBILE/WEAK/NOT STABLE/IMPAIRED) |
| 90 | VISUAL IMPAIRMENT AFFECTING DAILY FUNCTIONING |
| 91 | DIZZINESS, ORTHOSTATIC HYPOTENSION, WEAKNESS |
| 92 | MOVING FROM BED TO CHAIR (CAN'T/NEEDS MUCH ASSISTANCE/IS HARD TO HANDLE/IS INDEPENDENT) |
| 93 | GETTING UP FROM A SITTING POSITION (IN A SINGLE MOTION/PUSHING UP) IN A SINGLE ATTEMPT/SUCCESSFUL AFTER MULTIPLE ATTEMPTS/SEEKING SUPPORT) |
| 94 | MOBILITY ABILITY (IMMOBILE, WHEELCHAIR, INDEPENDENT OR ASSISTANT/INDEPENDENT PERSON WITH WALKING ASSISTANCE) |
| 95 | INCONTINENCE |
| 96 | URGENCY AND FREQUENCY OF URINATION |
| 97 | URETHRAL CATHETER/OSTOMY |
| 98 | A CALMED PROCEDURE |
| 99 | MENTAL STATE (EMPHASIS ON YOUR OWN ABILITIES/FORGETTING YOUR LIMITS/ENOUGH VIGILANCE/FEELING IRRITATED OR ANXIOUS/INTERMITTENT CONFUSION, CONFUSION, STUPEFACTION) |
| 100 | COGNITION (RECOGNITION OF PHYSICAL ENVIRONMENTAL CHANGE, COMPULSIVE/FORGETTING THE RESTRICTIVE) |

FIG. 30

| NUMBER | DATA ELEMENTS |
|---|---|
| 101 | ACTION (PLAYING OR APPROPRIATE/SLEEPING/INACTIVE/LETHARGIC OR CONFUSED OR HAVING A DECREASED PAIN RESPONSE) |
| 102 | DEMOGRAPHIC STATISTICS |
| 103 | CURRENT AGE (OBSERVABLE ENTITY) |
| 104 | AGE (VALUE OF QUALIFIER) |
| 105 | AGING (FOUND) |
| 106 | PREMATURE AGING (DETECTION) |
| 107 | OLD AGE (FOUND) |
| 108 | OLD AGE SENILE WEAKNESS (FOUND) |
| 109 | SENILITY (FOUND) |
| 110 | EXTREME OLD AGE (MORE THAN 100 YEARS) (FOUND) |
| 111 | GERIATRIC FATIGUE (FOUND) |
| 112 | SENILE APATHY (FOUND) |
| 113 | OLD AGE (MODIFIER VALUES) |
| 114 | A WHOLE LIFE |
| 115 | OLD AGE (FOUND) |
| 116 | SENILE WEAKNESS (FOUND) |
| 117 | SENILITY (FOUND) |
| 118 | AGE OVER 100 |
| 119 | GERIATRIC FATIGUE (FOUND) |
| 120 | SENILE APATHY (FOUND) |
| 121 | GENDER (OBSERVABLE ENTITY) |
| 122 | PHARMACEUTICALS |
| 123 | MEDICINES YOU ARE CURRENTLY TAKING |
| 124 | ANALGESICS (SUBSTANCES) |
| 125 | MEDICINES (PRODUCTS) THAT ACT AS PAIN RELIEVERS |
| 126 | ANTIARRHYTHMIC MEDICINE (SUBSTANCES) |
| 127 | MEDICINES ACTING AS ANTIARRHYTHMIC AGENTS (PRODUCTS) |
| 128 | VASODILATORS (SUBSTANCES) |
| 129 | ANTIHYPERTENSIVE (SUBSTANCE) |
| 130 | ANTIHYPERTENSIVE MEDICINES (PRODUCTS) |
| 131 | ANTIPSYCHOTICS (SUBSTANCES) |
| 132 | MEDICINES (PRODUCTS) THAT ACT AS ANTIPSYCHOTICS |
| 133 | DIURETICS (SUBSTANCES) |
| 134 | DIURETIC MEDICINES (PRODUCTS) |
| 135 | CYCLIC DIURETICS (SUBSTANCES) |
| 136 | CYCLIC DIURETIC OVERDOSE (DISORDER) |
| 137 | A PSYCHOACTIVE SUBSTANCE (SUBSTANCE) |
| 138 | ANTIDEPRESSANTS (SUBSTANCES) |
| 139 | MEDICINES ACTING AS ANTIDEPRESSANTS (PRODUCTS) |
| 140 | ANTIPSYCHOTICS (SUBSTANCES) |
| 141 | MEDICINES (PRODUCTS) THAT ACT AS ANTIPSYCHOTICS |
| 142 | A PSYCHOACTIVE SUBSTANCE (SUBSTANCE) |
| 143 | PSYCHOTROPICS (SUBSTANCES) |
| 144 | DOSE OF THE MEDICINES |
| 145 | WHEN THE MEDICINES EXPIRES |
| 146 | WHEN WAS THE LAST TIME YOU RECEIVED YOUR MEDICINES? |
| 147 | MEDICATION ROUTE |
| 148 | MEDICINES FORM (LIQUIDS, TABLETS, ETC.) |
| 149 | ANEMIA (DISORDER) |
| 150 | HEART CARDIAC ARRHYTHMIA (DISORDER) |

FIG. 31

| NUMBER | DATA ELEMENTS |
|---|---|
| 151 | CARDIOMYOPATHY (DISORDER) |
| 152 | DEHYDRATION (DISORDER) |
| 153 | MILD DEHYDRATION (DISORDER) |
| 154 | MODERATE DEHYDRATION (DISORDER) |
| 155 | DEHYDRATION AFTER EXERTION (DISORDER) |
| 156 | SEVERE DEHYDRATION (DISORDER) |
| 157 | SODIREMIC DEHYDRATION (DISORDER) |
| 158 | PNEUMONIA (DISORDER) |
| 159 | ASPIRATION PNEUMONIA (DISORDER) |
| 160 | VIRAL SEPSIS (DISORDER) |
| 161 | SEPSIS (DISORDER) DUE TO URINARY TRACT INFECTION |
| 162 | SEPSIS (DISORDER) DUE TO ORAL INFECTION |
| 163 | SEPSIS (DISORDER) WITH SKIN SYMPTOMS |
| 164 | SEPSIS (DISORDER) CAUSED BY FUNGI |
| 165 | ANEMIA (DISORDER) |
| 166 | DIABETES (DISORDER) |
| 167 | HYPOGLYCEMIA (DISORDER) |
| 168 | ORTHOSTATIC HYPOTENSION (DISORDER) |
| 169 | POSTURAL HYPOTENSION AFTER EXERCISE (DISORDER) |
| 170 | CONCURRENT ORTHOSTATIC HYPOTENSION ASSOCIATED WITH PARKINSON'S DISEASE AND ITS CAUSES (DISORDER) |
| 171 | POSTURAL ORTHOSTATIC TACHYCARDIA SYNDROME (DISORDER) |
| 172 | SYMPATHETIC ORTHOSTATIC HYPOTENSION (DISORDER) |
| 173 | CHRONIC ORTHOSTATIC HYPOTENSION (DISORDER) |
| 174 | DELIRIUM (DISORDER) |
| 175 | DELIRIUM (DISORDER) ASSOCIATED WITH DEMENTIA |
| 176 | DELIRIUM DUE TO MULTIPLE CAUSES (DISORDERS) |
| 177 | DELIRIUM (DISORDER) CAUSED BY SUBSTANCES OR DRUGS |
| 178 | DELIRIUM IN REMISSION (DISORDER) |
| 179 | A STATE OF CHRONIC CONFUSION (DISORDER) |
| 180 | ACUTE CONFUSION, POST-TRAUMATIC (DISORDER) |
| 181 | DEMENTIA (DISORDER) |
| 182 | PRIMARY DEGENERATIVE DEMENTIA (DISORDER) |
| 183 | DEMENTIA WITH BEHAVIORAL DISORDERS (DISORDER) |
| 184 | DELIRIUM (DISORDER) ASSOCIATED WITH DEMENTIA |
| 185 | RAPIDLY PROGRESSIVE DEMENTIA (DISORDER) |
| 186 | SYSTEMIC PARALYSIS MONONEUROSYPHILIS (DISORDER) |
| 187 | ALZHEIMER'S DISEASE (DISORDER) |
| 188 | SENILE DEMENTIA (DISORDER) |
| 189 | SENILE DEMENTIA (DISORDER) |
| 190 | DIALYSIS DEMENTIA (DISORDER) |
| 191 | SYSTEMIC ARTHRITIS (DISORDER) |
| 192 | RHEUMATOID ARTHRITIS (DISORDER) |
| 193 | FOOT DEFORMITY (DISORDER) |
| 194 | BUNIONS OF THE LEFT FOOT (DISORDER) |
| 195 | HALLUX VALGUS OF RIGHT FOOT (DISORDER) |
| 196 | FOOT DEFORMITY DUE TO RHEUMATOID ARTHRITIS (FOUND) |
| 197 | PUTTER FEET (FOUND) |
| 198 | FOOT PRONATION DEFORMITY (FOUND) |
| 199 | UPWARD DEFORMITY OF THE FOOT (FOUND) |
| 200 | PROTRUDED FOREFOOT (FOUND) |

FIG. 32

| NUMBER | DATA ELEMENTS |
|---|---|
| 201 | FOREFOOT UP (FOUND) |
| 202 | HALLUX VALGUS (FOUND) |
| 203 | PLANTAR FLEXION DEFORMITY (FOUND) |
| 204 | FOOT ABDUCTION DEFORMITY (FOUND) |
| 205 | ACQUIRED INGROWN NAILS (DISORDER) |
| 206 | DORSIFLEXION DEFORMITY OF FOOT (FOUND) |
| 207 | ACQUIRED VALGUS HEEL (DISORDER) |
| 208 | OVERRIDING FIFTH TOE (DISORDER) |
| 209 | OVERRIDING TOE (DISORDER) |
| 210 | MUSCLE WEAKNESS (FOUND) |
| 211 | MUSCLE WEAKNESS IN THE HANDS AND FEET (FOUND) |
| 212 | SPASTIC PARALYSIS (FOUND) |
| 213 | HAND MUSCLE WEAKNESS (FOUND) |
| 214 | WEAKNESS OF JAW MUSCLES (FOUND) |
| 215 | PRESENCE (FOUND) OF WEAKNESSES |
| 216 | SUBJECTIVE MUSCLE WEAKNESS (FOUND) |
| 217 | PARALYSIS OF LOWER LIMBS (FOUND) |
| 218 | WEAKENING OF FACIAL MUSCLES (FOUND) |
| 219 | PARKINSON'S DISEASE (DISORDER) |
| 220 | HEARING LOSS, DIVERTICULOSIS OF THE SMALL INTESTINE, NEUROPATHIC SYNDROME (DISORDER) |
| 221 | DEAFNESS (DISORDER) |
| 222 | MILD TO MODERATE HEARING LOSS (DISORDER) |
| 223 | SEVERE HEARING LOSS (DISORDER) |
| 224 | HEARING LOSS (DISORDER) IN THE LEFT EAR |
| 225 | HEARING LOSS (DISORDER) IN THE RIGHT EAR |
| 226 | COMBINED VISUAL AND HEARING IMPAIRMENT (DISORDER) |
| 227 | ASYMMETRIC HEARING LOSS (DISORDER) |
| 228 | PARTIAL HEARING LOSS (DISORDER) |
| 229 | DURING EXAM – DEAF HANDICAPPED (DISORDER) |
| 230 | SYMPTOMS OF HEARING LOSS (DISORDER) |
| 231 | CHRONIC HEARING LOSS (DISORDER) |
| 232 | CATARACT (DISORDER) |
| 233 | GLAUCOMA (DISORDER) |
| 234 | AGE-RELATED MACULAR DEGENERATION (DISORDER) |
| 235 | MUSCLE WEAKNESS (FOUND) |
| 236 | MUSCLE WEAKNESS IN THE HANDS AND FEET (FOUND) |
| 237 | SPASTIC PARALYSIS (FOUND) |
| 238 | HAND MUSCLE WEAKNESS (FOUND) |
| 239 | SUBJECTIVE MUSCLE WEAKNESS (FOUND) |
| 240 | PARALYSIS OF LOWER LIMBS (FOUND) |
| 241 | WEAKENING OF FACIAL MUSCLES (FOUND) |
| 242 | ABNORMAL GAIT DUE TO IMPAIRED BALANCE (FOUND) |
| 243 | DISEQUILIBRIUM (FOUND) |
| 244 | DIFFICULT TO BALANCE (FOUND) |
| 245 | CAN'T BALANCE (FOUND) |
| 246 | UNBALANCED (FOUND) |
| 247 | GENERAL INSTABILITY (FOUND) |
| 248 | BALANCE DISORDER, VESTIBULAR NERVE (DISORDER) |
| 249 | UNSTABLE WHEN TURNING (FOUND) |
| 250 | UNSTEADY WHEN STANDING (FOUND) |

FIG. 33

| NUMBER | DATA ELEMENTS |
|---|---|
| 251 | BAD BALANCE (FOUND) |
| 252 | KEEP LOSING BALANCE (FOUND) |
| 253 | I FEEL LIKE I'M GOING TO FALL (FOUND) |
| 254 | LOSS OF EQUILIBRIUM (FOUND) |
| 255 | VISUAL IMPAIRMENT (DISORDER) |
| 256 | COMBINED VISUAL AND HEARING IMPAIRMENT (DISORDER) |
| 257 | MULTIPLE IMPAIRMENT VISUAL IMPAIRMENT (DISORDER) |
| 258 | MILD VISUAL IMPAIRMENT (DISORDER) |
| 259 | MODERATE VISUAL IMPAIRMENT (DISORDER) |
| 260 | SEVERE VISUAL IMPAIRMENT (DISORDER) |
| 261 | ORTHOSTATIC HYPOTENSION (DISORDER) |
| 262 | POSTURAL HYPOTENSION AFTER EXERCISE (DISORDER) |
| 263 | ARTHRITIS (DISORDER) |
| 264 | RHEUMATOID ARTHRITIS (DISORDER) |
| 265 | URINARY INCONTINENCE (FOUND) |
| 266 | URINARY INCONTINENCE DUE TO BENIGN PROSTATIC HYPERPLASIA (FOUND) |
| 267 | CONCURRENT URINARY INCONTINENCE DUE TO FEMALE GENITAL PROLAPSE (DISORDER) |
| 268 | INTERMITTENT INCONTINENCE (FOUND) |
| 269 | URINARY INCONTINENCE DUE TO URETHRAL SPHINCTER FAILURE (FOUND) |
| 270 | TOTAL INCONTINENCE (FOUND) |
| 271 | DOUBLE INCONTINENCE (FOUND) |
| 272 | NON-ORGANIC INCONTINENCE (FOUND) |
| 273 | PARKINSON'S DISEASE (DISORDER) |
| 274 | DEMENTIA (DISORDER) |
| 275 | PRIMARY DEGENERATIVE DEMENTIA (DISORDER) |
| 276 | DEMENTIA WITH BEHAVIORAL DISORDERS (DISORDER) |
| 277 | DELIRIUM (DISORDER) ASSOCIATED WITH DEMENTIA |
| 278 | RAPIDLY PROGRESSIVE DEMENTIA (DISORDER) |
| 279 | TOXIN-INDUCED DEMENTIA (DISORDER) |
| 280 | DEMENTIA (DISORDER) ASSOCIATED WITH OTHER DISEASES |
| 281 | DRUG-INDUCED DEMENTIA (DISORDER) |
| 282 | ALZHEIMER'S DISEASE (DISORDER) |
| 283 | SENILE DEMENTIA (DISORDER) |
| 284 | SENILE DEMENTIA (DISORDER) |
| 285 | DIALYSIS DEMENTIA (DISORDER) |
| 286 | COGNITIVE IMPAIRMENT (FOUND) |
| 287 | COGNITIVE DEFICITS IN ATTENTION (FOUND) |
| 288 | DEPRESSED MOOD (DISORDER) IN ALZHEIMER'S DISEASE |
| 289 | DELUSIONS (DISORDERS) IN ALZHEIMER'S DISEASE |
| 290 | SEVERE COGNITIVE IMPAIRMENT (FOUND) |
| 291 | MODERATE COGNITIVE IMPAIRMENT (FOUND) |
| 292 | IMPAIRED MEMORY (FOUND) |
| 293 | ENVIRONMENTAL INTERPRETATION DISORDER SYNDROME (FOUND) |
| 294 | DISTURBANCES IN COGNITIVE LEARNING (FOUND) |
| 295 | LACK OF THINKING ABILITY (FOUND) |
| 296 | MINIMAL COGNITIVE IMPAIRMENT (FOUND) |
| 297 | AGE-RELATED COGNITIVE DECLINE (FOUND) |
| 298 | DIABETES (DISORDER) |
| 299 | MULTIPLE DRUGS COMBINATION THERAPY (FOUND) |
| 300 | ANALGESICS (SUBSTANCES) |

FIG. 34

| NUMBER | DATA ELEMENTS |
|---|---|
| 301 | ANTIARRHYTHMIC AGENTS (SUBSTANCES) |
| 302 | VASODILATORS (SUBSTANCES) |
| 303 | ANTIHYPERTENSIVE (SUBSTANCE) |
| 304 | ANTIHYPERTENSIVE DRUGS (PRODUCTS) |
| 305 | ANTIPSYCHOTICS (SUBSTANCES) |
| 306 | DRUGS (PRODUCTS) THAT ACT AS ANTIPSYCHOTICS |
| 307 | DIURETICS (SUBSTANCES) |
| 308 | ANTIDEPRESSANTS (SUBSTANCES) |
| 309 | HISTORY OF FALLINGS |
| 310 | FALLING (EVENT) |
| 311 | FALLING INTO THE WATER (EVENT) |
| 312 | FALLING (AN EVENT) TO A SOFT SURFACE |
| 313 | FALLING ON A HARD SURFACE (EVENT) |
| 314 | JUMP FROM COMBUSTION STRUCTURE (EVENT) |
| 315 | FALLING ACCIDENT (EVENT) |
| 316 | FALLING/FALLING/FALLING/FALLING (EVENT) ON A TRAIN |
| 317 | INVOLVED IN FALLING (EVENT) |
| 318 | FALLING ON THE SNOW (EVENT) |
| 319 | FALLING (FOUND) |
| 320 | FALLING CAUSED BY DRUGS (FOUND) |
| 321 | FALLING IN THE ELDERLY (FOUND) |
| 322 | RISK OF FALLING (FOUND) |
| 323 | HIGH RISK OF FALLING (FOUND) |
| 324 | MODERATE RISK OF FALLING (FOUND) |
| 325 | LOW RISK OF FALLING (FOUND) |
| 326 | WALKING ABILITY (OBSERVABLE ENTITIES) |
| 327 | ABLE TO WALK ON UNEVEN SURFACES (OBSERVABLE ENTITIES) |
| 328 | THE ABILITY TO WALK BACKWARDS WHILE PULLING A LARGE TOY (AN OBSERVABLE ENTITY) |
| 329 | YOU CAN WALK WITH A LARGE TOY (OBSERVABLE ENTITY) |
| 330 | ABILITY TO WALK FROM HEEL TO TOE (OBSERVABLE ENTITY) |
| 331 | THE ABILITY TO WALK A FINE LINE (AN OBSERVABLE ENTITY) |
| 332 | THE ABILITY TO VOLUNTARILY START OR STOP WALKING (AN OBSERVABLE ENTITY) |
| 333 | ABILITY TO STOP WALKING (OBSERVABLE ENTITY) |
| 334 | ABILITY TO INITIATE WALKING (OBSERVABLE ENTITY) |
| 335 | CAN GO DOWN A SLOPE (OBSERVABLE ENTITY) |
| 336 | ABLE TO CLIMB A SLOP (OBSERVABLE ENTITIES) |
| 337 | CAPABLE OF DESCENDING A SLOPE (OBSERVABLE ENTITY) |
| 338 | CAPABLE OF CLIMBING A SLOPE (OBSERVABLE ENTITY) |
| 339 | ABLE TO WALK ON FLAT LAND (OBSERVABLE ENTITIES) |
| 340 | SEARCHING (FOUND) HOW TO USE WALKING AIDS |
| 341 | USING (FOUND) TWO CANES |
| 342 | USE TWO CRUTCHES FOR WALKING (FOUND) |
| 343 | USE ONE CRUTCH FOR WALKING (FOUND) |
| 344 | USING A SINGLE CANE (FOUND) |
| 345 | USE ZIMMERFRAMES, USE ZIMMERFRAMES (FOUND) |
| 346 | TRIPOD, QUADRUPED: WALKING (FOUND) |
| 347 | A STICK USED ONLY FOR WALKING (FOUND) |
| 348 | NO WALKING AID (FOUND) |
| 349 | DEPENDENCE ON A CANE (FOUND) |
| 350 | CANE, DEVICE (PHYSICAL OBJECT) |

FIG. 35

| NUMBER | DATA ELEMENTS |
|---|---|
| 351 | A LONG CANE (A PHYSICAL OBJECT) |
| 352 | WHEELCHAIR CRUTCH/WALKING STICK HOLDER (PHYSICAL OBJECT) |
| 353 | WALKING |
| 354 | NORMAL GAIT (FOUND) |
| 355 | WALKING NORMALLY AT THE TIME OF EXAMINATION (FOUND) |
| 356 | MENTAL STATE |
| 357 | ENVIRONMENTAL INTERPRETATION DISORDER SYNDROME (FOUND) |
| 358 | SPATIAL DISORIENTATION (FOUND) |
| 359 | LOCATION CONFUSION (FOUND) |
| 360 | CONFUSED SELF-AWARENESS (FOUND) |
| 361 | A PERSON'S DISORIENTATION (FOUND) |
| 362 | MISDIRECTION OF PEOPLE, TIME AND PLACE (FOUND) |
| 363 | TIME CONFUSED (FOUND) |
| 364 | RIGHT AND LEFT MISGUIDED (FOUND) |
| 365 | COGNITIVE IMPAIRMENT (FOUND) |
| 366 | COGNITIVE DEFICITS IN ATTENTION (FOUND) |
| 367 | DEPRESSED MOOD (DISORDER) IN ALZHEIMER'S DISEASE |
| 368 | DELUSIONS (DISORDERS) IN ALZHEIMER'S DISEASE |
| 369 | SEVERE COGNITIVE IMPAIRMENT (FOUND) |
| 370 | MODERATE COGNITIVE IMPAIRMENT (FOUND) |
| 371 | IMPAIRED MEMORY (FOUND) |
| 372 | ENVIRONMENTAL INTERPRETATION DISORDER SYNDROME (FOUND) |
| 373 | DISTURBANCES IN COGNITIVE LEARNING (FOUND) |
| 374 | LACK OF THINKING ABILITY (FOUND) |
| 375 | MINIMAL COGNITIVE IMPAIRMENT (FOUND) |
| 376 | AGE-RELATED COGNITIVE DECLINE (FOUND) |
| 377 | AT RISK OF COGNITIVE DYSFUNCTION (FOUND) |
| 378 | PEOPLE IN WHEELCHAIRS (FOUND) |
| 379 | DEPENDENT ON HELPERS PUSHING WHEELCHAIRS (FOUND) |
| 380 | MINIMAL ASSISTANCE IN A WHEELCHAIR (FOUND) |
| 381 | WHEELCHAIR INDEPENDENCE (FOUND) |
| 382 | EXCRETION/INTESTINES/URINE |
| 383 | INCONTINENCE (FOUND) |
| 384 | INCONTINENCE WITHOUT SENSATION (FOUND) |
| 385 | INCONTINENCE DUE TO DETRASTER INSTABILITY (FOUND) |
| 386 | NEUROGENIC INCONTINENCE (FOUND) |
| 387 | URINARY INCONTINENCE (FOUND) |
| 388 | FECAL INCONTINENCE (FOUND) |
| 389 | APOCALYPSE DISCOVERY (FOUND) |
| 390 | ABNORMAL URINATION (FOUND) |
| 391 | FINDING (FOUND) BLADDER CONTROL |
| 392 | DISCOVERY OF URINE FLOW (FOUND) |
| 393 | A SEARCH (FOUND) RELATED TO THE ABILITY TO PASS URINE |
| 394 | LOWER URINARY TRACT SYMPTOMS (FOUND) |
| 395 | DISCOVERING (FOUND) MEASURES FOR URINATION |
| 396 | FINDING (FOUND) A DESIRE TO URINATE |
| 397 | FINDING (FOUND) A VOIDING PATTERN |
| 398 | FUNCTIONAL DYSURIA (FOUND) |
| 399 | INCOMPLETE URINATION (FOUND) |
| 400 | PRECAUTIONS FOR INSPECTION - THIRST REFLEX (FOUND) |

FIG. 36

| NUMBER | DATA ELEMENTS |
|---|---|
| 401 | NORMAL CONTROL OF URINATION (FOUND) |
| 402 | NORMAL URINATION (DETECTION) |
| 403 | URINATION FUNCTION (OBSERVABLE ENTITY) |
| 404 | EXCRETION STATUS IN URINE (OBSERVABLE ENTITY) |
| 405 | THE ABILITY TO COLLECT AND EXCRETE URINE (AN OBSERVABLE ENTITY) |
| 406 | THE ABILITY TO MAINTAIN THE URGE TO URINATE (AN OBSERVABLE ENTITY) |
| 407 | MEASUREMENT OF VOIDED VOLUME (OBSERVABLE ENTITIES) |
| 408 | CHARACTERISTICS OF DESIRE TO URINATE (OBSERVABLE ENTITIES) |
| 409 | A PATTERN OF URINATION (AN OBSERVABLE ENTITY) |
| 410 | THE PATTERN OF URINE FLOW (AN OBSERVABLE ENTITY) |
| 411 | THE ABILITY TO PASS URINE (AN OBSERVABLE ENTITY) |
| 412 | THE FLOW OF URINE (AN OBSERVABLE ENTITY) |
| 413 | THE DISCOVERY (FOUND) OF THE GUT |
| 414 | INTESTINAL ANASTOMOSIS PRESENT (FOUND) |
| 415 | INTESTINAL TROUBLE (FOUND) |
| 416 | BE AWARE OF PASSING STOOLS (FOUND) |
| 417 | A DESIRE (FOUND) TO FIND STOOL |
| 418 | FIND MEASURES FOR DEFECATION (FOUND) |
| 419 | DISCOVERY (FOUND) OF THE PASSAGE OF MECONIUM |
| 420 | RETRIEVING (FOUND) DEFECATION VOLUME |
| 421 | RETRIEVING (FOUND) THE NUMBER OF BOWEL MOVEMENTS |
| 422 | DISCOVERING (FOUND) DEFECATION RATES OR SPEEDS |
| 423 | INTESTINAL SPASM (FOUND) |
| 424 | DON'T NOTICE PASSING STOOLS (FOUND) |
| 425 | ALTERNATING CONSTIPATION AND DIARRHEA (FOUND) |
| 426 | THE SENSATION OF STARTING DIARRHEA (FOUND) |
| 427 | A SENSATION (FOUND) AS IF THE INTESTINES WERE STILL FULL |
| 428 | BOWEL RUSH (FOUND) |
| 429 | THE DISCOVERY (FOUND) OF THE LARGE INTESTINE |
| 430 | DISCOVERY (FOUND) OF THE SMALL INTESTINE |
| 431 | A DISEASE (DISORDER) OF THE INTESTINES |
| 432 | DOUBLE INCONTINENCE (FOUND) |
| 433 | URGENT NEED TO DEFECATE (FOUND) |
| 434 | MULTIPLE DIVERTICULA IN THE INTESTINE (FOUND) |
| 435 | WIND PAIN IN THE ABDOMEN (FOUND) |
| 436 | COMPLETE PASSAGE OF STOOL (FOUND) |
| 437 | DISCOVERY (FOUND) OF EXCREMENT |
| 438 | FECAL REFLEX FINDINGS (FOUND) |
| 439 | DISCOVERIES (DISCOVERIES) RELATED TO AWARENESS OF BOWEL FUNCTION |
| 440 | THE DISCOVERY (FOUND) OF HOW THE INTESTINES WORK |
| 441 | DISCOVERY (FOUND) OF THE INTESTINAL ENVIRONMENT |
| 442 | DIRT (FOUND) |
| 443 | EXCREMENT CAN BE OBSERVED (OBSERVABLE ENTITIES) |
| 444 | SAN MARCO'S INCONTINENCE SCORE (AN OBSERVABLE ENTITY) |
| 445 | TIME OF LAST BOWEL MOVEMENT (OBSERVABLE ENTITY) |
| 446 | EXCRETION STATUS OF THE INTESTINAL TRACT (OBSERVABLE ENTITIES) |
| 447 | BE AWARE OF INTESTINAL FUNCTIONS (OBSERVABLE ENTITIES) |
| 448 | STOOL/EMOTION-SYMPTOM (OBSERVABLE ENTITY) |
| 449 | THE ACTION OF THE INTESTINES (OBSERVABLE ENTITIES) |
| 450 | REQUIRES SUPERVISION FOR WHEELCHAIR MOBILITY (FOUND) |

FIG. 37

| NUMBER | DATA ELEMENTS |
|---|---|
| 451 | UNSTEADY GAIT (FOUND) |
| 452 | VISUAL IMPAIRMENT (DISORDER) |
| 453 | MILD VISUAL IMPAIRMENT (DISORDER) |
| 454 | MODERATE VISUAL IMPAIRMENT (DISORDER) |
| 455 | SEVERE VISUAL IMPAIRMENT (DISORDER) |
| 456 | IMPAIRMENT OF THE AUDITORY SYSTEM |
| 457 | DEAFNESS (DISORDER) |
| 458 | HEARING IMPAIRMENT (DISORDER) |
| 459 | AN EAR DISORDER (DISORDER) |
| 460 | NOT AWARE OF THE GENERAL DANGER (FOUND) |
| 461 | NOT AWARE OF DANGER FROM THE DEEP SEA (FOUND) |
| 462 | LACK OF COMMON SENSE OF DANGER (FOUND) |
| 463 | UNAWARE OF DANGER FROM STRANGERS (FOUND) |
| 464 | NOT AWARE OF THE DANGERS OF TRAFFIC (FOUND) |
| 465 | NOT AWARE OF THE DANGER OF FALLING FROM HEIGHTS (FOUND) |
| 466 | NOT AWARE OF DANGER FROM SHARP OBJECTS (FOUND) |
| 467 | NOT AWARE OF THE DANGER OF HOT MATERIALS (FOUND) |
| 468 | LACK OF SELF-CONSCIOUSNESS (FOUND) |
| 469 | LOW AWARENESS OF WORKPLACE SAFETY (FOUND) |
| 470 | IMPULSIVE CHARACTER (FOUND) |
| 471 | MAKE AN IMPULSIVE REMARK (FOUND) |
| 472 | DURING EXAM - IMPULSIVE BEHAVIOR (FOUND) |
| 473 | EXPLOSIVE PERSONALITY DISORDER (DISORDER) |
| 474 | ISOLATED AND EXPLOSIVE FAILURES (FAILURES) |
| 475 | COGNITIVE SEIZURE (DISORDER) |
| 476 | COGNITIVE IMPAIRMENT (DISORDER) |
| 477 | DELAYED COGNITIVE DEVELOPMENT (DISORDER) |
| 478 | MILD COGNITIVE IMPAIRMENT (DISORDER) |
| 479 | LANGUAGE-RELATED COGNITIVE IMPAIRMENT (DISORDER) |
| 480 | AGE-RELATED MEMORY LOSS (DISORDER) |
| 481 | COGNITIVE IMPAIRMENT (FOUND) |
| 482 | COGNITIVE DEFICIT ATTENTION (FOUND) |
| 483 | SEVERE COGNITIVE IMPAIRMENT (FOUND) |
| 484 | MODERATE COGNITIVE IMPAIRMENT (FOUND) |
| 485 | IMPAIRED MEMORY (FOUND) |
| 486 | ENVIRONMENTAL INTERPRETATION DISORDER SYNDROME (FOUND) |
| 487 | DISTURBANCES IN COGNITIVE LEARNING (FOUND) |
| 488 | LACK OF THINKING ABILITY (FOUND) |
| 489 | MINIMAL COGNITIVE IMPAIRMENT (FOUND) |
| 490 | AGE-RELATED COGNITIVE DECLINE (FOUND) |
| 491 | AT RISK OF COGNITIVE DYSFUNCTION (FOUND) |
| 492 | RISK OF CONFUSION (FOUND) |
| 493 | RISK OF CONFUSION (FOUND) |
| 494 | TREATMENT/TREATMENT/PHYSICAL OBJECT |
| 495 | USING PAINKILLERS (PROCEDURE) |
| 496 | INTRA-ARTERIAL ADMINISTRATION OF ANTIARRHYTHMIC DRUGS (PROCEDURE) |
| 497 | DIURETIC THERAPY (PROCEDURE) |
| 498 | ANTIDEPRESSANT THERAPY (PROCEDURE) |
| 499 | ANTIPSYCHOTIC MEDICATION (PROCEDURE) |
| 500 | BENZODIAZEPINE THERAPY (PROCEDURE) |

FIG. 38

| NUMBER | DATA ELEMENTS |
|---|---|
| 501 | ANALGESIA METHOD (PROCEDURE) |
| 502 | INTRAVENOUS ANTIARRHYTHMIC DRUGS (PROCEDURE) |
| 503 | DIURETIC THERAPY (PROCEDURE) |
| 504 | ANTIDEPRESSANT THERAPY (PROCEDURE) |
| 505 | DRUG THERAPY - ANTIPSYCHOTIC MEDICATION (PROCEDURE) |
| 506 | BENZODIAZEPINE THERAPY (PROCEDURE) |
| 507 | BEDREST CARE (REGIME/TREATMENT) |
| 508 | BED REST (REGIME/THERAPY) |
| 509 | MOBILITY AIDS (PROCEDURE) |
| 510 | ASSISTANCE IN MOVING IN BED (PROCEDURE) |
| 511 | WALKING AID (PHYSICAL OBJECT) |
| 512 | STICKS, WALKING DEVICES (PHYSICAL OBJECTS) |
| 513 | CRUTCHES (PHYSICAL OBJECTS) |
| 514 | WALKING AID (PHYSICAL OBJECT) |
| 515 | TRIPOD (PHYSICAL OBJECT) |
| 516 | CANE, DEVICE (PHYSICAL OBJECT) |
| 517 | CRUTCHES, EQUIPMENT (PHYSICAL OBJECTS) |
| 518 | CANE, DEVICE (PHYSICAL OBJECT) |
| 519 | A LONG CANE (A PHYSICAL OBJECT) |
| 520 | WALKING AIDS (PHYSICAL OBJECTS) |
| 521 | CANE/CLUTCH (PHYSICAL OBJECT) |
| 522 | PEDESTRIAN/WALKING AID (PHYSICAL OBJECT) |
| 523 | WALKING ASSIST ICE GRIP (PHYSICAL OBJECT) |
| 524 | WALKING STICK HOLDER (PHYSICAL OBJECT) |
| 525 | WALKING ASSIST HAND GRIP (PHYSICAL OBJECT) |
| 526 | TIP OF WALKING AID (PHYSICAL OBJECT) |
| 527 | PEDESTRIANS (PHYSICAL OBJECTS) |
| 528 | ELECTRONIC WALKER FOR WALKING REHABILITATION (PHYSICAL OBJECT) |
| 529 | WALKING CHAIR, UNFOLDABLE (PHYSICAL OBJECT) |
| 530 | WALKING TABLE (PHYSICAL OBJECT) |
| 531 | BASIC WALKER, UNFOLDABLE (PHYSICAL OBJECT) |
| 532 | WALKING CHAIR, FOLDABLE (PHYSICAL OBJECT) |
| 533 | BASIC WALKER, FOLDABLE (PHYSICAL OBJECT) |
| 534 | OBESE WALKER, UNFOLDABLE (PHYSICAL OBJECT) |
| 535 | OBESE WALKER, FOLDABLE (PHYSICAL OBJECT) |
| 536 | PATIENTS/MEDICAL DEVICES WALKERS, HOUSEHOLD (PHYSICAL OBJECTS) |
| 537 | PATIENT/MEDICAL DEVICE WALKER (PHYSICAL OBJECT) |
| 538 | ADMINISTRATION OF SEDATIVES (PROCEDURE) |
| 539 | BENZODIAZEPINE THERAPY (PROCEDURE) |
| 540 | ADMINISTRATION OF SEDATIVES VIA THE RECTAL ROUTE (PROCEDURE) |
| 541 | INDUCTION OF MINIMAL SEDATION (PROCEDURE) |
| 542 | INDUCTION OF DEEP SEDATION (PROCEDURE) |
| 543 | INDUCTION OF CONSCIOUS SEDATION (PROCEDURE) |
| 544 | ORAL SEDATION (PROCEDURE) |
| 545 | SEDATION WITH ANALGESICS USED TOGETHER (PROCEDURE) |
| 546 | INHALED SEDATION (PROCEDURE) |
| 547 | INTRAMUSCULAR SEDATION (PROCEDURE) |
| 548 | INTRAVENOUS SEDATION (PROCEDURE) |
| 549 | INDUCTION OF SEDATION (PROCEDURE) |
| 550 | REPLACING AN INDWELLING BLADDER CATHETER (PROCEDURE) |

FIG. 39

| NUMBER | DATA ELEMENTS |
|---|---|
| 551 | DEAERATED INDWELLING URINARY CATHETER BALLOON (PROCEDURE) |
| 552 | MOBILITY AIDS (PROCEDURE) |
| 553 | ASSISTANCE IN MOVING IN BED (PROCEDURE) |
| 554 | SELF-CARE ASSISTANCE: TRANSFER (PROCEDURE) |
| 555 | ABILITY TO MOVE PLACES WITH ASSISTANCE (FOUND) |
| 556 | GAIT TRAINING (PROCEDURE) |
| 557 | WALKING TRAINING PROCEDURES (PROCEDURE) |
| 558 | EXERCISE THERAPY (REGIME/THERAPY) |
| 559 | OTHER |
| 560 | FAMILY HISTORY |
| 561 | GETTING OUT OF THE BED |
| 562 | # NUMBER OF NURSE CALLS |
| 563 | PERIOD OF STAY |
| 564 | RISK INDICATORS |
| 565 | LUNG |
| 566 | SKIN |
| 567 | MOBILITY SCORE |
| 568 | RISK SCORE (*=FALLS,** = EWS) |
| 569 | SCOPE OF RISK (HIGH, MEDIUM, LOW) |
| 570 | MISSING RISK SCORE/RISK STRATIFICATION PARAMETERS |
| 571 | RESPONSE (NOTIFICATIONS AND ACTIONS) |
| 572 | DIFFICULTY BREATHING |
| 573 | CHRONIC OBSTRUCTIVE PULMONARY DISEASE |
| 574 | MORBID OBESITY |
| 575 | PNEUMONIA |
| 576 | BREATHING RATE OVER 30 |
| 577 | RESPIRATORY RATE LESS THAN 10 |
| 578 | SPO 2 LESS THAN 85 |
| 579 | WOBBLY |
| 580 | BLEEDING |
| 581 | CONGESTIVE HEART FAILURE |
| 582 | DIFFICULTY BREATHING |
| 583 | HDS-R |
| 584 | MMSE |
| 585 | TRANSFER LEVEL |
| 586 | IRRITABILITY |
| 587 | DRINKING ALCOHOL |
| 588 | AMOUNT OF DRINKING WATER |
| 589 | USING AN AIR MATTRESS |
| 590 | SWALLOWING FUNCTION |
| 591 | GET UP |
| 592 | NUMBER OF TIMES TO GET UP |
| 593 | DIAPERS |
| 594 | DIAPER CHANGING TIME |
| 595 | FREQUENCY OF GOING OUT |
| 596 | STAIR CLIMBING |
| 597 | FAMILY INTENTIONS |
| 598 | JOINT SITUATION |
| 599 | ENEMA |
| 600 | PAST MEDICAL HISTORY |

FIG. 40

| NUMBER | DATA ELEMENTS |
|---|---|
| 601 | MEMORY COMPREHENSION |
| 602 | SMOKING |
| 603 | LAXATIVE ADMINISTRATION |
| 604 | BLOOD PRESSURE |
| 605 | ORAL CONDITION |
| 606 | MEASURES TO PREVENT RECURRENCE |
| 607 | CAUSES OF ACCIDENT |
| 608 | DETAILS OF THE ACCIDENT |
| 609 | ACCIDENT HISTORY |
| 610 | COLLECTING HABIT |
| 611 | GROUP MALADJUSTMENT |
| 612 | WELFARE EQUIPMENT USED |
| 613 | DIETARY - STATUS OF DIAPERS |
| 614 | DIETARY COMPLEXION |
| 615 | DIETARY FACIAL CONDITION |
| 616 | EATING POSTURE |
| 617 | NUMBER OF MEALS |
| 618 | MEAL TIME |
| 619 | DIETARY ACTIVITY LEVEL |
| 620 | DIETARY CONTENT |
| 621 | DINING PLACE |
| 622 | AMOUNT OF FOOD |
| 623 | PRESSURE ULCER ASSESSMENT |
| 624 | DECUBITUS STAGE |
| 625 | NUMBER OF PROCEDURES |
| 626 | DEGREE OF INDEPENDENCE |
| 627 | EYESIGHT |
| 628 | PHYSICAL CONDITION |
| 629 | NUMBER OF FLUID INTAKE |
| 630 | WATER INTAKE |
| 631 | WATER INTAKE |
| 632 | SLEEP EFFICIENCY |
| 633 | SLEEP TIME |
| 634 | NUMBER OF GETTING OUT OF THE BED DURING SLEEP |
| 635 | SLEEP INDUCER |
| 636 | LIVING INFORMATION |
| 637 | LIFE HISTORY |
| 638 | CORRESPONDENCE CONTENT |
| 639 | BODY TEMPERATURE |
| 640 | EDGE SITTING POSITION |
| 641 | NUMBER OR FREQUENCY OF EDGE SITTING POSITION |
| 642 | MID-WAKE-UP TIME |
| 643 | DAY AND NIGHT REVERSAL |
| 644 | LONG-TERM MEMORY |
| 645 | HOSPITAL VISITS |
| 646 | A MADE-UP STORY |
| 647 | RESISTANCE |
| 648 | FALLING ASSESSMENT |
| 649 | FALLING RISK |
| 650 | TIME SPENT USING THE TOILET |

FIG. 41

| NUMBER | DATA ELEMENTS |
|---|---|
| 651 | TOILET GUIDE |
| 652 | PAIN |
| 653 | NUMBER OF DAYS OF ADMISSION |
| 654 | DATE OF ADMISSION |
| 655 | THE STATE OF URINE |
| 656 | RECOGNIZER |
| 657 | LEVEL OF COGNITIVE FUNCTION |
| 658 | COGNITIVE SYMPTOMS |
| 659 | TURNING OR ROLLING OVER |
| 660 | FALLING ASLEEP TIME |
| 661 | WANDERING |
| 662 | NUMBER OF EXCRETIONS |
| 663 | USE OF EXCRETION SENSOR |
| 664 | ABILITY TO EXCRETE |
| 665 | DEGREE OF INDEPENDENCE OF EXCRETION |
| 666 | EXCRETION RHYTHM |
| 667 | NUMBER OF MICTURITIONS |
| 668 | A PLACE TO URINATE |
| 669 | MICTURITION VOLUME |
| 670 | NUMBER OF BOWEL MOVEMENTS |
| 671 | DEFECATION VOLUME |
| 672 | THE REPETITION OF A STORY |
| 673 | PARANOIA |
| 674 | TIME BETWEEN ONE BITES |
| 675 | A TIME OF ONE BITE |
| 676 | A FEELING OF ANXIETY |
| 677 | RESTLESSNESS |
| 678 | WITH OR WITHOUT PACEMAKER |
| 679 | ROOM NUMBER |
| 680 | FECAL CONDITION |
| 681 | VERBAL ABUSE |
| 682 | VIOLENCE |
| 683 | INTENTION OF THE ASSITED PERSON |
| 684 | MONITORING SENSOR USED |
| 685 | DRUG ALLERGY |
| 686 | DEGREE OF CARE NEED |
| 687 | NUMBER OF GETTING OUT OF THE BED |
| 688 | USE OF A SENSOR TO DETECT GETING OUT OF BED |
| 689 | STAND HOLDING ABILITY |
| 690 | UNDERGOING REHABILITATION TRAINING |
| 691 | REHABILITATION CONTENT |
| 692 | NAME OF USER |
| 693 | IMPAIRED CONSCIOUSNESS |
| 694 | USE OF SPECTACLES |
| 695 | MYOPIA |
| 696 | TUBE FEEDING |
| 697 | BLOOD SUGAR CHECK |
| 698 | HOME OXYGEN |
| 699 | VISUAL FIELD CONSTRICTION |
| 700 | HEARING |

FIG. 42

| NUMBER | DATA ELEMENTS |
|---|---|
| 701 | DISIMPACTION |
| 702 | DIALYSIS MANAGEMENT |
| 703 | PRESBYOPIA |
| 704 | PHLEGM ASPIRATION |
| 705 | TREATMENT OF PRESSURE ULCERS |
| 706 | TUG |
| 707 | LEVEL OF INDEPENDENCE OF TRANSFER |
| 708 | NUMBER OF FARTS |
| 709 | AWAKENING |
| 710 | AMOUNT OF ACTIVITY |
| 711 | WAKE-UP TIME |
| 712 | BASAL METABOLISM |
| 713 | SKELETON |
| 714 | BONE DENSITY |
| 715 | BEDTIME |
| 716 | SLEEP |
| 717 | TRUNK |
| 718 | WEIGHT |
| 719 | WEIGHT CHANGE |
| 720 | BODY COMPOSITION |
| 721 | BODY MOVEMENT |
| 722 | NUMBER OF COGNITIVE ACTIONS |
| 723 | SKIN TROUBLE |
| 724 | DISCOMFORT |
| 725 | WALKING POSTURE |

FIG. 43

| NUMBER | OUTPUT DATA (SUPPORTING INFORMATION) |
|---|---|
| 1 | A TIMING WHEN TO START MEAL ASSISTANCE |
| 2 | COMMUNICATE USER CHARACTERISTICS |
| 3 | CONVEY USERS' PHYSICAL CONDITION |
| 4 | COMMUNICATE DIETARY PRECAUTIONS |
| 5 | TELL THEM WHEN THEY CAN EAT |
| 6 | TELL THEM WHAT TO WATCH OUT FOR WHEN IT COMES TO MEAL ASSISTANCE |
| 7 | MAKE SURE YOUR MOUTH IS CLEAN |
| 8 | TELL WHERE TO SIT<br>SIT ON THE HEALTHY SIDE AND HELP MEAL |
| 9 | MAKE SURE YOUR FEET ARE ON THE FLOOR |
| 10 | MAKE SURE YOUR CHIN IS ON A SLIGHT PULL |
| 11 | MAKE SURE YOU LEAN FORWARD A LITTLE |
| 12 | CHECK KNEE ANGLE AND ELBOW ANGLE |
| 13 | ADJUST THE HEIGHT OF A TABLE, CHAIR, OR PLATFORM |
| 14 | CHECK IF DIAPERS HAVE MADE YOUR POSTURE WORSE |
| 15 | ADJUST THE POSTURE WITH CUSHION |
| 16 | GIVE INSTRUCTIONS TO RAISE THE HEIGHT OF THE BED AND REMOVE THE SIDE RAILS |
| 17 | ADJUST THE ANGLE OF THE BED |
| 18 | CHECK THE ABDOMEN FOR PRESSURE |
| 19 | MAKE SURE THE NECK IS STABLE |
| 20 | CONVEY PRECAUTIONS TO AVOID FALLING OFF THE BED |
| 21 | INSTALL A BED TABLE |
| 22 | SET A MEAL OR CLEAN UP A MEAL |
| 23 | EXPLAIN THE MENU |
| 24 | INSTRUCT THE ORDER OF MEALS |
| 25 | REDUCE THE AMOUNT OF SPOONS TO.. OO |
| 26 | INSTRUCT THE SPEED AT WHICH FOOD IS FED |
| 27 | BE CAREFUL NOT TO ASPIRATE |
| 28 | MAKE SURE YOU'RE SWALLOWING WELL |
| 29 | CHECK IF YOUR DIET HAS CHANGED FROM WHAT YOU NORMALLY EAT |
| 30 | CALL OUT |
| 31 | ENCOURAGE HYDRATION |
| 32 | TELL CAREGIVERS A TIMING TO STOP EATING WHEN CONFIRMING AN EATING CONDITION |
| 33 | CHECK THE MEDICINE |
| 34 | INSTRUCT THE END OF A MEAL |
| 35 | CHECK THE AMOUNT OF FOOD EATEN |
| 36 | INSTRUCT ORAL CARE |
| 37 | CLEAN |
| 38 | RETURN THE BED POSITION TO ITS ORIGINAL POSITION |
| 39 | RAISE YOUR BACK AND BE CAREFUL NOT TO BACKFLOW |
| 40 | INSTRUCT WHERE TO PUT THE POST-ASSISTANCE POSITION CHANGE PILLOW |

FIG. 44

| NUMBER | OUTPUT DATA (SUPPORTING INFORMATION) |
|---|---|
| 41 | TIMING OF START EXCRETION ASSISTANCE |
| 42 | COMMUNICATE USER CHARACTERISTICS |
| 43 | CONVEY USERS' PHYSICAL CONDITION |
| 44 | TELL HOW LONG IT'S BEEN SINCE YOUR LAST EXCRETION |
| 45 | COMMUNICATE TOILET GUIDANCE OR DIAPER ASSISTANCE |
| 46 | INFORM ABOUT PRECAUTIONS FOR ASSISTED EXCRETION |
| 47 | TELL THE DIAPERS AND PADS TO BE PREPARED |
| 48 | TELL THEM HOW TO CHANGE POSITIONS |
| 49 | COMMUNICATE THE WORD (WHEN EXCRETION ASSISTANCE IS SUCCESSFUL) |
| 50 | COMMUNICATE THE WORD (WHEN EXCRETION ASSISTANCEFAILS) |
| 51 | MAKE SURE THERE IS NO LINGERING SMELL OF EXCREMENT |
| 52 | CHECK SHEETS AND UNDERWEAR FOR STAINS |
| 53 | REPLACE IT, IF IT'S DIRTY |
| 54 | OBSERVE EXCREMENT AND CHECK FOR ABNORMALITIES |
| 55 | COLOR, SHAPE, SMELL, QUANTITY |
| 56 | CHECK YOUR PHYSICAL CONDITION, INCLUDING YOUR PUBIC REGION, BUTTOCKS, AND SACRUM |
| 57 | TELL THEM YOU NEED BEDSORE CARE |
| 58 | TELL TO APPLY OINTMENT |
| 59 | PROMOTE FLUID INTAKE |
| 60 | TELL THEM IF THERE ARE ANY CHANGES IN ADL OR PHYSICAL CONDITION |
| 61 | TELL WHEN TO DEFECATE NEXT TIME |
| 62 | INSTRUCT THE POSTURE IN WHICH CLOTHING PRESSURE IS APPLIED |
| 63 | INSTRUCT WHERE TO PUT THE POST-ASSISTANCE POSITION CHANGE PILLOW |
| 64 | VENTILATE |
| 65 | RETURN THE BED POSITION TO ITS ORIGINAL POSITION |
|  | ·TOILET GUIDANCE (TOILET, PORTABLE) |
| 66 | COMMUNICATE THE TIMING |
| 67 | CALL OUT |
| 68 | COMMUNICATE A FALL-PREVENTION CHECKPOINT |
| 69 | MAKE SURE YOUR FEET ARE ON THE FLOOR |
| 70 | TELL THEM WHERE TO WAIT |
| 71 | CHECK YOUR HEALTH AFTER DEFECATION |
| 72 | CHECK WHERE TO PLACE THE TOILET PAPER |
|  | ·DIAPER ASSISTANCE (ON THE BED, ETC.) |
| 73 | INSTRUCT THE EQUIPMENT TO BE USED |
| 74 | DIRECT WHERE TO PUT THE TOOLS |
| 75 | MANIPULATE THE HEIGHT OF THE BED AND GIVE INSTRUCTIONS TO REMOVE/ATTACH THE SIDE RAILS |

FIG. 45

| NUMBER | OUTPUT DATA (SUPPORTING INFORMATION) |
|---|---|
| 76 | TRANSFER – TIMING OF START TRANSFER ASSISTANCE |
| 77 | COMMUNICATE USER CHARACTERISTICS |
| 78 | CONVEY USERS' PHYSICAL CONDITION |
| 79 | COMMUNICATE ADL |
| 80 | TELL WHETHER THE POSITION CAN BE CHANGED |
| 81 | TELL WHETHER IT'S POSSIBLE TO GET UP |
| 82 | TELL WHETHER IT'S POSSIBLE TO SIT THE EDGE SITTING POSITION |
| 83 | TELL THE LEVEL OF TRANSFER |
| 84 | CALL OUT |
| 85 | INSTRUCT THE MEANS OF TRANFERRING OR MOVING |
| 86 | COMMUNICATE THE FALLING RISK LEVEL |
| 87 | INSTRUCT HOW TO CHANGE POSITION OF THE ASSITED PERSON IN ASSISTANCE |
| 88 | INSTRUCT HOW TO ASSIST SOMEONE GET UP |
| 89 | INDICATE WHERE TO SLEEP |
| 90 | RETURN THE BED TO ITS ORIGINAL POSITION |
| 91 | INSTRUCT WHERE TO PUT THE POST-ASSISTANCE POSITION CHANGE PILLOW |
|  | ·WHEELCHAIR |
| 92 | CHECK THE WHEELCHAIR FOR ABNORMALITIES |
| 93 | TELL THE ORDER OF ASSISTANCE FROM BED REST TO TRANSFER |
| 94 | COMMUNICATE WHEELCHAIR PREPARATION AND INSTALLATION LOCATION |
| 95 | CHECK TO SEE IF THE BRAKES ARE ON |
| 96 | COMMUNICATE A FALLING-PREVENTION CHECKPOINT |
| 97 | TELL THEM WHAT NOT TO HURT THEIR LOWER BACK |
| 98 | COMMUNICATE THE TIMING AND WORDS OF THE CALL |
| 99 | CONVEY THE PHYSICAL CONDITION OF THE DAY |
| 100 | TELL TO FIX A SITTING POSITION |
| 101 | CONTROL THE HEIGHT OF THE BED, INSTRUCT TO REMOVE/ATTACH SIDE RAILS |
| 102 | ADJUST THE ANGLE OF THE BED |
| 103 | INDICATE THE HEIGHT OF THE BED WHEN SITTING |
|  | ·A CANE |
| 104 | CHECK THE CANE FOR ABNORMALITIES |
| 105 | CHECK THE CANE WITH THE HEALTHY SIDE IF THE ASSITED PERSON HAS IT |
| 106 | INSTRUCT TO STAND ON THE OTHER SIDE OF THE CANE |
| 107 | CHECK THE ORDER IN WHICH THE CANE IS USED |
|  | ·LIFT |
| 108 | CHECK IF THERE IS ANYTHING WRONG WITH THE LIFT |
| 109 | INSTRUCT HOW TO USE SLING SHEETS |
| 110 | GIVE INSTRUCTIONS ON HOW TO USE THE LIFT |
| 111 | MANIPULATE THE HEIGHT OF THE BED AND GIVE INSTRUCTIONS TO REMOVE/ATTACH THE SIDE RAILS |
| 112 | INSTRUCT THE HANGER NOT TO COLLIDE |

INFORMATION PROCESSING DEVICE AND INFORMATION PROCESSING METHOD

TECHNICAL FIELD

The present invention relates to an information processing device, an information processing method, etc. This patent application claims the benefit of priority to Japan Patent Application Serial No. 2021-032143, filed Mar. 1, 2021, which is incorporated by reference herein in its entirety.

BACKGROUND ART

Traditionally, systems used in medical settings and nursing homes are known. Patent Document 1, for example, discloses a technique for instructing a method of assistance to move the assisted person.

CITATION LIST

Patent Literature

Patent Document 1: Japanese Patent Laid-Open No. 2007-233471

SUMMARY OF THE INVENTION

Technical Problem

The information processing device and the information processing method that appropriately support the assistance of the assisted person by the caregivers Solution to a Problem The information processing device according to the present embodiment includes a factor determination unit configured to determine whether the behavior of an assisted person is an abnormal behavior of a dementia factor based on (1) information on the dementia level of the assisted person and (2) at least one of the environmental information, the excretion information, and the sleep information of the assisted person, and a support information output unit configured to output the support information to support an assistance of the assisted person by a caregiver based on the determination result of the factor determination unit and sensor information that is a sensing result about the assisted person or the caregiver assisting the assisted person.

BRIEF DESCRIPTION OF THE DRAWINGS

FIG. 1 shows an example of the configuration of an information processing system including an information processing device.

FIG. 11 shows a configuration example of a neural network for outputting a support information.

FIG. 14 shows an example of a first association information.

FIG. 15 shows an example of a second association information.

FIG. 16 shows an example of a third association information.

FIG. 28 is a detailed example of input data in supporting the assistance of a assisted person by a caregiver.

FIG. 29 is a detailed example of input data in supporting the assistance of a assisted person by a caregiver.

FIG. 30 is a detailed example of input data in supporting the assistance of a assisted person by a caregiver.

FIG. 31 is a detailed example of input data in supporting the assistance of a assisted person by a caregiver.

FIG. 32 is a detailed example of input data in supporting the assistance of a assisted person by a caregiver.

FIG. 33 is a detailed example of input data in supporting the assistance of a assisted person by a caregiver.

FIG. 34 is a detailed example of input data in supporting the assistance of a assisted person by a caregiver.

FIG. 35 is a detailed example of input data in supporting the assistance of a assisted person by a caregiver.

FIG. 36 is a detailed example of input data in supporting the assistance of a assisted person by a caregiver.

FIG. 37 is a detailed example of input data in supporting the assistance of a assisted person by a caregiver.

FIG. 38 is a detailed example of input data in supporting the assistance of a assisted person by a caregiver.

FIG. 39 is a detailed example of input data in supporting the assistance of a assisted person by a caregiver.

FIG. 40 is a detailed example of input data in supporting the assistance of a assisted person by a caregiver.

FIG. 41 is a detailed example of input data in supporting the assistance of a assisted person by a caregiver.

FIG. 42 is a detailed example of input data in supporting the assistance of a assisted person by a caregiver.

FIG. 43 is a detailed example of output data in support of a meal assistance.

FIG. 44 is a detailed example of output data in support of an excretion assistance.

FIG. 45 is a detailed example of output data in support of a transfer and mobility assistance.

DESCRIPTION OF EMBODIMENT

Figure 2A:
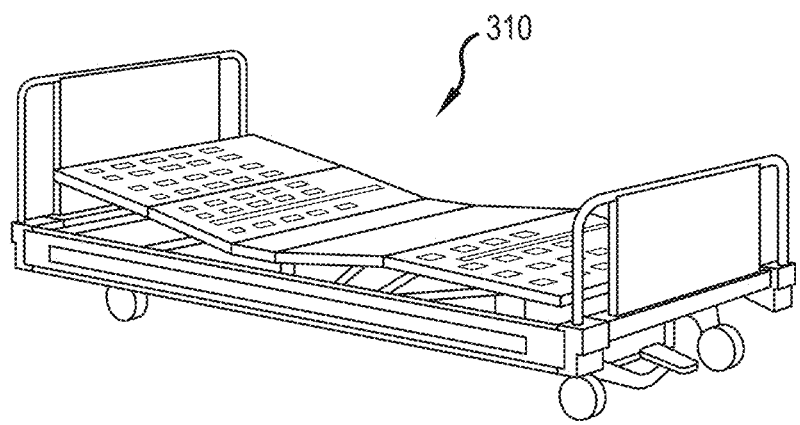
FIG. 2A shows an example of a nursing bed, which is a care device.

Hereafter, the present embodiment will be described with reference to the drawings. In the case of drawings, identical or equivalent elements shall be denoted by the same symbol, and duplicate descriptions shall be omitted. It should be noted that this embodiment described below does not unreasonably limit the contents of the claims. Also, not all of the configurations described in the present embodiment are mandatory configuration requirements.

1. System Configuration Example

FIG. 1 is a configuration example of an information processing system 10 including an information processing device according to this embodiment. The information processing system 10 according to this embodiment provides instructions to the caregivers so that appropriate assistance can be provided regardless of the skill level of the caregivers by digitizing the "intuition" or "tacit knowledge" of the caregivers, for example, in a care facility. The information processing system 10 shown in FIG. 1 includes a server system 100, a caregiver device 200, a care device 300 which is used for a care, and a sensor group 400. However, the configuration of the information processing system 10 is not limited to FIG. 1, and various modifications such as omitting a part or adding other configurations are possible. In addition, the fact that modifications such as omission or addition of a configuration can be carried out is the same in FIGS. 3 and 4, which will be described later.

The information processing device of this embodiment corresponds to, for example, the server system 100. However, the method of this embodiment is not limited to this, and the processing of the information processing device may be executed by distributed processing using the server system 100 and other devices. For example, the information processing device of this embodiment may include the server system 100 and the caregiver device 200. An example in which the information processing device is the server system 100 is described below.

The server system 100 is connected to the caregiver device 200, a care device 300, and a sensor group 400 for example via the network NW. The network NW here is, for example, a public communication network such as the Internet, but may also be a LAN (Local Area Network). For example, the caregiver device 200, a care device 300 and a sensor group 400 are placed in a nursing home, etc. The server system 100 performs processing based on the information from the sensor group 400, outputs information to the caregiver device 200 based on the processing results, and remotely controls the care device 300, etc based on the processing results.

In the FIG. 1, each of the caregiver device 200, the care device 300, and the sensor group 400 can communicate with the server system 100 through the network NW, but this is not limited. For example, a relay device (not shown) may be provided in a nursing home. The relay device is a device capable of communicating with the server system 100 through the network NW. The information output by the sensor group 400 is aggregated by a relay device using a LAN in the nursing home, and the relay device may transmit the information to the server system 100. Information from the server system 100 is transmitted to the relay device, and the relay device may transmit necessary information to the caregiver device 200 or the care device 300. For example, in nursing homes, it is assumed that multiple caregiver devices 200 and multiple care devices 300 will be used simultaneously. The relay device may perform processing to select the caregiver device 200 or the care device 300 to which the information from the server system 100 is to be transmitted. Alternatively, the relay device may be a manager terminal used by the manager of the nursing home and may operate based on the operator's input. For example, the information from the server system 100 is displayed on the display of the relay device, and the manager who sees the displayed result may select the caregiver device 200 or care device 300 as a destination device. In addition, as described above, various modifications can be made to the information processing device of this embodiment, and for example, the above relay device may be included in the information processing device.

The server system 100 may be a single server or may include multiple servers. For example, the server system 100 may include a data base server and an application server. The database server stores various data to be described later using FIG. 3. The application server performs the processing described later using FIG. 7, FIG. 8, FIG. 18 to FIG. 23, etc. The multiple servers here may be physical servers or virtual servers. If a virtual server is used, the virtual server may be located on one physical server or distributed among multiple physical servers. As described above, the detailed configuration of the server system 100 in this embodiment can be modified in various ways.

The caregiver device 200 is a device used by a caregiver who assists an assisted person (Patients, residents) in a nursing home, etc., to present information to the caregiver or to input information by the caregiver. For example, the caregiver device 200 may be a device carried or worn by the caregiver. For example, the caregiver device 200 includes a mobile terminal device 210 and a wearable device 220. The mobile terminal device 210 is, for example, a smartphone, but may be any other mobile device. The wearable device 220 is a device that can be worn by the caregivers, for example, an earphone or headphone and a headset containing a microphone. The wearable device 220 may be a glasses-type device, a wristwatch-type device, or a device of another shape. The caregiver device 200 may be another device such as a PC (Personal Computer).

A care device 300 is a device used to provide care (including assistance) for an assisted person in a nursing home, etc. Whereas the caregiver device 200 is primarily a device for presenting information to the caregiver, the care device 300 is a device for directly assisting the assisted person. For example, the care device 300 may include a nursing bed 310 which can change an angle of bottoms (which may be plate-shaped or mesh-shaped, regardless of shape) and a height, and a lift 320 for transferring the assisted person from the nursing bed 310 to a wheelchair, etc. The care device 300 may also include other equipment such as a wheelchair, a walker, rehabilitation equipment, and a serving cart to serve meals.

Figure 2B:
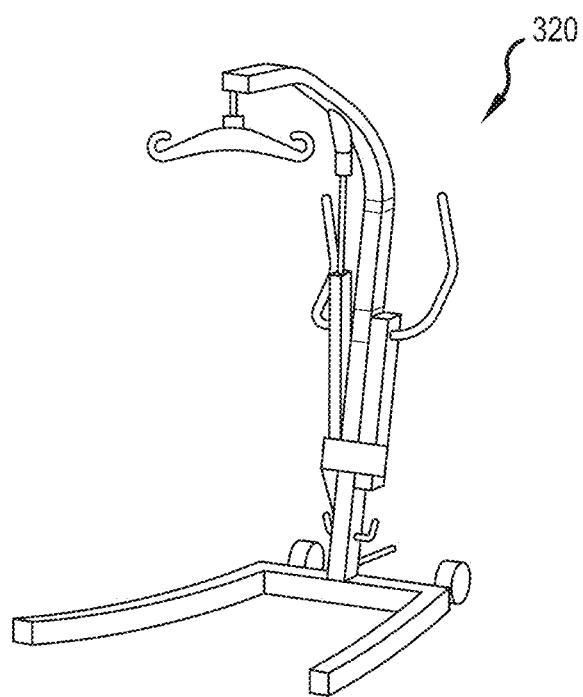
FIG. 2B shows an example of a lift, which is a care device.

FIG. 2A shows an example of a nursing bed 310. The nursing bed 310 is capable of changing the height and angle of the multiple bottoms, respectively. This makes it possible to flexibly change the posture of the assisted person lying on the nursing bed 310. FIG. 2B is an example of the lift 320. The lift 320 is a device used, for example, to transfer a care recipient who has a low ADL (Activity of Daily Living) rating index and is difficult to transfer by hand.

The sensor group 400 includes a plurality of sensors located in a nursing home, etc. The sensor group 400 may include a motion sensor 410, an imaging sensor 420, and an odor sensor 430. The motion sensor 410 may be an acceleration sensor, a gyro sensor or any other sensor capable of detecting motion. The motion sensor 410 may be a sensor that detects the motion of the assisted person or a sensor that detects the motion of the caregiver. The imaging sensor 420 is a sensor that converts an object image formed through a lens into an electrical signal. The odor sensor 430 is a sensor that detects and quantifies odor. The sensor group 400 can also include various sensors such as temperature sensors, humidity sensors, illuminance sensors, magnetic sensors, position sensors, barometric pressure sensors, etc.

FIG. 1 shows the caregiver device 200, the care device 300, and the sensor group 400 separately. For example, the sensors included in the sensor group 400 may be located in living rooms, dining rooms, hallways, stairs, etc., in nursing homes. For example, a camera including the imaging sensor 420 is placed at each location in a nursing home. Sensing devices may also be used to sense information needed for caregiving. Not only the necessary information is sensed and but also the location information is detected by providing the sensors at each location in a nursing home.

Figure 2C:
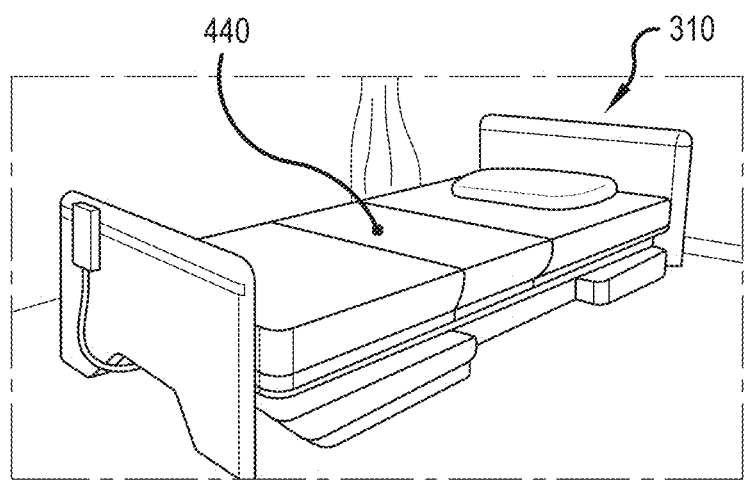
FIG. 2C shows an example of a sensing device.
Figure 2D:
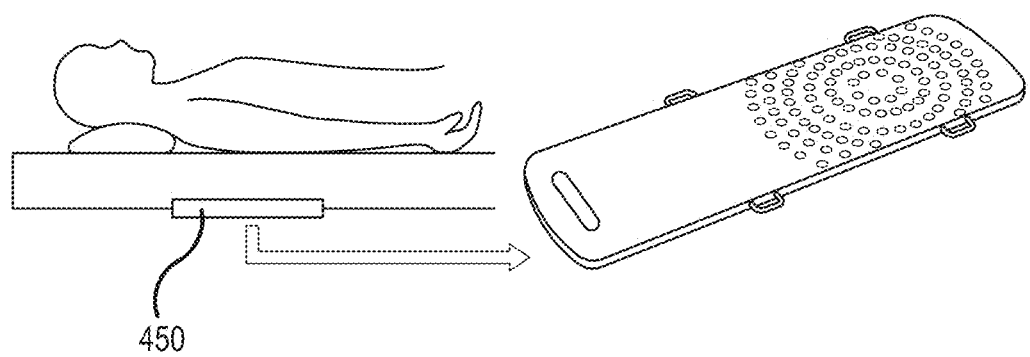
FIG. 2D shows an example of a sensing device.

For example, FIG. 2C shows a example of the sensing device 440 placed on the mattress of a nursing bed 310. The sensing device 440 shown in FIG. 2C includes, for example, the odor sensor 430 to detect whether the assisted person has excreted. The sensing device 440 may be capable of determining whether the assisted person is ill from body odor or breath. FIG. 2D also shows an example of a sensing device 450 placed under a mattress (placed between the nursing bed 310 and the mattress) on the nursing bed 310. The sensing device 450 shown in FIG. 2D includes, for example, a pressure sensor and can detect the heart rate, respiratory rate and activity of the assisted person. The sensing device 450 may be able to determine whether the assisted person is in a sleep state or not and whether the assisted person is in a nursing bed.

However, the method of this embodiment is not limited to the above examples, and the sensors included in the sensor group 400 may be provided in the caregiver device 200 or the care device 300. For example, as the sensors included in the sensor group 400, cameras, accelerometers, gyro sensors, GPS (Global Positioning System) sensors, etc. in the mobile terminal device 210 may be used. In addition, the care device 300 may be provided with a motion sensor for detecting the posture of the care device 300, and a camera for imaging the assisted person or the caregivers using the care device 300, etc.

Figure 3:
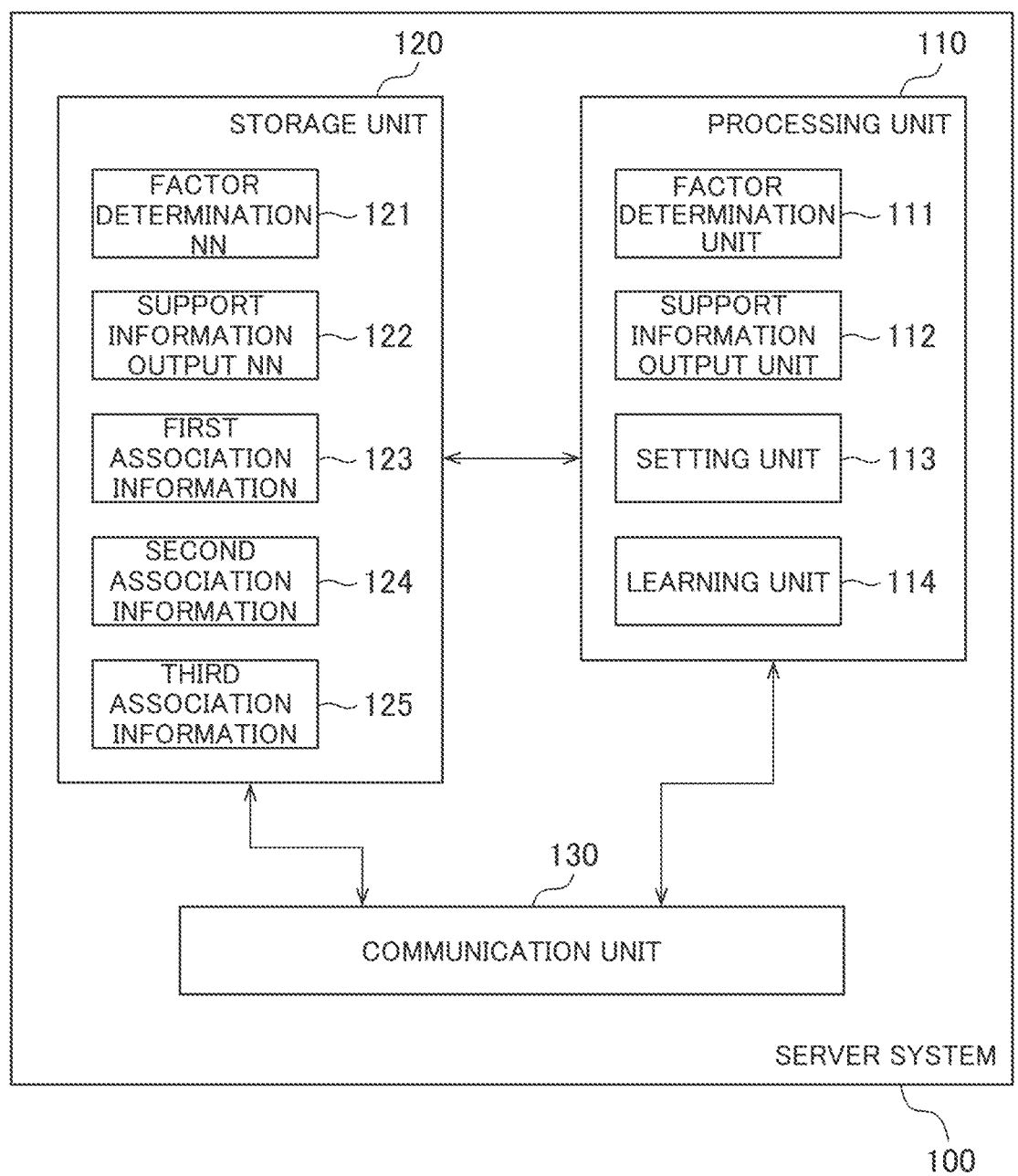
FIG. 3 shows an example of a server system configuration.

FIG. 3 is a block diagram showing a detailed configuration example of the server system 100. The server system 100 includes, for example, a processing unit 110, a storage unit 120, and a communication unit 130.

The processing unit 110 of this embodiment includes the following hardware. The hardware may include at least one of a circuit for processing digital signals and a circuit for processing analog signals. For example, the hardware may be one or more circuit devices mounted on a circuit board or one or more circuit elements. One or more circuit devices are, for example, IC (Integrated Circuit) or FPGA (field-programmable gate array). One or more circuit elements are, for example, resistors, capacitors, etc.

The processing unit 110 may be realized by the following processors. The server system 100 of this embodiment includes a memory for storing information and a processor operating on the information stored in the memory. The information includes, for example, programs and various kinds of data. The processor includes the hardware. The processor can use a variety of processors such as a CPU (Central Processing Unit), GPU (Graphics Processing Unit), and DSP (Digital Signal Processor). The memory may be a semiconductor memory such as SRAM (Static Random Access Memory), DRAM (Dynamic Random Access Memory), or flash memory, or a register, a magnetic storage device such as a Hard Disk Drive (HDD), or an optical storage device such as an optical disk device. For example, the memory stores instructions that can be read by a computer, and if the processor executes the instructions, the functions of the processing unit 110 may work. The instructions described above may be the instruction set that makes up the program, or the instruction that instruct the processor's hardware circuitry to operate.

The processing unit 110 includes a factor determination unit 111, a support information output unit 112, a setting unit 113, and a learning unit 114.

The factor determination unit 111 determines whether the assisted person's behavior is an abnormal behavior of the dementia factor on accordance with an input including at least dementia level information of the assisted person. For example, the factor determination unit 111 determines whether the behavior of the assisted person is an abnormal behavior of the dementia factor based on (1) the dementia level information of the assisted person and (2) at least one of the environmental information of assisted person, the excretion information of the assisted person and the sleep information of the assisted person. The details of each information will be described later.

The support information output unit 112 outputs support information to support the assistance of the assisted person by the caregiver based on the determination result output by the factor determination unit 111 and the sensor information which is the sensing result about the assisted person or the caregiver who assists the assisted person. The detail of the support information is provided below.

The setting unit 113 performs setting processing when using the information processing system 10 according to this embodiment. For example, a caregiver who is a user of the information processing system 10 may be able to set which information should be output from a large number of pieces of support information. In this case, as will be described later with reference to FIG. 17 and FIG. 18, the setting unit 113 performs processing such as accepting the setting operation by the caregiver and updating the setting information. The setting unit 113 may also perform setting processing to add user-specific custom support information as the output. Detailed examples will be described later using FIGS. 25A to 25 D, etc.

The learning unit 114 outputs the learned model by performing a machine learning based on the training data. The machine learning described above is, for example, supervised learning. The training data in supervised learning is a data set made an association between the input data corresponding to the input of the model and the correct answer data representing the appropriate output data when the input data is input. The learning unit 114 may generate a learned model, for example, by performing the machine learning using a neural network. Hereafter, the neural networks are referred to as NN. For example, the learning unit 114 performs processing to generate a factor determination NN 121 and a support information output NN 122. Details of the processing in the learning unit 114 will be described later. However, the machine learning is not always required in this embodiment, and the learning unit 114 can be omitted. In the case of the machine learning is performed, the learning process can be executed in a learning device different from the server system 100, and the learning unit 114 can be omitted in this case as well.

The storage unit 120 is a work area of the processing unit 110 and stores various information. The storage unit 120 can be realized by a variety of memories, and the memory may be a semiconductor memory such as SRAM, DRAM, ROM, flash memory, etc, a register, a magnetic storage device, or an optical storage device.

The storage unit 120 stores information used for processing in the factor determination unit 111 and information used for processing in the support information output unit 112. For example, the storage unit 120 may store the factor determination NN 121 acquired by the machine learning using NN and a support information output NN 122 acquired by the machine learning using NN. Here, the factor determination NN 121 and the support information output NN 122 include the parameters used for the operation using the structure in addition to the information specifying the structure of the NN. A parameter is specifically a weight whose value is determined by the machine learning.

The storage unit 120 may also store a first association information 123, a second association information 124, and a third association information 125. The first association information 123 is information that associates a caregiver with information indicating whether or not to output each support information to the caregiver. The second association information 124 is information that associates the support information with the sensor information required to output the support information. The third association information 125 is information that associates a given nursing home with sensor information that can be acquired in the nursing home. The Detailed examples of each association information will be described later with reference to FIGS. 14 to 16. The storage unit 120 may store other information.

The communication unit 130 is an interface for communication via a network NW and includes, for example, an antenna, a radio frequency (RF) circuit, and a baseband circuit. The communication unit 130 may operate according to control by the processing unit 110 or may include a processor for communication control different from the processing unit 110. The communication unit 130 is an interface for performing communication according to, for example, TCP/IP (Transmission Control Protocol/Internet Protocol). However, various modifications can be made to the detailed communication system.

Figure 4:
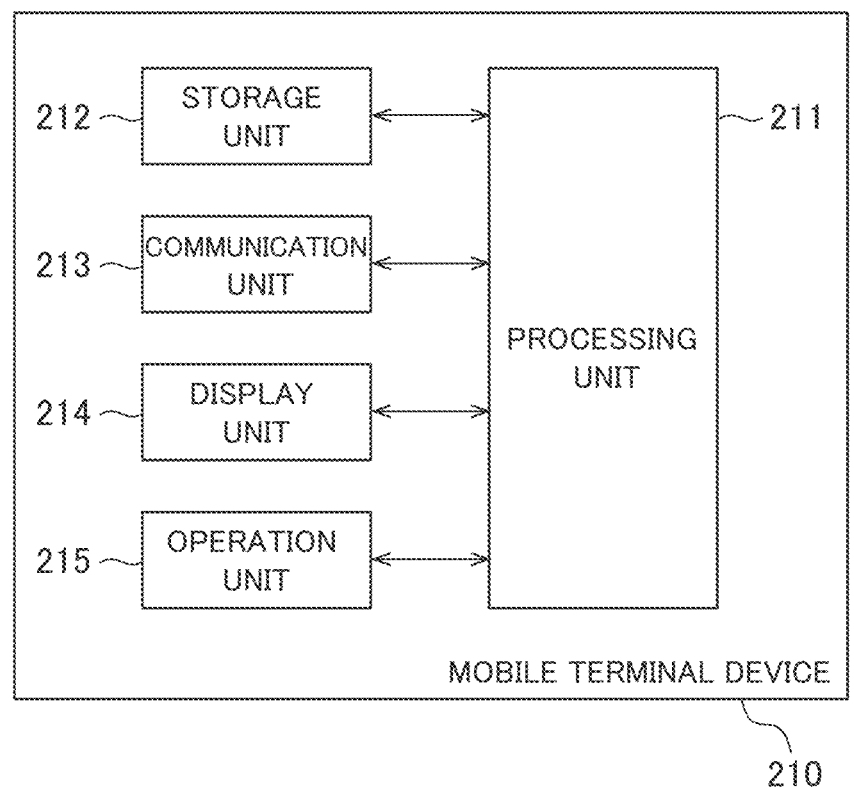
FIG. 4 shows an example of the configuration of a mobile terminal device.

FIG. 4 is an example of the caregiver device 200 and a block diagram showing a detailed configuration example of the mobile terminal device 210. The mobile terminal device 210 includes, for example, a processing unit 211, a storage unit 212, a communication unit 213, a display unit 214, and an operation unit 215.

The processing unit 211 is composed of a hardware including at least one of a circuit for processing digital signals and a circuit for processing analog signals. The processing unit 211 may also be realized by a processor. It is possible to use a variety of processors such as CPU, GPU, and DSP. The processor executes instructions stored in the memory of the mobile terminal device 210, thereby realizing the function of the processing unit 211 as processing.

The storage unit 212 is a work area of the processing unit 211 and is realized by various memories such as SRAM, DRAM, ROM, etc.

The communication unit 213 is an interface for communication via a network NW and includes, for example, an antenna, an RF circuit, and a baseband circuit. The communication unit 213 communicates with the server system 100 through, for example, the network NW.

The display unit 214 is an interface for displaying various kinds of information and may be a liquid crystal display, an organic EL display, or an another type display. The operation unit 215 is an interface that accepts user operations. The operating unit 215 may be a button or the like provided in the mobile terminal device 210. The display unit 214 and the operation unit 215 may be a touch panel constructed as one unit.

Also, the mobile terminal device 210 may have a light emitting part, a vibration part, a sound output part, or other part which is not shown in FIG. 4. The light-emitting part is, for example, LED (light emitting diode), which emits light. The vibrating part is, for example, a motor, which gives an alarm by vibration. The sound output unit is a speaker, for example, and provides sound notification. Also, as described above, the mobile terminal device 210 may include sensors included in the sensor group 400.

2. Factor Determination and Support Information Output

The information processing device of this embodiment performs a processing to determine the factors of the behavior of the assisted person, and a processing to output support information supporting the assistance of the assisted person by the caregiver. In this way, it is possible to have the caregiver provide appropriate assistance according to the assisted person by taking into account factors such as dementia. The machine learning is described below as a detailed example of a method for determining the factors and performing the support information output processing. However, the method of this embodiment is not limited to the one using the machine learning, and various modifications can be performed. In the following, we describe an example of using NN as the machine learning, but other methods such as support vector machines (SVMs) may be used for the machine learning, or other methods developed from NN or SVM may be used.

2.1 Brief Description of the NN

Figure 5:
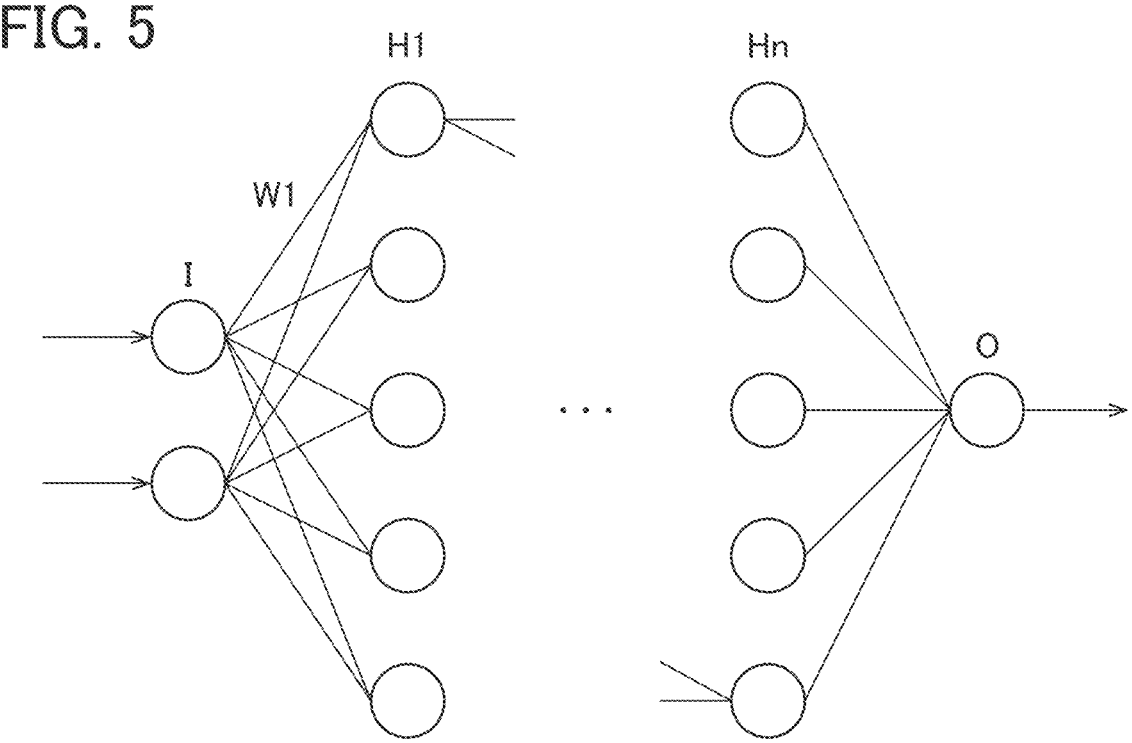
FIG. 5 is an illustration of the neural network.

FIG. 5 shows an example of the basic structure of the NN. One circle in FIG. 5 is called a node or neuron. In the example of FIG. 5, the NN has an input layer, two or more intermediate layers, and an output layer. The input layer is I, the intermediate layers are H1 and Hn, and the output layer is O. In the example of FIG. 5, the number of nodes in the input layer is 2, the number of nodes in the middle layer is 5, and the number of nodes in the output layer is 1. However, the number of layers in the middle layer and the number of nodes contained in each layer can be modified variously. FIG. 5 also shows an example in which each node included in a given layer is connected to all nodes included in the next layer, and various modifications can be made to this configuration as well.

The input layer accepts the input value and outputs value to the intermediate layer H1. In the example of FIG. 5, the input layer I accepts two kinds of input values. Each node in the input layer may perform some processing for the input value and output the value after the processing.

In the NN, a weight is set between two connected nodes. W1 in FIG. 5 is the weight between the input layer I and the first intermediate layer H1. W1 represents the set of weights between a given node in the input layer and a given node in the first intermediate layer. For example, W1 in FIG. 5 is information containing 10 weights.

Each node of the first intermediate layer H1 preforms an operation to weighted add the output of the node of the input layer I connected to the node using the weight W1, and further operation to add the bias. In addition, at each node, the output of the node is determined by applying the activation function, which is a nonlinear function, with the summation result. The activation function may be a ReLU function, a sigmoid function, or any other function.

The operation is same for subsequent layers. That is, in a given layer, the output of the preceding layer is weighted and added with the weight W, and the bias is added and then the output to the next layer is calculated by applying an activation function. The NN treats the output of the output layer as the output of the NN.

As we can see from the above description, to obtain the desired output data from the input data using NN, it is necessary to set the appropriate weights and biases. In learning, we should prepare the training data made an association between a given input data and the correct data representing the correct output data in the input data. The learning process of the NN indicates a process for finding the most probable weight based on the training data. In the learning process of the NN, various learning methods such as backpropagation are known. In the present embodiment, since these learning methods can be widely applied, a detailed description is omitted.

Also, the NN is not limited to the configuration shown in FIG. 5. For example, as the NN, a convolutional neural network (CNN: convolutional neural network) may be used. The CNN has a convolution layer and a pooling layer. The convolution layer performs convolution operations. Convolution operations described here are specifically filtering. The pooling layer performs processing to reduce the vertical and horizontal sizes of the data. In the CNN, the characteristics of the filter used in the convolution operation are learned by performing learning processing using an backpropagation method or the like. That is, the weights in the NN include the filter characteristics in the CNN. As the NN, a network with other configuration such as RNN (Recurrent neural network) may be used.

2.2 Factor Judgment

Figure 6:
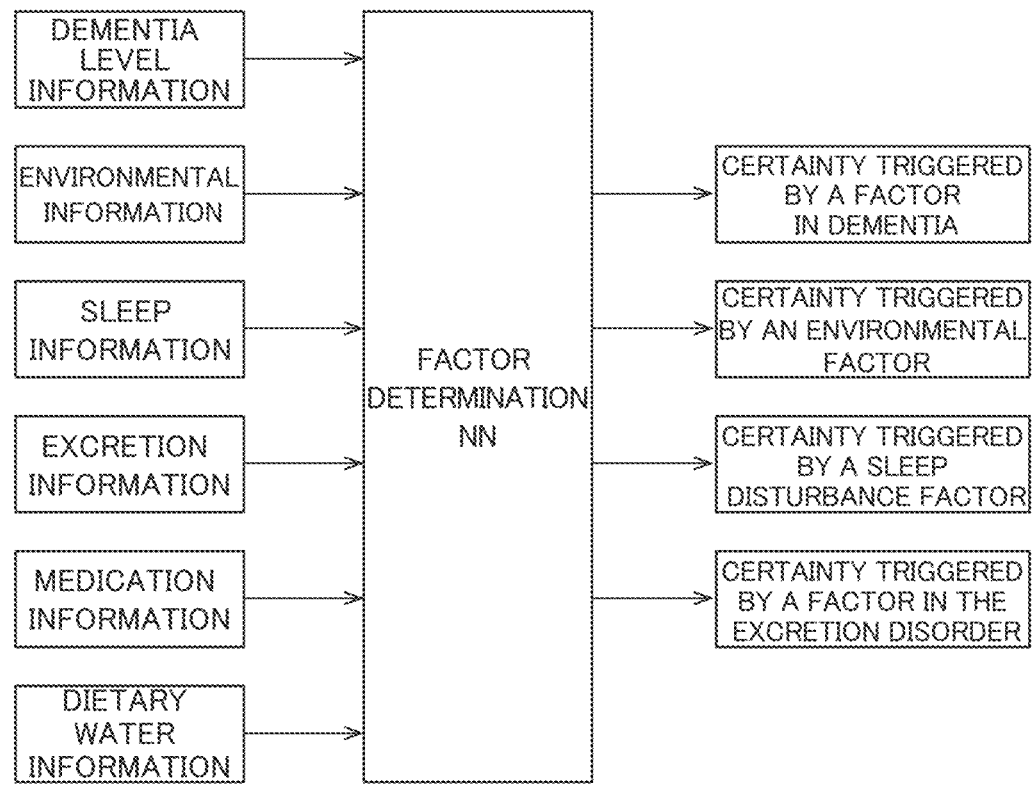
FIG. 6 is an example of an input and output of the neural network for a factor determination.

FIG. 6 illustrates the input and output data of the factor determination NN 121 used for factor determination. The input data in factor determination includes, for example, dementia level information. The input data also includes at least one of environmental information, sleep information and excretion information. FIG. 6 shows an example where the input data includes all of the environmental information, the sleep information and the excretion information. The input data may also contain other information. For example, as shown in FIG. 6, the input data may include medication information, dietary water information. The configuration of the factor determination NN 121 is not limited to FIG. 6, and various modifications can be performed.

Dementia level information is information that represents the degree of progression of dementia in the assisted person. For example, the dementia level information may be a score on the Mini-Mental State Examination (MMSE), a score on the revised Hasegawa's Brief Intelligence Scale (HDS-R), or other information representing the results of a dementia test. The dementia level information may be based on brain images obtained using computed tomography (CT) or magnetic resonance imaging (MRI). For example, the dementia level information may be the result of a doctor's diagnosis based on a brain image, the brain image itself, or the result of some kind of image processing on the brain image.

Environmental information is information that represents the living environment of the assisted person. The environmental information includes temperature information representing the temperature of the living environment of the assisted person, humidity information representing humidity, illuminance information representing illuminance, and barometric information representing barometric pressure. For example, a temperature sensor, a humidity sensor, an illuminance sensor, and a barometric pressure sensor are placed in the patient's living room or a place regularly used, such as a dining room, and temperature, humidity, illuminance, and barometric pressure information are acquired based on the output of each sensor.

The environmental information may also include information related to sound. For example, a microphone is placed in a living environment such as a living room, and the information collected by the microphone is used as environmental information. The environmental information can be information related to sound pressure or information representing the results of frequency analysis. The environmental information may also include information about the time etc, when a particular sound occurs.

The environmental information may also include information related to the nursing bed 310 used by the assisted person. The information about the nursing bed 310 may refer to the model of the nursing bed 310, may be specific information or information such as the type and firmness of mattresses used in conjunction with the nursing bed 310. The information about the nursing bed 310 may also include information representing the driving result of the nursing bed 310. For example, information such as the angle and height of the bottom of the nursing bed 310 and the time when the nursing bed 310 drives may be used as the environmental information.

The sleep information is information representing the sleep state of the assisted person. For example, sleep information may be detected using a sensing device 450 or the like which is shown in FIG. 2D. The sleep information may also be detected using a wristwatch-type device including a photoelectric sensor or the like for detecting pulse rate. The sleep information includes, for example, information such as sleep start time, wake-up time, daily sleep duration, sleep depth, number and time of arousal during sleep, heart rate, respiratory rate and amount of activity during sleep.

The excretion information includes information representing the state of excretion of the assisted person. For example, the excretion information may be detected using the sensing device 440 which is shown in FIG. 2C. The sensing device 440 outputs the presence or absence of excretion of the assisted person, the type of excretion, and the timing when the excretion is determined based on the odor sensor 430 for example. The excretion information includes information such as, for example, the number of excretions in a given period, the interval of excretion, and the type of excretion. The excretion information may also include information such as an imaged image of the diaper after excretion and comments added by the caregiver.

The medication information is information that identifies the medicine administered to the assisted person. For example, the medication information is information that represents the name of the medicine taken by the assisted person, dose, time of dose, etc. The medication information may also include information on prescriptions issued to the assisted person.

Dietary water information is information that represents the food and water taken by the assisted person. The dietary water information, for example, includes the time of day you ate, the menu, and how much you actually ate. The dietary water information may also include information identifying ease of eating, such as firmness and size of ingredients. The dietary water information also includes the time of taking water, type of water (water, tea, etc.), and amount of taking water.

In the learning stage, the training data for creating the factor determination NN 121 is acquired by associating the above input data in a prescribed period with the correct answer data. The prescribed period described above may be a fixed period such as one day. Alternatively, the prescribed period may be a period that is set on the basis of the time of occurrence of any abnormal behavior if the assisted person behaves abnormally.

The correct answer data may also be given by an expert with specialized knowledge, such as a physician and a doctor. If the assisted person behaves abnormally, the expert makes a diagnosis of the assisted person and identifies the factors contributing to the abnormal behavior. The correct answer data described here is information representing the identified factors. For example, the correct answer data indicates whether the behavior is triggered by a dementia factor, an environmental factor, a sleep disorder factor, or a excretion disorder factor. For example, in the case that one data set is defined as the result of associating the correct answer data with the input data corresponding to one period of one assisted person, the training data including a large number of data sets is acquired by increasing the number of assisted persons and the target period.

The learning unit 114 of the server system 100 acquires the training data for determining factors. Then, by performing the machine learning based on the training data, the factor determination NN 121 is generated.

Figure 7:
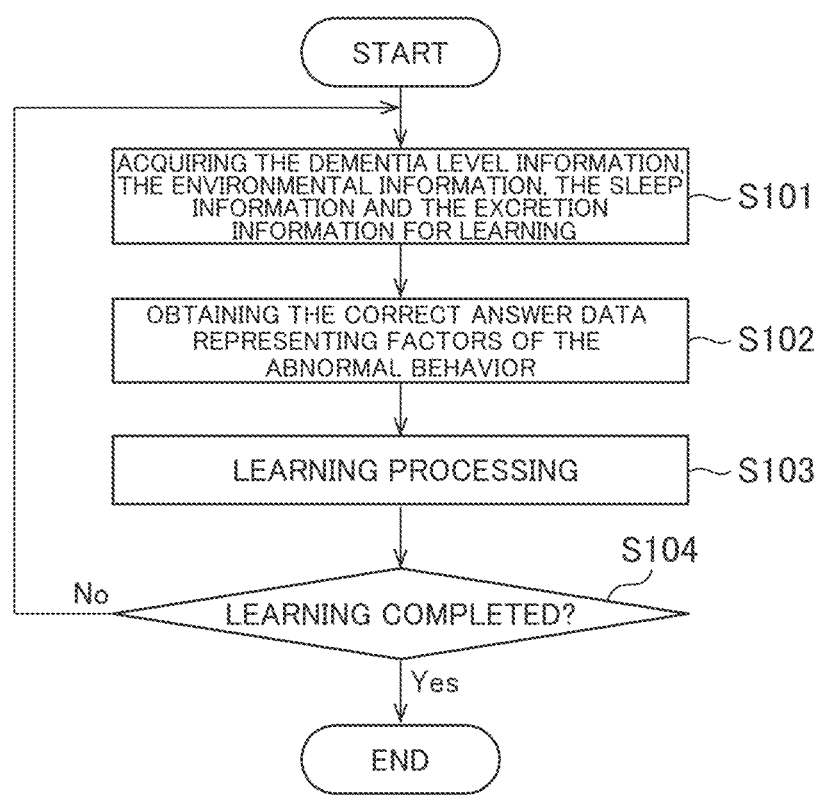
FIG. 7 is a flow chart explaining a learning process for determining factors.

FIG. 7 is a flowchart illustrating the learning process for generating the factor determination NN 121. When this processing is started, firstly in a step S101, the learning unit 114 acquires the input data for learning. The input data described here are same as described above and include, for example, the dementia level information, the environmental information, the sleep information and the excretion information. The input data may also include other information such as the medication information and the dietary water information.

Also, in a step S102, the learning unit 114 obtain the correct answer data which associates with the input data. For example, the learning unit 114 performs the processing of the steps S101 and S102 by reading out any one of the training data sets acquired in the learning stage.

In a step S103, the learning unit 114 performs processing to update the weight of the NN. Specifically, the learning unit 114 inputs the input data acquired in the step S101 into the factor determination NN 121, and acquires the output data by performing a forward operation using the weights at that stage. The learning unit 114 obtains an objective function based on the output data and the correct answer data. The objective function described here is, for example, an error function based on the difference between the output data and the correct answer data, or a cross-entropy function based on the distribution of the output data and the distribution of the correct answer data.

For example, if the output layer of the factor determination NN 121 is a known softmax layer, the output of the output layer is probability data whose sum is 1. For example, the output layer includes four nodes from the first node to the fourth node. The output value of the first node represents a "certainty that the behavior of the assisted person is triggered by a factor in dementia." The output value of the second node represents a "certainty that the behavior of the assisted person is triggered by an environmental factor." The output value of the third node represents a "certainty that the behavior of the assisted person is triggered by a sleep disturbance factor." The output value of the fourth node represents a "certainty that the behavior of the assisted person is triggered by a factor in the excretion disorder." The correct answer data are data in which the value of the factor that is the correct answer is 1 and the other values are 0. For example, if an expert determines that the dementia factor is a factor, data that the possibility for the dementia factor corresponds to 1 and the possibility of other three factors corresponds to 0 are used as correct data.

The learning unit 114 updates the weights so that, for example, the error function decreases. As a weight updating method, the back-propagation method and the like described above are known, and these methods can be widely applied in this embodiment.

In the step S104, the learning unit 114 determines whether or not to terminate the learning process. For example, multiple datasets included in training data may be separated into a learning data and a validation data. The learning unit 114 may complete the learning process when processing to update the weights using all the learning data is performed, or may complete the learning process when the correct answer rate by the validation data exceeds a prescribed threshold.

If the learning process is not completed, the learning unit 114 returns to the step S101 to continue the process. That is, the learning unit 114 reads a new data set from the training data and performs processing to update the weights based on the new data set.

When the learning process is completed, the learning unit 114 stores the factor determination NN 121 at that stage in the storage unit 120 as a learned model. Note that FIG. 7 is an example of learning processing, and the method of this embodiment is not limited to this. For example, in the machine learning, the methods such as a batch learning are widely known, and these methods can be widely applied in this embodiment.

Figure 8:
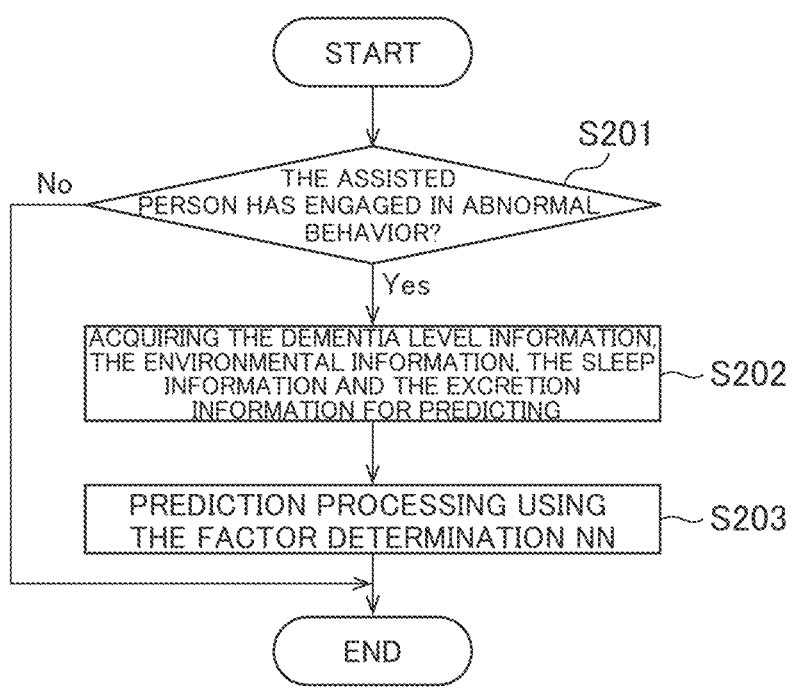
FIG. 8 is a flow chart explaining a factor determination process.

FIG. 8 is a flowchart explaining the processing of the factor determination unit 111 in an inference stage. When this processing is started, firstly, in a step S201, the factor determination unit 111 determines whether or not the assisted person has engaged in abnormal behavior that is suspected to be dementia. The factor determination unit 111 may automatically determine whether the behavior of the assisted person is abnormal behavior based on the sensor information about the assisted person, etc. For example, the sensor group 400 includes a motion sensor 410, an imaging sensor 420, a microphone, etc., and the factor determination unit 111 determines the presence or absence of abnormal behavior by detecting the movement or vocalization of the assisted person. Alternatively, the caregiver may observe the movement of the assisted person himself or herself and input the observation results using the caregiver device 200 or the like. In this case, the factor determination unit 111 performs the processing of step S201 based on the input of the caregiver. When it is determined that the assisted person does not exhibit any abnormal behavior, the factor determination unit 111 terminates the processing without performing a step S202 or later.

When it is determined that the assisted person has behaved abnormally, in the step S202, the factor determination unit 111 acquires the input data concerning the assisted person. For example, the storage unit 120 acquires and stores the dementia level information about the assisted person, the sensor information collected by the sensor group 400, and the like via the communication unit 130. The dementia level information may be obtained, for example, at a nursing home, and transmitted from the equipment at the nursing home to the server system 100. The factor determination unit 111 performs processing to read out, as the input data, the information on the dementia level, the environmental information, the sleep information, the excretion information and the like corresponding to a prescribed period, among the collected data concerning the target assisted person.

In a step S203, the factor determination unit 111 reads the factor determination NN 121 from the storage unit 120. Then, the input data acquired in the step S202 is input to the factor determination NN 121, and the output data is obtained by performing a forward operation. The output data of the factor determination NN 121 are, for example, 4 probability values representing the certainty of each factor as described above. The factor determination unit 111 determines, for example, the factor that maximizes the probability value as the factor of the abnormal behavior of the assisted person. For example, if a value representing the certainty of a dementia factor is greater than the certainty of the other 3 factors, the factor determination unit 111 determines that the abnormal behavior is triggered by a dementia factor. The output of the factor determination unit 111 is not limited to this, and may be the 4 probability values themselves or a value calculated based on them.

The factor determination unit 111 periodically executes the processing shown in FIG. 8, for example. The frequency of processing is arbitrary but may be, for example, once a day. In this way, the presence or absence of abnormal behavior of the assisted person and the factors in the event of abnormal behavior can be determined on a regular basis. For example, the factor determination unit 111 may execute the processing which is shown in FIG. 8 every morning and determine the assistance policy for the day based on the processing result. In addition, various modifications can be made to the processing of the factor determination unit 111, such as executing the processing which is shown in FIG. 8 without waiting for the next processing timing, when the abnormal behavior is observed in the assisted person.

In addition, as a separate processing from the processing using the factor determination NN 121, an example of determining whether the behavior of the assisted person is abnormal behavior has been described above (see Step S201 in FIG. 8). However, a NN for making a determination including whether the behavior is abnormal may be generated.

For example, the factor determination NN 121 may have the sensor information or the like representing the behavior of the assisted person in addition to the input data shown in FIG. 6. The factor determination NN 121 may include a node for outputting the "certainty of no abnormality in the behavior of the assisted person." in addition to the node for outputting the certainty of the four factors shown in FIG. 6. In the learning phase, the training data is generated by using data in the absence of abnormal behavior in addition to data in the presence of abnormal behavior. Specifically, the correct answer data associated with the input data includes data representing "no abnormal behavior." In this case, the factor determination unit 111 estimates the presence or absence of abnormal behavior and factors in the event of abnormal behavior by inputting the input data to the factor determination NN 121.

2.3 Assistance Support 2.3.1 Input and Output

Figure 9:
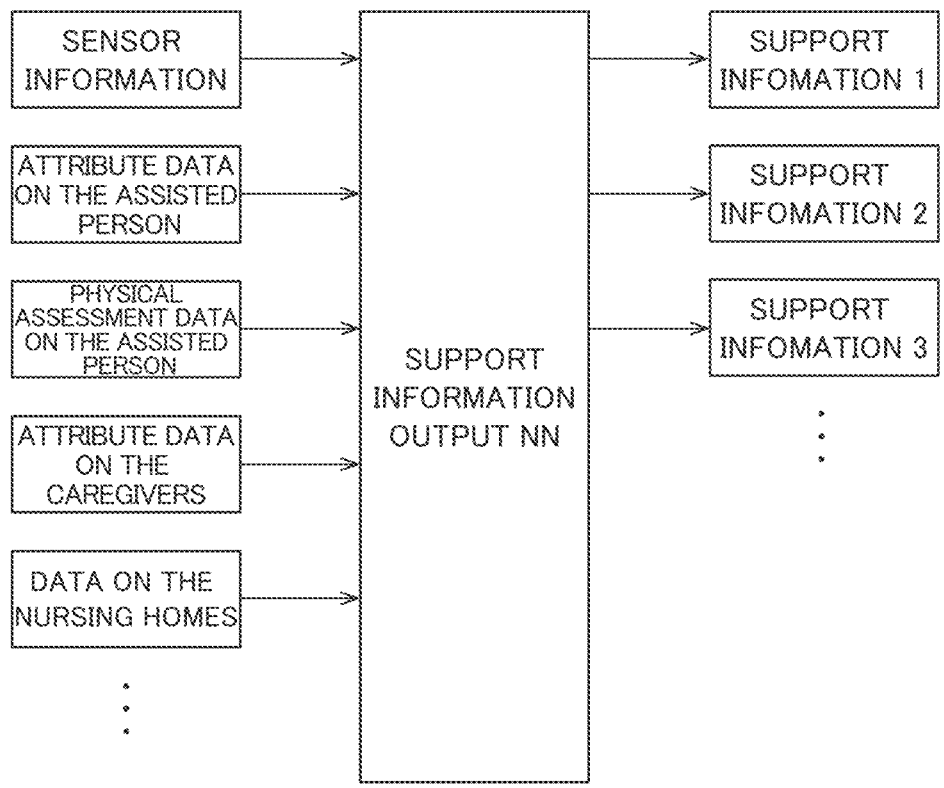
FIG. 9 shows an example of an input and output of the neural network for a support information output.

FIG. 9 is a diagram illustrating the schematic input data of the support information output NN 122 used to output support information. As shown in FIG. 9, the input data may include the sensor information. The sensor information includes information sensing the assisted person or information sensing the assisted person. The sensor information is output from sensors included in the sensor group 400, for example.

In addition, the sensor information may include information that senses the living environment of the assisted person. The sensor information in this case corresponds to the environmental information described above, for example. For example, the sensor information may include outputs of temperature sensors, humidity sensors, illuminance sensors, barometric pressure sensors, microphones, etc.

The input data also includes attribute data on the assisted person, as well as physical assessment data that represents a physical assessment. The attribute data of the assisted person includes information such as age, sex, height, weight, medical history, medication history, etc. The physical assessment data includes information such as ADL assessment, rehabilitation history, fall risk and pressure ulcer risk.

The input data also includes attribute data on the caregivers and data on the nursing homes. The attribute data on the caregivers includes the caregiver's age, sex, height, weight, assistance experience, and held qualifications. The data on the nursing homes includes information such as nursing schedules, the number and usage of care device 300, the number of the assisted person, and statistical data on the level of care needs at the nursing home.

FIGS. 28 to 42 illustrate details of data used as input in supporting the assistance of the assisted person by the caregivers in this embodiment, and in a narrow sense, they show examples of input data of the support information output NN 122. As shown in the FIGS. 28 to 42, the input data in this embodiment can utilize various kinds of information. It is not mandatory that all the input data shown in the FIGS. 28 to 42 be acquired, even if some information is omitted. The other information not shown in the FIGS. 28 to 42 may be added.

In addition, in the case that assistance of the assisted person by the caregivers is divided into multiple assistance actions, the output data of the support information output NN 122 is information for supporting the performance of each assistance action. For example, the output data of the support information output NN 122 is support information for determining the start timing of the assistance action, the movement and vocalization during the assistance action, and the type and amount of objects to be provided to the assisted person.

FIGS. 43 to 45 are diagrams illustrating details of data used in supporting the assistance of the assisted person by the caregiver in this embodiment, and in a narrow sense, they are diagrams illustrating examples of support information that is output data of the support information output NN 122.

FIG. 43 is an example of the support information that is output in meal assistance where the caregivers assist the assisted person to eat the meal. For example, in the meal assistance, the caregiver grasps the characteristics of the assisted person and explains them to the assisted person himself/herself in an easy-to-understand manner, thereby facilitating to execute the meal assistance. For example, in the case of an assisted person who is characterized by poor chewing ability, it is possible to take ways to prevent aspiration if the caregiver is aware of this, and it is also useful to guide the assisted person by saying, "we have softened the rice, so let's chew it well." The output data of Number 1 in FIG. 43 is support information to "convey the characteristics of the user" to the caregiver, and it may be data representing the characteristics of the assisted person itself, or it may be information converted to make it easy for the caregiver to understand. Also, as mentioned above, the caregiver may communicate the characteristics of the assisted person to the assisted person himself or herself, and the output data of Number 1 in the FIG. 43 may contain data for that, also Number 2 and thereafter may be same as Number 1, and the output data shown in the FIG. 43 includes information to support the caregiver's various behaviors in meal assistance.

FIG. 44 is an example of support information that is output in the excretion assistance where the caregivers assist the assisted person to excrete. Note that the excretion assistance may be performed in the toilet or by using a diaper, Number 66-72 represent the output data of the excretion assistance in the toilet and Number 73-75 represent the output data of the excretion assistance using a diaper.

FIG. 45 is an example of support information that is output in transfer assistance and moving assistance where the caregivers assist the assisted person to transfer and move the assisted person. The transferring assistance and the moving assistance may vary in the presence or absence of equipment or in the type of equipment, depending on the condition of the assisted person and the availability of the lift. In the example of the FIG. 45, Number 92-103 represents output data when the assistance is provided using a wheelchair, Number 104-107 represents output data when the assistance is provided using a cane, and Number 108-112 represents output data when the assistance is provided using a lift.

As shown in FIGS. 43 to 45, the support information may include information that supports at least one of the meal assistance, the excretion assistance, and the transferring or moving assistance. In this way, it becomes possible to appropriately support the assistance that is highly necessary in the nursing homes, etc. For example, by supporting the meal assistance, it is possible to control incidents such as aspiration and to improve the nutritional status of the assisted person. By supporting the excretion assistance, it becomes possible to control the excretion leakage, reduce the number of man-hours to deal with the excretion leakage and the risk that occurs, reduce the excretion disorder, and reduce the falling risk. In addition, by supporting the transferring and moving assistance, it is possible to reduce the falling risk and to prepare the need for the assisted person in advance.

2.3.2 Sample Configuration of NN for Support Information Output

Figure 10:
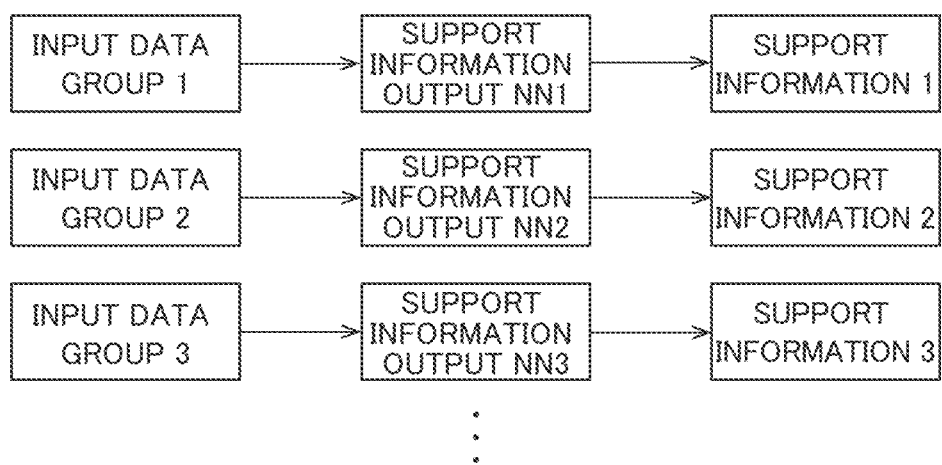
FIG. 10 shows a configuration example of a neural network for outputting a support information.
Figure 12:
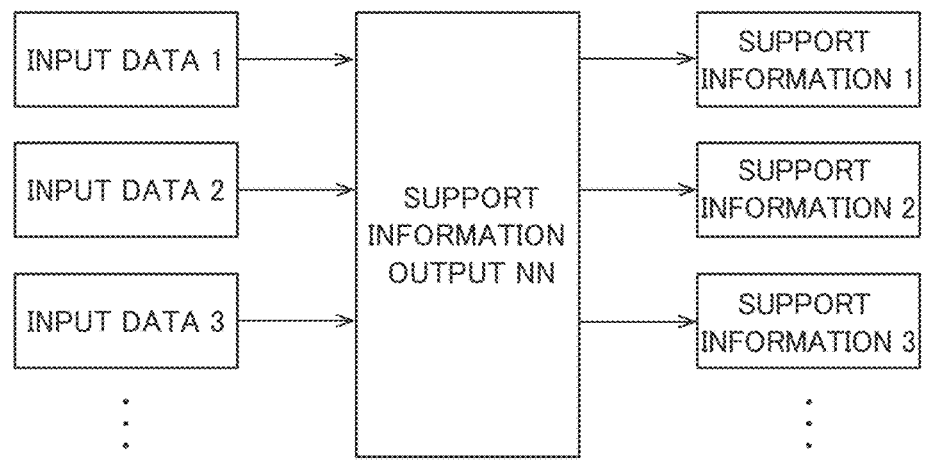
FIG. 12 shows a configuration example of a neural network for outputting a support information.

FIGS. 10 to 12 show the detailed configuration examples of the support information output NN 122 shown in FIG. 9. As shown in FIG. 10, the support information output NN 122 may be a set of multiple NNs in which each NN outputs one support information. The support information 1 in FIG. 10 corresponds to any one of the support information shown in FIGS. 43 to 45. The input data group 1 represents one or more input data required to output the support information 1 among the multiple input data shown in FIGS. 28 to 42. The same applies to the support information 2 and later.

Also, as shown in the FIG. 11, the support information output NN 122 may a set of multiple NNs that can collectively output a number of output data. In the example of FIG. 11, the support information output NN 122 includes a meal assistance support information output NN, a excretion assistance support information output NN, and a transferring and moving assistance support information output NN.

For example, a meal assistance support information output NN may output multiple meal assistance support information. The output data of the meal assistance support information output NN corresponds to the multiple support information shown in the FIG. 43. The input data of the meal assistance support information output NN represents the multiple input data required for outputting the meal assistance support information among the multiple input data shown in the FIGS. 28 to 42. The output of the excretion assistance support information output NN corresponds to the multiple support information shown in the FIG. 44. The output of the transferring and moving assistance support information output NN corresponds to the multiple support information shown in FIG. 45.

Also, as shown in the FIG. 12, the support information output NN 122 may consists of 1 NN. The input data of the NN in FIG. 12 is the set of all the data shown in FIGS. 28 to 42, and the output data is the set of all the support information shown in FIGS. 43 to 45.

Also, the configuration of the support information output NN 122 is not limited to the FIGS. 10 to 12. For example, by dividing the meal assistance support information output NN into several pieces, the intermediate configuration of the FIG. 10 and the FIG. 11 may be used. In addition, the specific configuration of the support information output NN 122 can be modified in various ways.

Figure 13:
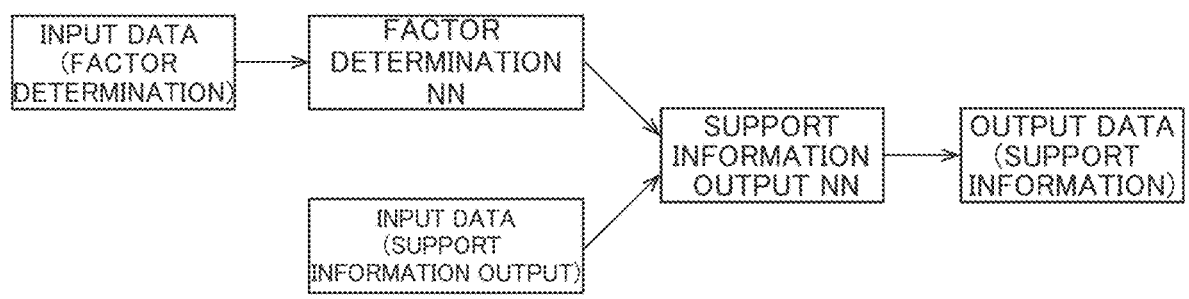
FIG. 13 shows an example of the relationship between a neural network for determining factors and a neural network for outputting a support information.

FIG. 13 shows an example of the relationship between the factor determination NN 121 and the support information output NN 122. The input data for factor determination in FIG. 13 is the input in the FIG. 6 and includes dementia level information, etc. The input data of the support information output NN 122 is the input in the FIG. 9, specifically, the data shown in FIGS. 28 to 42. Some input data for factor determination and input data for support information output may overlap.

In the example shown in the FIG. 13, the output data of the factor determination NN 121 is used as part of the input data of the support information output NN 122. The output data of the factor determination NN 121 may be information to identify one factor that is the determination result as described above or may be information based on multiple probability values. As shown in the FIG. 10 or the FIG. 11, when the support information output NN 122 includes multiple NNs, the output data of the factor determination NN 121 may be input to all NNs or to some NNs. In this way, the support information can be output based on the result of the factor determination in the factor determination unit 111. As a result, it is possible to make the caregiver understand the degree of dementia progression of the assisted person, and to provide various kinds of assistance according to the degree of dementia progression.

If there is no abnormal behavior in the assisted person, the output of the factor determination NN 121 may be treated as 0. Also, as described above, the factor determination NN 121 may be capable of outputting information indicating "no abnormal behavior."

However, in the method of the present embodiment, the determination result by the factor determination unit 111 may be used to output the support information, and the specific method is not limited to the example in the FIG. 13.

2.3.3 Learning Processing and Inference Processing

The flow of learning processing of the support information output NN 122 by the learning unit 114 is the same as the flow for creating the factor determination NN 121. The training data for creating the support information output NN 122 includes a data set in which correct answer data representing assistance results performed by a skilled caregiver using tacit knowledge is associated with input data.

For example, in the case of the meal assistance to an assisted person, at least the sensors required for the meal assistance are turned on among the sensor group 400. As a result, among the input data shown in the FIGS. 28 to 42, data related to the meal assistance is acquired by the sensor group 400 and stored in the storage unit 120 of the server system 100. In addition, data representing the results of the assistance of the caregiver, such as the posture the skilled caregiver made the assisted person take (corresponding to Number 9-12 in the FIG. 43, etc.), the timing of serving the meal with the spoon (corresponding to Number 26 in the FIG. 43), and the amount served per bite (corresponding to Number 25 in FIG. 43), are stored in the storage unit 120 as correct data.

The learning unit 114 obtains the output data by inputting the input data among the training data into the support information output NN 122 and by performing a forward operation using the weights at that time. Moreover, the learning unit 114 obtains an objective function (e.g., an error function such as a mean squared error function) based on the output data and the correct answer data, and updates the weight so that the error is reduced by using the backpropagation method or the like. The support information output NN 122 at the end of learning is stored in the storage unit 120 as a learned model.

As shown in the FIG. 13, the output of the factor determination NN 121 may be included in the input of the support information output NN 122. In this case, the input data in the training data includes the information representing the factors of the abnormal behavior of the assisted person. For example, as described in the learning process of the factor determination NN 121, the correct answer data imparted by an expert such as a physician may be used as one of the input data in the training data. Alternatively, when the learning processing of the factor determination NN 121 has already been completed, the inference processing using the factor determination NN 121 may be performed, and the result may be used as one of the input data in the training data, as shown in FIG. 8.

The correct answer data, as in the example above, is information that represents the results of assistance performed by a skilled caregiver using implicit knowledge. It is possible for a skilled caregiver to provide assistance that is naturally appropriate for the assisted person, considering the degree of dementia progression of the assisted person, etc. Thus, it is possible to machine learn appropriate assistance according to the factors of abnormal behavior by using the results of assistance of skilled caregivers as correct answer data. The processing after acquiring the training data is the same in this case. That is, the learning unit 114 performs the forward operation using the input data in the training data, obtains an error function from the output data and the correct answer data, and updates the weights to minimize the error.

The support information output unit 112 of the server system 100 acquires the input data shown in the FIGS. 28 to 42 in the inference stage. The input data here may include data that can output the desired support information, and it is not essential to acquire all the input data in the FIGS. 28 to 42. Also, the support information output unit 112 acquires the determination result of the factor determination unit 111 as one of the input data. The support information output unit 112 reads the learned support information output NN 122 from the storage unit 120 and inputs the input data into the support information output NN 122. As shown in the FIGS. 11 and 12, in case of that a NN capable of outputting multiple pieces of support information is used and only some of the support information is required to be output, some of the input data may not have been acquired. In this case, the support information output unit 112 may, for example, set the value of unacquired input data to 0. The support information output unit 112 obtains support information as output data by performing forward operation.

3. Processing Flow

Next, the flow of detailed processing to support the assistance of the assisted person by the caregivers in the assisted living facility, etc. is explained.

3.1 Factor Estimation of Behavior

First, the server system 100 determines whether or not abnormal behavior is observed in the assisted person, and if abnormal behavior is observed, what is the factor of the abnormal behavior, apart from processing for initiating and executing a detailed assistance sequence.

For example, the factor determination unit 111 periodically performs the processing described above using the FIG. 8. In this way, the presence or absence of abnormal behavior and the factors of abnormal behavior can be determined for each of the multiple assisted persons who are assistance targets. In the following explanation, it is assumed that the result of the factor determination by the factor determination unit 111 has been obtained.

3.2 Assisted Support 3.2.1 User Settings

The examples of the support information in this embodiment are shown in FIGS. 43 to 45. The support information output unit 112 may output all this support information. However, if too much information is reported, inexperienced caregivers may not be able to grasp the content or not be able to recognize the difference in importance from process to process. Also, since the caregivers with some experience can properly perform a prescribed assistance without any support, the notification of support information may make the caregivers with some experience annoying. Therefore, in this embodiment, the users who are the caregivers may be able to set the support information to be output.

The storage unit 120 of the server system 100 may store the first association information 123. The FIG. 14 is a detailed example of the first association information. As shown in the FIG. 14, the first association information 123 is information that associates a caregiver ID that identifies the caregiver with support information and information that represents the output setting of the support information.

The output settings include active and inactive. When the prescribed support information is set to be active, the support information output unit 112 outputs the support information to the subject caregiver. When the prescribed support information is set as inactive, the support information output unit 112 does not output the support information to the subject caregiver. In this way, the support information to be output can be flexibly set for each caregiver.

However, as shown in FIGS. 28 to 42, there are so many types of input data assumed in this embodiment, and the nursing homes may not be able to obtain all the input data. For example, due to constraints such as budgets and the structure of nursing homes, it may not be possible to deploy the necessary sensors to obtain the prescribed input data. In this case, by missing input data, it is possible not to obtain the prescribed support information with sufficient accuracy.

Thus, the support information output setting includes "can't output" in addition to an "active" or an "inactive". "can't output" indicates a setting that does not output support information because required input data could not be obtained. The "inactivity" is different from "can't output" because it represents the required input data can be obtained but the support information is intentionally not output.

For example, the storage unit 120 of the server system 100 may store the second association information 124 and the third association information 125. The FIG. 15 shows a detailed example of the second association information 124. As shown in the FIG. 15, the second association information 124 includes the support information and the required input data set required for the output of the support information. The support information is any of the multiple data shown in the FIGS. 43 to 45. The required input data group is one or more of the data shown in the FIGS. 28 to 42. The required input data group may be, for example, data specified by the user. Alternatively, the support information output NN 122 may be created for each of the multiple candidate input data groups, and the candidate input data group with the highest accuracy rate using the validation data may be selected as the required input data group. In addition, the required input data group is not limited to one set, and multiple candidate input data groups with correct rate greater than a predetermined threshold may be used as the required input data group.

The FIG. 16 is a detailed example of the third association information 125. The third association information 125 is information that associates nursing homes with the input data that can be obtained at the nursing homes. For example, a person in charge of a nursing home may select input data that can be obtained at the nursing home and transmit the selection results to the server system 100. Alternatively, the sensor group 400 deployed in the nursing home transmits information identifying the nursing home to the server system 100 in association with the sensor information. The processing unit 110 of the server system 100 may create the third association information 125 based on the acquisition history of the sensor information.

The setting unit 113 of the server system 100 determines whether or not each support information can be output for each nursing home based on the second association information 124 and the third association information 125. Specifically, the setting unit 113 determines whether or not the support information can be output based on whether or not the required input data group necessary for the output of the support information is included in the input data group obtainable in the target nursing home.

Also, there is a correspondence between the input data and the sensor used to acquire the input data. Therefore, the storage unit 120 may store the fourth association information that associates the input data with one or more sensors used to acquire the input data. By using the fourth association information in addition to the second association information 124 and the third association information 125, it is possible to determine whether or not the support information can be output on a sensor-by-sensor basis. Alternatively, the fourth association information may not be provided separately, instead, the input data of the second association information 124 and the third association information 125 may be replaced with the information of the sensor.

Also, a device including a prescribed sensor is not limited to one. For example, if the motion sensor 410 and the imaging sensor 420 are required, a device such as a smartphone including both a camera and an acceleration sensor may be utilized, or two separate devices may be utilized.

Among the cameras, the multiple model cameras with different resolutions, different magnifications, etc. are available. Therefore, the storage unit 120 may store a fifth association information that associates the sensor with the device including the sensor. In this case, the data can be managed on a device-by-device basis. For example, if a nursing home designates a device that has already been installed, the sensors included in the device and input data that can be obtained using the sensors are identified in the server system 1000. It is possible to improve a user convenience because it is not necessary for the person in charge of the nursing home or the caregiver to grasp the sensors included in the device or the input data that can be acquired by the device.

An example of determining whether the support information can be output on a nursing home basis is explained above (see, for example, the FIG. 16). However, the method of this embodiment is not limited to this. For example, if a nursing home has a first space for residents with high levels of care needs and a second space for residents with low levels of care needs, the first space may have many sensors and the second space may have fewer sensors. In this case, the server system 100 may separately manage the support information that can be output in the first space and the support information that can be output in the second space. In addition, various modifications can be made to the detailed methods, such as managing whether or not the support information can be output for each assisted person.

Figure 17:
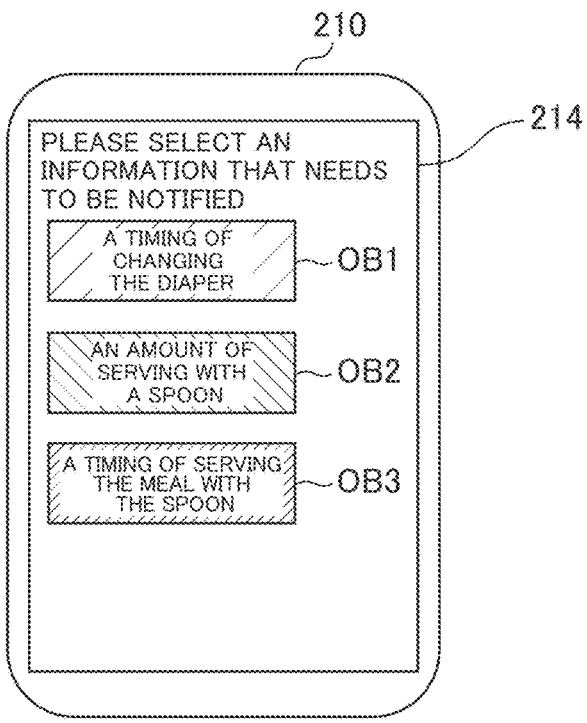
FIG. 17 shows an example of the settings screen.

The FIG. 17 shows an example of a setting screen for setting the support information to be output. The processing described below is realized that, for example, the storage unit 212 of the mobile terminal device 210 stores a Web application program communicating with the server system 100, and the processing unit 211 operates according to the Web application program. For example, displaying a display screen and accepting user operations can be done according to the Web application program by using the display unit 214 or the operation unit 215. In addition, the setting unit 113 of the server system 100 performs processing to generate the display screen, update the display screen or control the database according to the user operation. However, the method of this embodiment is not limited to using a Web application program, and various modifications such as using so-called native applications are possible. Although the FIG. 17 shows an example in which a setting screen is displayed on the display unit 214 of the mobile terminal device 210, the setting screen may be displayed on an another caregiver device 200.

For example, the setting screen is a screen in which "active", "inactive", and "can't output" can be selected for each of the multiple pieces of the support information. The FIG. 17 shows an example of a setting screen that includes objects OB1 to OB3 corresponding to three pieces of the support information: "timing for changing a diaper" which is the support information supporting the assisted excretion, and "serving amount by the spoon" and "serving timing by the spoon" which is the support information supporting the meal assistance.

For example, if the corresponding support information is "active", the object is displayed in the first mode. If the corresponding support information is "inactive", the object is displayed in a second mode. If the corresponding support information can not output, the object is displayed in a third mode. The display mode may be controlled using the size, shape and color of the object, or the size, font, color, etc. of the text included in the object. In addition, the detailed display mode can be modified in various ways.

In the FIG. 17, objects OB1 to OB3 are buttons, and the colors of the buttons are different depending on "active", "inactive", or "can't output". For example, "timing for changing a diaper" is "active", "serving amount by the spoon" is "can't output", and "serving timing by the spoon" is "inactive". In this case, the support information output unit 112 outputs the support information representing "timing for changing a diaper" and does not output the support information representing "serving timing by the spoon". In addition, in the nursing home, since it may be difficult to accurately determine the "serving amount by the spoon" due to a shortage of sensors, the output of "serving amount by the spoon" is not acceptable to output. Since each object OB1~OB3 is displayed in a different manner, it is possible to present the current setting to the caregivers in an easy-to-understand manner.

An operating the operating part 215 of the mobile terminal device 210 by the caregivers can switch "active" or "inactive". For example, when the caregiver performs an operation to select "timing for changing a diaper," information indicating this is transmitted to the server system 100. The setting unit 113 performs processing for updating the output setting corresponding to the "timing for changing a diaper" of the target caregiver ID into "inactive" in the first association information 123. The setting unit 113 also generates a display screen in which the corresponding object OB1 is displayed in the second mode corresponding to the "inactive" one and transmits it to the mobile terminal device 210 via the communication unit 130. The display unit 214 displays the display screen.

Similarly, when an object selection operation corresponding to the inactive support information is performed, the setting unit 113 updates the output setting corresponding to the target caregiver and the target support information into "active". The display unit 214 changes the display mode of the object in which the selection operation has been performed to the first mode.

On the other hand, even if an object selection operation corresponding to the support information that is "can't output" is performed, the display unit 214 maintains the display in the third mode that represents "can't output". In this case, the setting unit 113 does not perform update processing of the first association information 123.

In addition, when an object selection operation corresponding to support information that is "can't output" is performed, the input data necessary for outputting the support information may be suggested. For example, the server system 100 may specify necessary input data based on the second association information 124 and display the input data on the display unit 214 of the mobile terminal device 210. Also, as mentioned above, the input data described above may be replaced by a sensor or a device. For example, the setting unit 113 may identify the sensor or the device required to output the support information for which the selection operation by the user has been performed, and may display the sensor or the device on the display unit 214 of the mobile terminal device 210.

Figure 18:
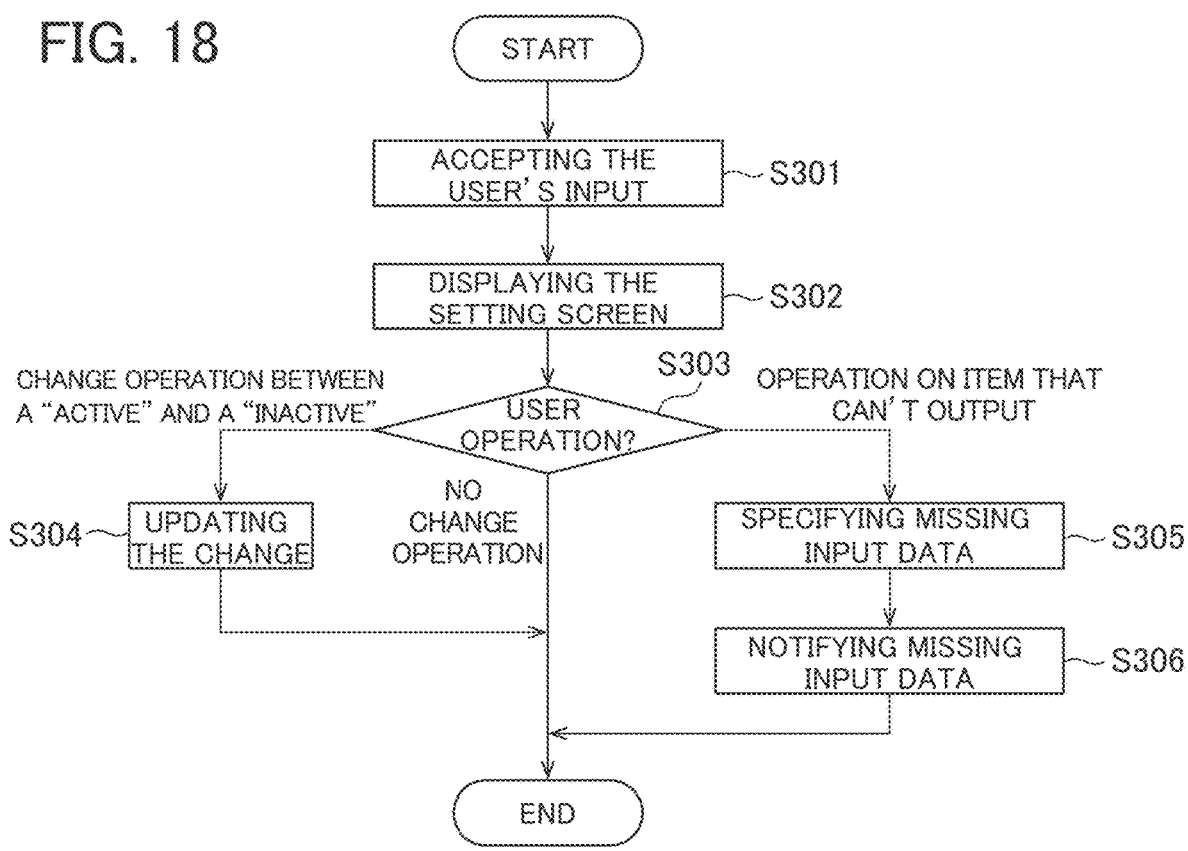
FIG. 18 is a flowchart illustrating a setting process.

The FIG. 18 is a flowchart explaining the above setting process. Firstly, the caregiver performs the setting change operation using his or her caregiver device 200. In the step S301, the setting unit 113 of the server system 100 accepts the setting change operation via the network NW.

In the step S302, the setting unit 113 performs processing to display the setting screen on the caregiver device 200 based on the first association information 123 at that time and the caregiver ID representing the caregiver who performed the setting change operation. The processing in the step S302 may be the processing of creating an image corresponding to the setting screen and transmitting the image to the caregiver device 200, or the processing of transmitting information for generating the setting screen to the caregiver device 200. The information for generating the setting screen may be an extracted result extracted part of the data corresponding to the caregiver ID among the first association information 123. Also, the information for generating the setting screen may be the processing result in which some processing is performed on the extracted result. Thus, for example, a screen corresponding to the FIG. 17 is displayed on the display unit 214 of the mobile terminal device 210.

In the step S303, the setting unit 113 determines the user operation performed by the caregiver device 200. When no operation to change the setting is detected, the setting unit 113 terminates the processing.

In the case that the setting operation to activate the inactive support information is performed, or the setting operation to deactivate the active support information is performed, the setting unit 113 reflects the setting change in the step S304. Specifically, the setting unit 113 performs processing to update the first association information 123 based on the information from the caregiver device 200.

Also, if a selection operation for the support information that is "can't output" is performed, at the step S305, the setting unit 113 identifies the input data, the sensor, or the device that is missing for the output of the support information. In the step S306, the setting unit 113 presents and proposes the identified input data, or the identified sensor, or the identified device to the caregivers. The processing in the step S306 may be processing to transmit the display image itself or processing to transmit information used to generate the display image, similar to the processing in the step S302. The presentation described here is not limited to display, and the presentation processing using the voice or the like may be performed.

3.2.2 Output Processing of the Support Information

Figure 19:
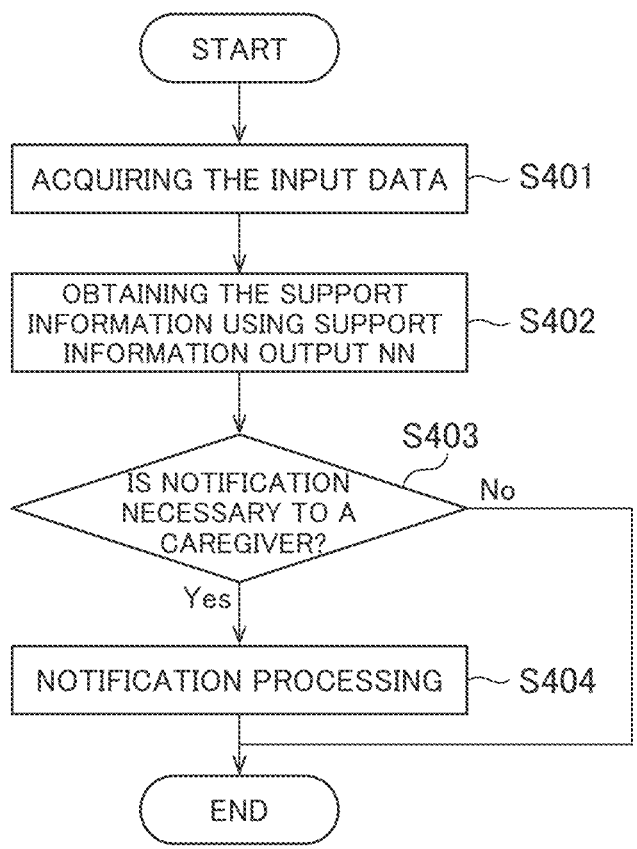
FIG. 19 is a flowchart describing the processing for outputting each support information.

The FIG. 19 is a flowchart illustrating an output processing of the support information by the support information output unit 112. In the step S401, the support information output unit 112 acquires the input data corresponding to the support information to be output. Specifically, the storage unit 120 of the server system 100 stores one or more input data to output the target support information among the multiple input data shown in the FIGS. 28 to 42. The support information is associated with the input data using, for example, the aforementioned second association information 124.

In the step S402, the support information output unit 112 obtains the support information by inputting necessary input data into the support information output NN 122.

In the step S403, the support information output unit 112 determines whether or not a notification based on the support information is necessary. If the notification is necessary, the support information output unit 112 performs the notification processing in the step S404. The notification may be a voice notification using a headset earphone or the like, a display using the display unit 214 of a mobile terminal device 210, or other notification. When the notification is unnecessary or after the notification processing is performed, the support information output unit 112 terminates the processing.

As noted above, the number of the support information items to be output can vary depending on the type of sensors installed in the nursing home and the settings of the caregiver. However, even in both cases, the flow of processing shown in the FIG. 19 for each piece of the support information to be output is the same, the flow of processing includes the identification of the input data, the operation by NN, and the notification if necessary.

If the processing performance of the server system 100 is sufficient, the support information output unit 112 will always perform the processing shown in the FIG. 19 about all the support information set as output targets, and appropriately perform the notification processing about items which need the notification.

Also, considering the reduction of processing load, the processing shown in the FIG. 19 may then be performed about the limited support information which is needed at that time. For example, as shown in the FIGS. 43 to 45, the support information can categorize the needed situations, such as the support information needed for the meal assistance, the support information needed for the excretion assistance, and so on. Accordingly, the support information output unit 112 may identify the necessary support information in the current situation and execute the processing shown in the FIG. 19 for the identified support information. For example, the support information output unit 112 may determine whether the assistance is to be started for the meal assistance, the excretion assistance, and the transferring or moving assistance, respectively. The support information output unit 112 performs the processing shown in the FIG. 19 for the support information related to the assistance determined to be started. The start determination is described later with reference to the FIG. 20.

In addition, in the case of the meal assistance, it is possible to classify the assistance into "the assistance before the meal", "the assistance during the meal", "the assistance after the meal" in chronological order. Therefore, the support information output unit 112 can specify the executed order in which the processing shown in the FIG. 19 among the multiple pieces of the support information. In addition, depending on the assistance, there may be restrictions on the order of execution and the need for execution among the assistance, such as the fact that the second assistance is required only when the first assistance is performed.

Therefore, the support of the assistance by the information processing system 10 of this embodiment may be performed according to assistance sequences that combine a plurality of assistance. Specifically, the assistance of the assisted person by the caregiver is supported by the support information output unit 112 sequentially outputting the multiple support information according to the assistance sequences.

The following describes examples of the assistance sequences for the meal assistance, the excretion assistance, and the transferring or moving assistance. Specifically, the start determination of each assistance sequence is determined firstly, and then the specific flow of each assistance sequence is explained.

As described later with reference to the FIGS. 21 to 23, for the sake of illustrative convenience, only some of the support information in the FIGS. 43 to 45 is output as a target in the following assistance sequence. However, it is easy for those skilled person in the art to understand that in each assistance sequence described below, variations such as omitting the output of some support information or adding the output of other support information shown in FIGS. 43 to 45 are possible.

3.2.3 Start Determination

The assistance in this embodiment may include the meal assistance, the excretion assistance, and the transferring or moving assistance. However, these assistance need not be performed all the time, and the assistance sequence is performed when the assisted person needs the assistance and there exists the caregivers who can perform the assistance. That is, in the present embodiment, the start determination of the assistance sequence is performed firstly, and whether the starting or waiting of the assistance sequence may be determined according to the result of the start determination.

Figure 20:
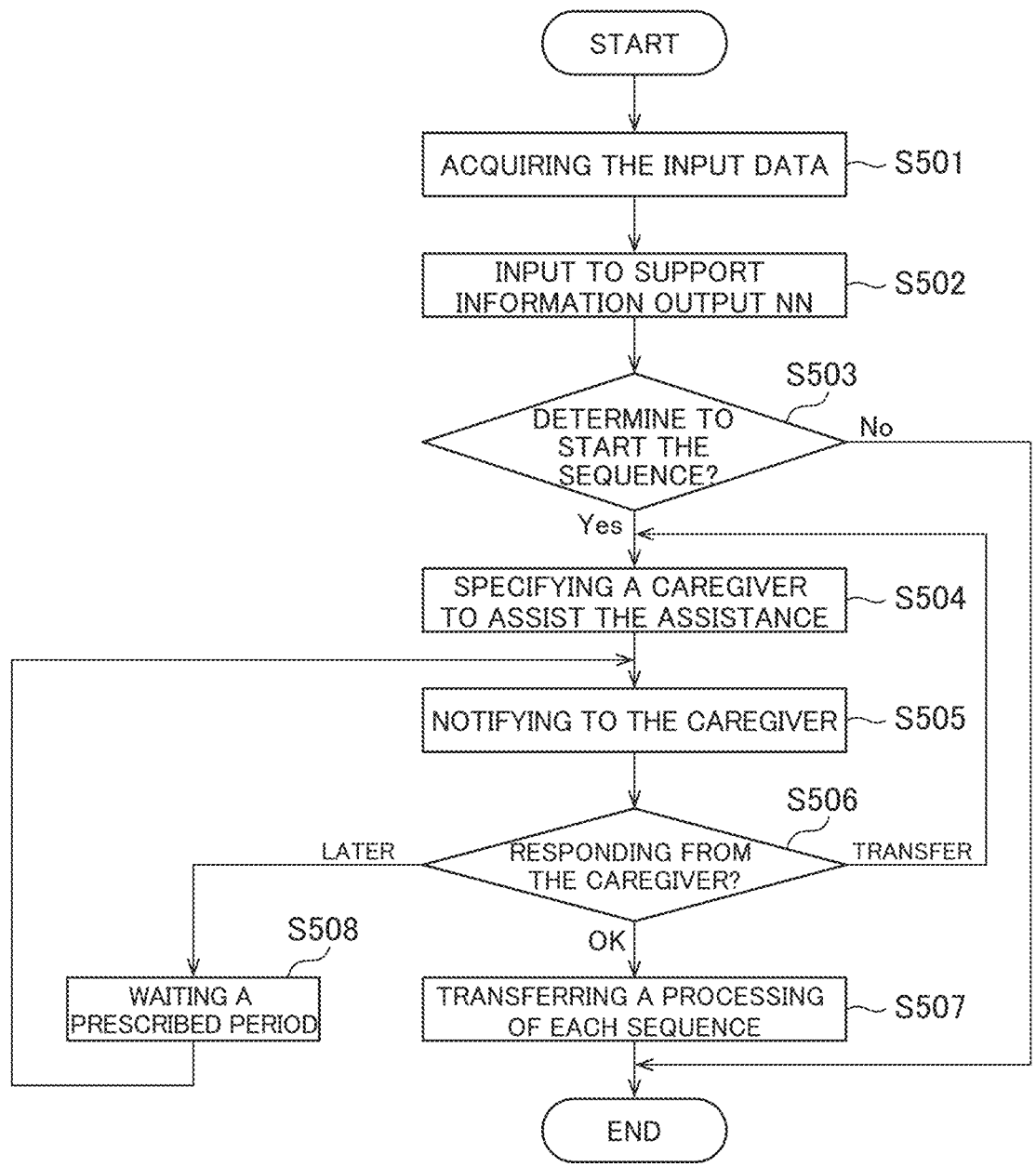
FIG. 20 is a flow chart illustrating a start decision of a assistance sequence.

FIG. 20 is a flow chart to explain the start determination. This process is periodically performed, for example for each assisted person. First, in the step S501, the support information output unit 112 acquires at least a part of the input data shown in FIGS. 28 to 42. In the step S502, the support information output unit 112 obtains the support information by inputting the acquired input data into the support information output NN 122. Here, the support information is the information to identify at least one of the following: a timing to start the meal assistance, a timing to start the excretion assistance, and a timing to start the transferring or moving assistance. For example, the support information output unit 112 may determine whether or not each assistance should be started at the timing when the processing shown in the FIG. 20 is performed. Alternatively, the support information output unit 112 may output the information specifying a detailed time, such as each assistance should be started a certain number of minutes later.

In the step S503, the support information output unit 112 determines whether the current timing would be a timing of the assistance sequence to start. If it is determined that the current timing is not the timing to start, the support information output unit 112 completes the processing and waits again until the processing shown in the FIG. 20 is performed.

For example, the support information output unit 112 determines a timing of the meal assistance sequence to start by using as input data, the complexion of each assisted person, the body temperature of each assisted person, the body weight of each assisted person, the medication of each assisted person, the history of past meals of each assisted person, the history of excretion of each assisted person, the history of rehabilitation of each assisted person, etc., in addition to the information of the meal schedule in the nursing homes.

Also, regarding to the excretion assistance, we consider a case that roughly schedules such as five times a day are decided. Therefore, the support information output unit 112 determines a timing of the excretion assistance sequence to start by using as input data, the amount and timing of meals for each assisted person, the amount and timing of water intake, whether or not laxatives have been administered, the past history of the excretion, the rehabilitation record, the pressure ulcer condition, etc., in addition to the information of the excretion assistance schedule in the nursing home.

Also, the support information output unit 112 determines a timing of the assistance sequence related to the transferring or moving assistance to start by using as the input data, the ADL of the assisted person, the medical history of the assisted person, etc., in addition to whether the events requiring the transfer of the assisted person would occur, such as the meals and the recreation.

When it is determined that the current timing is the timing of the assistance sequence to start, in the step S504, the support information output unit 112 performs processing to determine a caregiver to assist a target assisted person. For example, the support information output unit 112 holds the information such as the work schedule of the caregivers in the nursing home and the assignment of the assisted person, and may designate a caregiver based on that information.

In the step S505, the support information output unit 112 performs the notification processing to instruct the start of the assistance sequence to the caregiver device 200 of the designated caregiver. For example, the support information output unit 112 may perform the processing to reproduce a voice such as "Please start the meal assistance for Mr. A" in wearable device 220 such as a headset. The support information output unit 112 may also perform the processing to display the same text on the display unit 214 of the mobile terminal device 210.

In the step S506, the support information output unit 112 determines the response of the caregiver to the above notification processing. For example, three responses may be set: "OK," "later" and "transfer" as the response of the caregiver. The caregiver may respond by voice. The caregiver's response may be obtained based on detection results using the microphone on the headset, for example. The caregiver's response may also be realized by other ways such as the text input.

A "OK" means a response indicating that the instructed assistance sequence can be started. In this case, in the step S507, the support information output unit 112 transfers to a detailed assistance sequence. For example, the support information output unit 112 starts the processing of the FIG. 21, FIG. 22, and FIG. 23, etc.

A "Later" is a response indicating that the assistance sequence can not be started immediately, but is considered ready to start after a prescribed period of time. For example, it may be the case that the caregiver is currently engaged in another task, but the instructed assistance sequence can be started once the task is completed. In this case, in the step S508, the support information output unit 112 waits for a prescribed time, and after waiting, returns to the step S505 and executes the notification processing to the same caregiver again.

A "transfer" is a response indicating that it is difficult for the caregiver to perform an assistance sequence and the caregiver asks for a request to an another caregiver. In this case, the support information output unit 112 returns to the step S504 and select an another caregiver. The processing after the step S505 is the same.

However, a processing when "transfer" is selected is not limited to this. For example, if the designated caregiver selects "transfer," the support information output unit 112 may simultaneously notify notifications to multiple caregivers. Then, among the multiple caregivers, the caregivers who responded "OK" may be selected and the specific assistance sequence may be started for the caregivers.

3.2.4 The Meal Assistance

Figure 21:
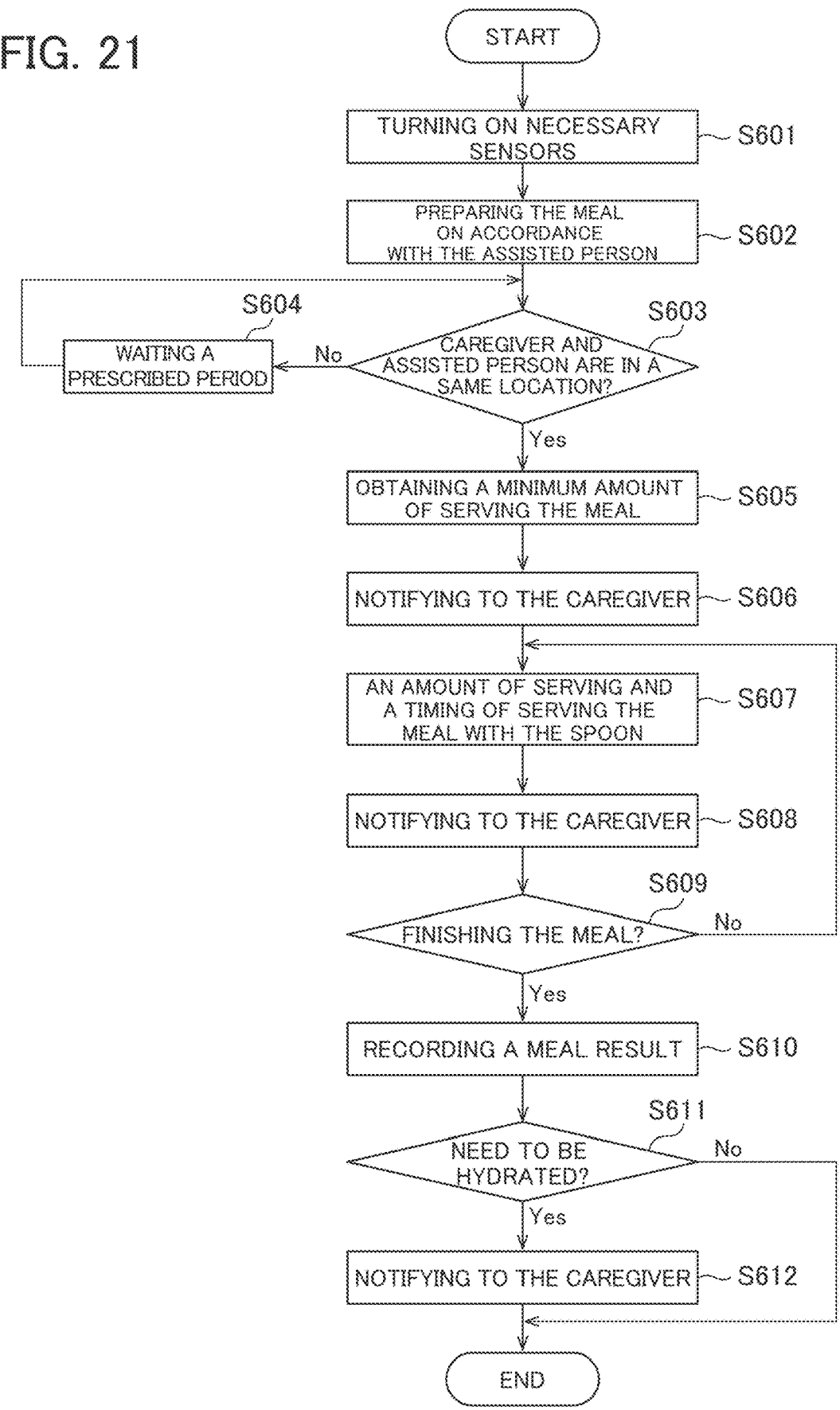
FIG. 21 is a flow chart illustrating a meal assistance sequence.

FIG. 21 is a flowchart illustrating a detailed assistance sequence when the meal assistance is provided.

Firstly, when the meal assistance sequence is started, in the step S601, the support information output unit 112 controls to turn on the sensors necessary for the meal assistance support among the sensor groups 400 arranged in the nursing home, etc. In the step S601, the support information output unit 112 may remotely control to switch "on" or "off" of the sensors in the sensor group 400. Or the support information output unit 112 may designate a sensor or a device and send a message to a device in a nursing home such as the caregiver device 200 to make the caregiver turn on the sensor or the device. Although this is not explicitly shown in the flowchart, the sensor group 400 periodically transmits the sensor information to the server system 100, and the support information output unit 112 can acquire the input data necessary for outputting the support information.

In the step S602, the support information output unit 112 outputs the support information for providing the meals according to the assisted person based on the support information output NN 122. For example, in the step S602, the support information output unit 112 outputs the support information to instruct the meal according to the allergy of the assisted person and the medication according to the medical condition.

Next, in the step S603, the support information output unit 112 determines whether the assisted person and the caregiver have moved to a position where the assisted person will eat. The Meals may be served in the assisted person's room or in the dining room. The processing in the step S603 is performed by taking as input data, the information that can identify the location of the assisted person and the caregiver using a camera or radio frequency identifier (RFID) etc. In the processing of the step S603, for example, the support information output unit 112 may determine that the assisted person and the caregiver have moved to the position where the assisted person eat if the image of the assisted person and the meal is captured on the screen of the camera carried by the caregiver.

If at least one of the assisted person and the caregiver is not in the position, in the step S604, the support information output unit 112 waits for a certain time and then performs the processing of the step S603 again.

If the assisted person and the caregiver are in position, in the step S605, the support information output unit 112 obtains the minimum amount of the meal to eat. The minimum amount to eat here may be less than the amount of the served meal. In other words, the caregiver does not have to feed all the served meals and does not have to force the assisted person to eat more once the minimum amount is reached. In the processing of the step S605 is performed using, as the input data, the assisted person's complexion, the care record of the assisted person, the weight change of the assisted person, the meal schedule of the assisted person, etc.

In the step S606, the support information output unit 112 notifies the caregiver of the required minimum amount to eat. The notification may be audible notification using earphones such as a headset, or may be displayed using the display unit 214 of a mobile terminal device 210.

In the step S607, the support information output unit 112 determines a timing of serving a meal with a spoon and the amount served with the spoon.

The timing of serving a meal with a spoon represents the timing when one bite amount of the meal on the spoon is fed into the assisted person's mouth. The amount served with the spoon represents one bite amount of the meal. The processing of the step S607 is performed, for example, by using the input data related to the chewing state of the assisted person. The input data related to the chewing state is, for example, the information on the condition of the mouth of the assisted person, the condition of the throat of the assisted person, the facial expression of the assisted person, the complexion of the assisted person, the posture of the assisted person, the changes of the meal in response to a talk, the timing of swallowing of the assisted person, a time period of putting the meal in his or her mouth of the assisted person, the eating rhythm of the assisted person, etc., and may be, for example, an imaged image of the assisted person. In addition, the input data related to the chewing state is the information related to the movement of the jaw, the movement of the cheek, the movement of the whole face, and the movement of the body, and may be the sensor information of the motion sensor 410, for example. In addition, the input data related to the chewing state may include a voice data indicating the quality of voice and volume of voice in response to a talk or the like during a meal eating, and the information indicating the difference in a timing and an amount during the meal eating in the past, as well as a seasonal difference and the difference of the physical conditions. The information representing the eating rhythm may be an imaged image or the sensor information of the motion sensor 410. In addition, the sensors used to acquire the above information can be modified in various ways.

In the step S608, the support information output unit 112 informs the caregiver of the timing of serving the meal with the obtained spoon and the amount served with the spoon.

For example, in the step S607, the support information output unit 112 determines whether the current timing is the timing of serving a meal with a spoon. If it is determined that the current time the timing of serving a meal with a spoon, the support information output unit 112 notifies that in the step S608 and if it is determined the current time is not the timing of serving a meal with a spoon, the support information output unit 112 doesn't notify that in the step S608. In addition, in the case that it is determined that the current timing is not the timing of serving, the support information output unit 112 may report that the current timing is not the timing of serving when the caregiver intends to provide the meal to the assisted person.

Also, when it is determined that current timing is the timing of serving, for example, the support information output unit 112 may obtain the amount served with the spoon in the step S607 and inform the caregiver of the requested amount in the step S608 using the number of grams or a step such as "more", "less", or "normal". Alternatively, in the step S607, the support information output unit 112 may obtain the support information representing whether the amount served with the spoon is appropriate by using the input data representing the meal amount actually placed on the spoon by the caregiver. The input data in this case includes, for example, the output of a camera that images the hand of the caregiver. If the meal amount served with the spoon is too much or too little, in the step S608, the support information output unit 112 may issue a notification urging to change the meal amount served with the spoon.

The facial expression of the assisted person may be used to determine whether the assistance of the assisted person is correct. For example, the support information output unit 112 may not output the instruction specifically as a correct answer when the assisted person is smiling, but may output the instruction when the assisted person has an displeased face. For example, the support information output unit 112 may use, as input data in the step S607, an image imaged the face of the assisted person or the result of the facial expression determination processing based on the image. In this way, based on the facial expression of the assisted person, it can be determined whether the pace of the meal serving is appropriate. Alternatively, the support information output unit 112 may determine the degree of relaxation from the heart rate (pulse) analysis. The support information output unit 112 may not output instructions specifically as correct answers when the degree of relaxation of the assisted person is high, and may output instructions when the degree of relaxation of the assisted person is low. For example, the support information output unit 112 uses the information representing the heart rate, the pulse rate, or their analysis results as the input data in the step S607. Also, the steps other than S607 in the FIG. 21, the FIGS. 22 and 23, which will be described later, may use that the facial expression and degrees of relaxation may be applied in determining whether the assistance is appropriate or not.

In the step S609, the support information output unit 112 determines whether or not the assisted person finishes eating the meal. If not, the support information output unit 112 returns to the step S607. By repeating the processing of the steps S607 and S608 in this way, it becomes possible to present to the caregiver the timing of serving one bite of the meal and the amount of the meal to be served at that time, piece by piece. As a result, it is possible for the assisted person to eat the meal at an appropriate pace.

When it is determined that the meal is finished, in the step S610, the support information output unit 112 instructs the recording of the meal result. For example, as the meal result, an image including the leftover of the meal is acquired. It should be noted that the recording instruction may be one that instructs the caregiver to take an image using a mobile terminal device 210 or the like, or it may be one that automatically takes an image by remotely controlling a camera placed at an appropriate position.

In the step S611, the support information output unit 112 obtains the support information indicating whether the assisted person needs to be hydrated. When the hydration is necessary, in the step S612, the support information output unit 112 notifies the caregiver to instruct the hydration. The support information output unit 112 may obtain the support information representing a detailed amount of the replenishment of the hydration in the step S611 and report the amount of the replenishment of the hydration in the step S612.

If hydration is not necessary, or after performing the processing of the step S612, the meal assistance sequence is completed.

FIG. 21 is an example of a meal assistance sequence, and the detailed sequence allows various modifications to be performed. For example, when the meal assistance is provided in a nursing bed 310, a control processing to switch a meal mode suitable for the meal at the nursing bed 310 (e.g., a mode in which the back bottom is raised to a set angle in the range of 30 to 90 degrees, a mode in which the knee bottom is raised to a set angle in the range of 0 to 30 degrees, a mode in which the foot bottom is lowered to a set angle in the range of 0 to 90 degrees, a bed tilt angle to a set angle ranging from 0 degrees to 20 degrees so that the head is higher) may be added. For example, the support information output unit 112 may request the support information indicating whether the assisted person and the served meal are in a suitable condition for starting the meal by using the output of a camera or the like as the input data. When it is determined that the assisted person and the served meal is set appropriately, the support information output unit 112 performs a notification processing to ask the caregivers whether it is acceptable to move the nursing bed 310. The nursing bed 310 may be changed to a meal mode if the caregiver responds "OK".

In addition, the support information output unit 112 can output various support information related to the meal assistance for an assistant or a chef who is in charge of cooking until the meal is served in the dining area.

3.2.5 The Excretion Assistance

Figure 22:
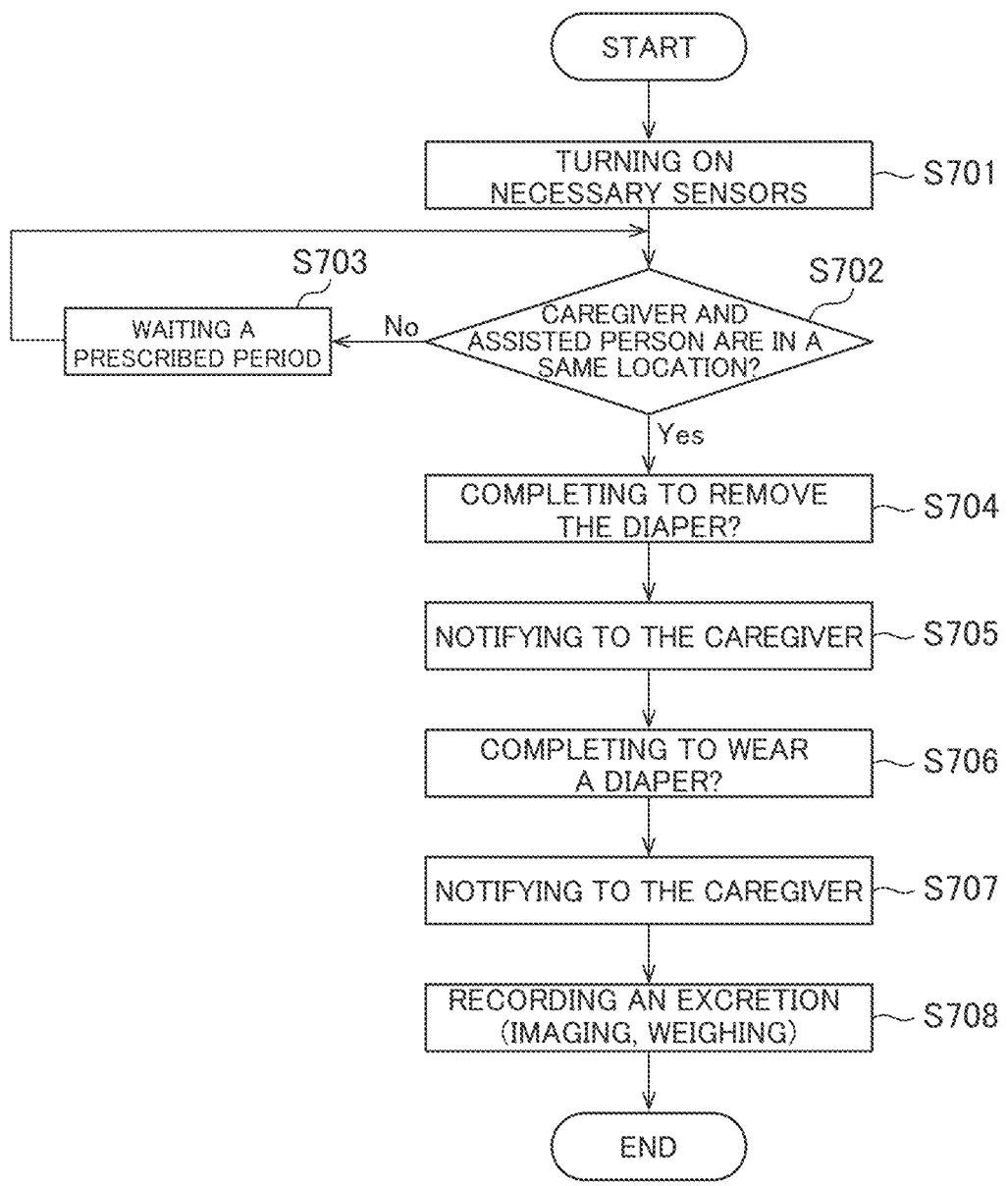
FIG. 22 is a flow chart illustrating a excretion assistance sequence.

FIG. 22 is a flowchart illustrating the detailed assistance sequence when the excretion assistance is done. When the excretion assistance sequence is started, in the step S701, the support information output unit 112 controls to turn on the sensors necessary for the excretion assistance among the sensor groups 400 arranged in the nursing home, etc.

Next, in the step S702, the support information output unit 112 determines whether the caregiver has moved to a position to assist excretion. For example, if the assisted person excretes into a diaper on the nursing bed 310, the excretion assistance is assumed to be done in the assisted person's room. In this case, the processing of the step S702 is carried out by taking as input data, for example, the output of a camera arranged in a living room or the output of a camera of a mobile terminal device 210 carried by a caregiver, the output of RFID, etc.

When the caregiver is not in the position, in the step S703, the support information output unit 112 waits for a prescribed time period and then performs the processing of the step S702 again. When the caregiver is in the position, in the step S704, the support information output unit 112 requests the support information regarding to remove the diaper. In the step S705, the support information output unit 112 notifies the requested support information.

For example, when removing the diaper, if the posture of the assisted person, the posture of the caregiver, the direction in which the diaper is removed, etc. are not appropriate, it is not desirable that feces adhere to the clothes and sheets of the assisted person. Therefore, the support information output unit 112 may determine, for example, in the step S704, whether the movement of the caregiver in removing the diaper is appropriate. For example, the support information output unit 112 may acquire the motion that is the correct answer and compare the motion with the actual motion of the caregiver. If it is determined to be inappropriate, in the step S705, the support information output unit 112 may notify that it is inappropriate or may concretely instruct the appropriate movement.

In the step S706, the support information output unit 112 requests the support information related to how to wear the diaper. In the step S707, the support information unit 112 performs a notification processing of the requested support information.

The support information output unit 112 may determine, for example, in the step S706, whether the movement of the caregiver when putting on the new diaper is appropriate. For example, the support information output unit 112 may acquire the motion that is the correct answer and compare the motion with the actual motion of the caregiver. If it is determined to be inappropriate, in the step S707, the support information output unit 112 may notify that it is inappropriate or may concretely instruct the appropriate movement.

It is true there is a problem that the sheets, etc., get dirty when the diaper is removed, but it is easy for the caregiver to recognize the dirt and to deal with it relatively easily because the caregiver is by his or her side. On the other hand, in the case of a fecal leak due to inadequate and inappropriate wearing, there is not always the caregivers nearby at the time of the fecal leak. In addition, considering the burden on caregivers, it is not easy to excessively increase the frequency of excretion assistance, and there is a risk that fecal leakage may be left for a long time. In view of the above, the support information output unit 112 may set conditions so that the notification in the processing of the step S707 becomes easy to perform compared to the processing of the step S705. For example, the threshold in the step S707 is set to be smaller than the threshold in the step S705 in the case that the notification in the steps S705 and S707 is performed if the degree of divergence between the correct answer and the actual movement exceeds the threshold.

Alternatively, in the step S706, it may be determined in detail whether the wearing condition is appropriate by using the sensor information of the sensor provided on the diaper as the input data. Again, it is possible to have them provide the assistance with a greater emphasis on wearing diapers.

In the step S708, the support information output unit 112 instructs the recording of the excretion state. Specifically, the support information output unit 112 gives an instruction to take an image about the state of the urine and the stool and an instruction to measure the weight of the urine and the stool. The weight measurement may be the weight measurement of the diapers or the weight measurement of the garbage if the garbage is to be transported. The instructions for recording here may be to have the caregivers perform imaging and weighing, or to remotely control the camera or the sensor.

FIG. 22 is an example of the excretion assistance sequence, and the detailed sequence can perform various modifications. For example, when the excretion assistance is done on the nursing bed 310, a control processing to change the height of the nursing bed 310 to a height suitable for the excretion assistance (For example, the height from the floor to the top of the bottom is 50 mm to 100 mm without the need for the caregiver to bend over) may be added. For example, in the case that the caregiver responds "OK" in the step S506 in the FIG. 20, a state in which the caregiver can easily assist with excretion is realized by changing the height of the nursing bed 310 when the caregiver arrives. If the nursing bed 310 has a speaker, the support information output unit 112 may be controlled to output a voice to explain the purpose to the assisted person before changing the height. The support information output unit 112 may also inform the caregiver that the height of the nursing bed 310 has been changed.

3.2.6 The Transferring or Moving Assistance

Figure 23:
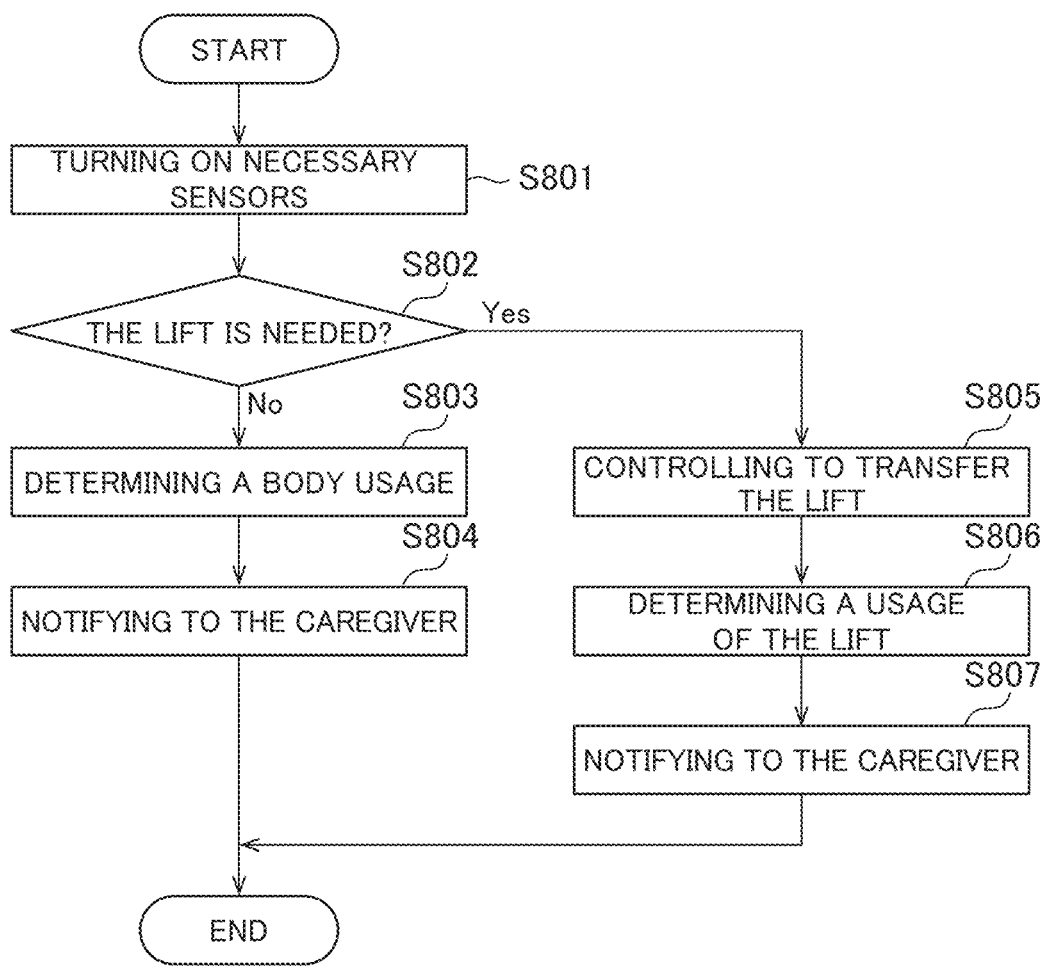
FIG. 23 is a flow chart illustrating a transfer assistance sequence.

FIG. 23 is a flowchart illustrating the detailed assistance sequence when the transferring or moving assistance is performed. When the transferring or moving assistance sequence is started, in the step S801, the support information output unit 112 controls to turn on the sensor necessary for the support of the transferring or moving assistance among the sensor groups 400 arranged in the nursing home, etc.

Next, in the step S802, the support information output unit 112 determines whether a lift is necessary for the transferring or moving assistance of the assisted person. The processing in the step S802 is performed by taking as input data the body size difference between the caregiver and the assisted person, the ADL of the assisted person, the time required for transferring or moving, the inventory of lifts in the nursing home, etc.

If the lift is not required, the caregiver would manually transfer the assisted person to the wheelchair. In the step S803, the support information output unit 112 obtains the support information about the transferring by manual. In the step S804, the support information output unit 112 performs the notification processing of the obtained support information. Note that the support information output unit 112 may issue a notification asking the caregiver whether the wheelchair needs to be locked before transferring. When the caregiver answers that it is necessary, the support information output unit 112 controls to lock the wheelchair. Alternatively, the support information output unit 112 may automatically determine whether the lock is necessary, and if it is determined to be necessary, instruct the caregiver to lock the wheelchair before the processing of the step S803.

The support information output unit 112 may determine, for example, in the step S803, whether the usage of the caregiver's body in transferring by manual is appropriate. For example, the support information output unit 112 may acquire the correct movements, such as the posture of the caregiver, the position in which the assisted person is placed on the foot, and compare the correct movements with the actual movements of the caregiver. The caregiver's movements may be detected using the motion sensor 410 or the imaging sensor 420. In addition to the movement of the caregiver, these sensors may also detect the movement and posture of the assisted person, because the positional relationship between the assisted person and the caregiver is important in the transferring or moving assistance. If it is determined to be inappropriate, in the step S804, the support information output unit 112 may notify that it is inappropriate or may concretely instruct the appropriate movement.

If a lift is required, in the step S805, the support information output unit 112 controls to move the lift to the location of the assisted person. In the step S806, the support information output unit 112 obtains the support information relate to the transfer using the lift. In the step S807, the support information output unit 112 performs a notification processing of the obtained support information.

The support information output unit 112 may determine, for example, in the step S806, whether a usage of the lift is appropriate. For example, a support information output unit 112 may acquire correct answer data, such as the wearing state of a sling that can safely hoist the assisted person, and compare the correct answer with the actual state. If it is determined to be inappropriate, in the step S807, the support information output unit 112 may notify that it is inappropriate, or may concretely indicate the appropriate wearing condition.

After lifting the assisted person up by the lift, he or she may sit in a wheelchair, or may be moved as is. The support information output unit 112 may determine which option is used in consideration of the inventory of the lift, the transfer destination, and the condition of the assisted person, and notify it to the caregivers.

FIG. 23 is an example of a transferring or moving assistance sequence, in which various modifications can be performed. For example, a control may be added to change the height of the nursing bed 310 (For example, a nursing bed has a height from the floor to the top of the bottom; a height which feet are firmly attached when sitting on the bed 200 mm to 500 mm for an assisted person who is able to stand, a height which is slightly higher than the wheelchair when transferring to the wheelchair 200 mm to 500 mm, and a height which is slightly lower than a wheelchair when transferring from the wheelchair to the bed 200 mm to 500 mm, etc.) to a height suitable for the transferring or moving assistance. Since the detailed control is the same as for the excretion assistance etc., the detailed explanation is omitted.

3.2.7 Detailed Changes in the Assistance in Response to the Factors

The detailed sequence of the meal assistance, the excretion assistance, and the transferring or moving assistance has been explained above. Although the explanation is omitted in the FIGS. 21 to 23, each support information may be obtained based on the presence or absence of the abnormal behavior or the factors of abnormal behavior. For example, as described above using the FIG. 13, the presence or absence of the abnormal behavior and the factor determination result of the abnormal behavior are used as input data when obtaining support information.

For example, if the factor determination unit 111 determines dementia as a factor, the support information output unit 112 change the output in each assistance sequence as if the dementia were progressing.

For example, in the meal assistance, the support information output unit 112 outputs the information indicating the amount of the meal served per one bite (the amount served with a spoon) and the information indicating the timing of serving a meal for one bite (timing of serving a meal with a spoon) as the support information. In this case, the support information output unit 112 may change at least one of the amount and the timing of serving when the behavior is determined to be the abnormal behavior of the dementia factor, compared with when the behavior is determined not to be the abnormal behavior of the dementia factor. In this way, it will be possible to change the pace of serving the meals appropriately between the assisted person who has the dementia and the assisted person who does not have the dementia. For example, the support information output unit 112 may provide a smaller amount or a slower timing of serving. In this way, the pace of serving the meals can be appropriately managed when the dementia makes the assisted person more likely to choke.

In addition, the support information output unit 112 outputs, as the support information, the information specifying the timing of the excretion assistance to start, which is the timing to start the excretion assistance. In this case, if the behavior is determined to be an abnormal behavior caused by the dementia factor, the timing of the excretion assistance to start may be changed compared to when the behavior is determined not to be an abnormal behavior caused by the dementia factor. In this way, it would be possible to initiate the excretion assistance sequence at the appropriate time, depending on whether the person has the dementia or not. For example, the support information output unit 112 may make the timing of the excretion assistance to start earlier by adjusting the timing of the excretion assistance to start in this way, it is possible to make it easier to keep a clean state even when the dementia makes it difficult for the assisted person to control the timing of the excretion.

Otherwise, if it is determined to be an abnormal behavior due to the factors of the dementia, the support information output unit 112 may change the support information to provide the following meal assistance. For example, the support information output unit 112 sets a high priority for the following notifications when it is determined to be an abnormal behavior caused by the dementia. For example, the support information output unit 112 notifies the following notifications in the case of a dementia factor, and does not notify the following notifications in the case that there is no abnormal behavior or in the case of other factors except for the dementia factor. Or the support information output unit 112 notifies the following notifications regardless of whether or not the factor of dementia is existed, but may control to make the notifications more likely to notify when the factor of dementia is existed. For example, the support information output unit 112 may increase the notification frequency in case of the dementia-related factors, or it may relax conditions in determining the need for the notifications.

defecating before a meal so as to devote oneself to the
       meal notifications whether the assisted person is getting enough sleep or feeling well after serving the meal, the caregivers make the observations without any assistance to understand today's situation setting up the environment, preparing dishes to make the assisted person calm down, and preparing dishes he or she love shaping into an easy-to-eat posture making the adjustments, such as shifting a timing of serving the meal if the assisted person do not eat the meal more talking to them to understand that it is a meal and assisting them for the first bite talking to them and teaching them how to eat hydrating so as not to dehydrate Adjusting the amount served with a spoon and the pace at which they eat to avoid choking Increasing the amount of activity if they do not eat the meal more, or adjusting the rhythm of the life Also, if it is determined to be an abnormal behavior caused by the dementia, the support information output unit 112 may modify the support information to provide the excretion assistance as follows:

notifications whether the assisted person is getting enough sleep or feeling well selecting and using appropriate pants, diapers, pads, etc.

In case of the toilet defecation, making sure water is flushed in the toilet.

Taking countermeasures against falling because the assisted person may go to the bathroom more often Watching the timing of his or her excretion and talk to guide the assisted person to the toilet Watching the timing of his or her excretion to guide the assisted person to the toilet or to change diapers because there is a possibility of coprophilia.

assigning the compatible caregiver

Also, the support information output unit 112 may output the support information related to sleep assistance. If it is determined that the behavior is abnormal due to a dementia factor, the support information output unit 112 may change the support information to provide the sleep assistance as follows.

Adjusting rhythm his or her life to keep his or her autonomic nerves healthy

Exercising to increase the amount of activity during the day watching for the abnormal behavior at night When monitoring at night, for example, the sensor information of a sensor to detect whether the assisted person is in the nursing bed or a monitoring sensor is used as the input data.

For example, the support information output unit 112 instructs the caregiver who does not provide the meal assistance for breakfast to install the sensor during breakfast. In the case of performing the exercise, the support information output unit 112 may inform the caregiver to suggest the recreation or the rehabilitation after assisting the excretion of the assisted person in the daytime, for example.

As described above with the reference to the FIG. 6, the factor determination unit 111 may determines whether there is an environmental factor or an excretory disturbance factor as the factors of the abnormal behavior. For example, if it is determined that the behavior is abnormal due to an excretory disorder factor, the support information output unit 112 may change the support information to provide the following assistance.

notifying of the addition of laxatives to serve the dinner changing the contents of the meal (applicable to breakfast, lunch, and dinner)

instructing to provide water after eating the meals suggesting the recreation and the rehabilitation after the excretion assistance in the daytime The support information output unit 112 may not only instruct the addition of laxative but also suggest a specific type of laxative and dosing time. For example, the support information output unit 112 may notify the type of laxative by using the information indicating how many consecutive days the laxative is administered, the information about the defecation interval, etc., as input data. In addition, the support information output unit 112 may instruct the caregiver to remove the sensors other than the excretion sensor among the sensors arranged to respond to the dementia when the assisted person determined to be caused by the dementia is subsequently determined to be caused by impaired excretion.

Also, if it is determined that the behavior is abnormal due to the environmental factors, the support information output unit 112 may modify the support information so as to provide the following assistance:

automatically rhythms controlling of the speakers or the lighting so as to match previous environmental data without the environmental factors.

By approaching the environment same as the previous environment before the abnormal behavior occurred in this way, it becomes possible to arrange the life rhythm of the assisted person. The caregiver may be able to change the settings, such as temporarily stopping the application of automatically controlling or not applying automatically controlling. In addition, the support information output unit 112 may instruct the caregiver to remove the arranged sensor to respond to the dementia when the assisted person had determined to have caused the dementia is subsequently determined to have caused the environment.

Also, if the behavior is determined to be a factor of dementia, the support information output unit 112 may increase the type of the support information to be output in comparison with the case in which the abnormal behavior is not detected. For example, the above support information for "setting up the environment, preparing dishes to make the assisted person calm down, and preparing dishes he or she love" is output when it is determined to be a dementia factor, but the above support information may not output when it is determined to be other factors. In this case, for example, the input data of a temperature sensor, a humidity sensor, a illuminance sensor, and a barometric pressure sensor may be used to determine a favorable environment for the assisted person.

Therefore, when the behavior is determined to be a factor of the dementia the support information output unit 112 is designed to increase the type of the sensor information in comparison with the case in which abnormal behavior is not detected. In this way, since the variety of input data increases, and it becomes possible to obtain the accurately support information for providing the appropriate assistance for the dementia.

Also, the support information output unit 112 may determine whether the newly sensors should be added based on the information to identify one or more sensors that can be used and the sensor information to be added if the behavior is determined to be a dementia factor. Here, the one or more sensors that can be used are specifically located in the target nursing home and are identified based on the third association information 125 in the FIG. 16. As described above using the FIGS. 14 to 16, it is possible not to output the prescribed support information with sufficient accuracy due to some types of sensors deployed in nursing homes, and such support information may be set to "can't output". Therefore, it may be difficult to appropriately output the support information which is suitable for the dementia in some nursing homes even if the factor determination unit 111 determines that dementia is a factor. The information processing device may, for example, determine whether or not the additional sensors are needed and may suggest the additional sensors or the devices including such sensors. In this way, it is possible to output the support information appropriate to the factors.

As described above, it is assumed that appropriate assistance will vary depending on the presence or absence of abnormal behavior and the factors contributing to the abnormal behavior. According to the method of this embodiment, the factor determination result of the behavior of the assisted person is used when supporting the assistance by the caregivers. As a result, it is possible to have the caregiver provide the assistance that is more appropriate for the assisted person.

Specifically, it is possible to convert the tacit knowledge of a skilled caregiver into data and have a less-skilled caregiver provide the appropriate assistance. For example, a less-skilled caregiver can assist as well as an experienced caregiver, improving reproducibility of the assistance. In addition, since variation in care assistance skills is suppressed and the organizational management is facilitated, incidents such as the falling of the assisted person are suppressed. As a result, the occurrence of vacancies associated with hospitalization and the occurrence of overtime associated with the preparation of accident reports can be reduced. Curbing the incidents also curbs caregivers from becoming too risk-sensitive, which can reduce the stress and consequently reduce to leave a job. In addition, that will also improve the satisfaction of the caregivers and their families and improve their quality of life by enabling caregivers to improve their skills and work environment.

The part or most of the processing of the information processing system 10 of this embodiment, the server system 100 of this embodiment, the caregiver device 200 of this embodiment, etc., may be realized by a program. In this case, a processor such as a CPU executes a program to realize the information processing system 10 of this embodiment or the like. In detail, the program stored in the non-transitory information storage medium is read, and the read program is executed by a processor such as a CPU. Here, an information storage medium (a medium that can be read by a computer) stores programs, data, etc., and its function can be realized by an optical disk, HDD, memory (Card type memory, ROM, etc.), etc. A processor such as a CPU performs various processes of the present embodiment based on a program stored in an information storage medium. That is, a program for making the computer function as a part of this embodiment is stored in the information storage medium.

Also, the method of the present embodiment can be applied to an information processing method that determines whether the behavior of the assisted person is an abnormal behavior of the dementia factor based on (1) the information on the dementia level of the assisted person and (2) at least one of the environmental information, the excretion information, and the sleep information of the assisted person, and outputs the support information to support the assistance of the assisted person by the caregivers based on the determination result and the sensor information that is a sensing result about the caregivers who assist the assisted person or the assisted person.

4 Example of Modification

<The Parallel Processing of Multiple Assistance Sequences>

Each assistance sequence described above in the FIGS. 21 to 23 may be performed sequentially. For example, a designated caregiver performs a sequence corresponding to any of the FIGS. 21 to 23 by responding "OK" in the step S506 of the FIG. 20 in a standby state, and returns to a standby state after completion. The standby state refers to a condition in which the targeted caregiver has not performed any of the assistance sequences. Then, again, by responding "OK" in the step S506, the sequence corresponding to any of the FIGS. 21 to 23 is performed.

However, in the nursing homes, etc., one caregiver may assist several assisted persons in parallel. For example, one caregiver simultaneously performs the meal assistance for the assisted person A and the meal assistance for the assisted person B while the assisted person A and the assisted person B are seated in close positions. In this case, it is inefficient that the meal assistance sequence of FIG. 21 for the assisted person B is performed after completing the meal assistance sequence of FIG. 21 for the assisted person A.

Thus, the support information output unit 112 may be able to execute multiple assistance sequences in parallel with respect to one caregiver. For example, in the above example, the support information output unit 112 executes the meal assistance sequence for the assisted person A and the meal assistance sequence for the assisted person B in parallel. In this example, the ration of the caregiver and the assisted person are 1:2, but the number of assisted persons in charge of one caregiver at the same time may be three or more.

For example, the support information output unit 112 performs the processing of the step S605 in the meal assistance sequence of the assisted person A, and notifies the result in a form such as "The minimum amount served for Mr. A is x grams" in the step S606. Similarly, in the meal assistance sequence of the assisted person B, the processing of the step S605 is performed, and the result is reported in a form such as "The minimum amount served for Mr. B is y grams" in the step S606. In this way, the support information output unit 112 acquires the input data concerning the assisted person A and the input data concerning the assisted person B in parallel, and outputs the support information concerning the assisted person A and outputs the support information concerning the assisted person B at necessary timing based on the respective input data. In this way, even if there is a one-to-many relationship between the caregiver and the assisted person, it is possible to have the caregiver perform the necessary assistance for each assisted person. By installing a wide-angle camera capable of simultaneously imaging multiple assisted persons, it is also possible to share the input data concerning the assisted person A with the input data concerning the assisted person B.

However, since there is only one caregiver, it is not easy to respond to all support information, if multiple support information is notified at very close timing.

For example, when the notification for the assisted person A in the step S608 is notified, the caregiver picks up a spoon with meal of the amount according to the notification and carries the meal to the mouth of the assisted person A. If the notification of the step S608 is notified for the assisted person B before completing, it is difficult for the caregiver to take the assisted person B's meal with a spoon and carry it to the assisted person B's mouth.

Additionally, when providing the meal assistance to more than one assisted person, it is more efficient to let the assisted person eat the meal after everyone has gathered at a dining area such as a dining room. Therefore, even if it is determined that the caregiver and the assisted person A are in the same position (Yes in the step S603), there may be undesirable cases to start the processing such as the steps S607 to S609 for the assisted person A when the assisted person B is not in the same position.

In view of these, the support information output unit 112 may not simply perform the assistance sequence for the multiple assisted persons in parallel, but may also perform the processing considering the relationship between the multiple assistance sequences. For example, when multiple assistance sequences are performed in parallel for the designated caregiver, the support information output unit 112 may control the execution and the stop (suspend) of each assistance sequence.

For example, the support information output unit 112 may suspend the meal assistance sequence regarding the assisted person B if the notification for the assisted person A in the step S608 is notified, and resume the meal assistance sequence for the assisted person B when the caregiver has finished to serve a bite of the meal for the assisted person A. Since the support information output unit 112 determines in step S607 that the meal can be served to the assisted person B, the support information output unit 112 notifies the notification to the caregivers to take a bite of the meal to the assisted person B in the step S608. In this case, since the caregiver is performing the action for the assisted person B, the support information output unit 112 performs processing to suspend the meal assistance sequence of the assisted person A until the action is completed.

Alternatively, the support information output unit 112 may suspend the meal assistance sequence related to the assisted person A until all other assisted persons in charge of the meal assistance by the same caregiver are in the same position if it is determined that the assisted person A is in the same position (Yes in the step S603).

Figure 24A:
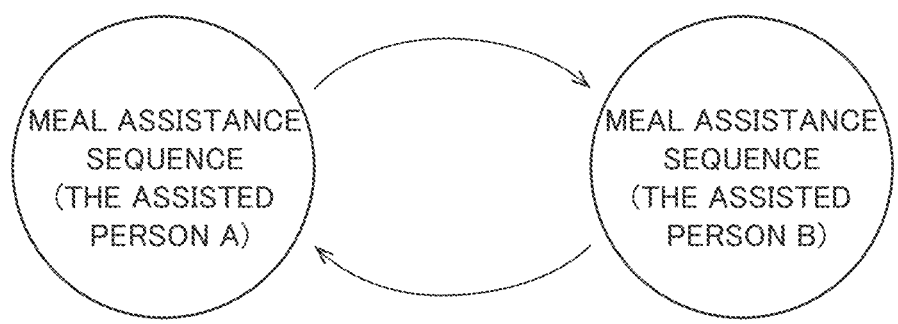
FIG. 24A is a diagram illustrating the transitions between multiple assistance sequences.

FIG. 24A is a state transition diagram illustrating the transition of the assistance sequence for a prescribed caregiver. For example, the support information output unit 112 performs two meal assistance sequences to support the caregiver providing both the meal assistance for the assisted person A and the assisted person B. In this case, the support information output unit 112 performs a state transition based on a prescribed condition. For example, the support information output unit 112 stops the meal assistance sequence with respect to the assisted person A and transitions to a state performing the meal assistance sequence with respect to the assisted person B if it is determined that one assistance unit by the caregivers is completed when performing the meal assistance sequence for the assisted person A.

Alternatively, the support information output unit 112 may determine the priority of the support information to be notified in each assistance sequence. For example, suppose that the support information output unit 112 determines that a notification to record the meal result (the step S610) is executed because the assisted person A had finished eating the meal and notification to serve a bite of the meal (the step S608) is executed since the assisted person A had not finished eating the meal.

The recording of the meal results can be done at any time until cleaning up, whereas the serving a bite of the meal should continue until the eating the meal for the assisted person B is completed. Therefore, in this case, the support information output unit 112 may prioritize the execution of the meal assistance sequence of the assisted person B and suspend the meal assistance sequence of the assisted person A. In this way, it is still possible to achieve appropriate state transitions between multiple assistance sequences targeting multiple assisted persons. It should be noted that the state transition between two or more assistance sequences can be thought of as an interruption by another assistance sequence to an ongoing assistance sequence.

Figure 24B:
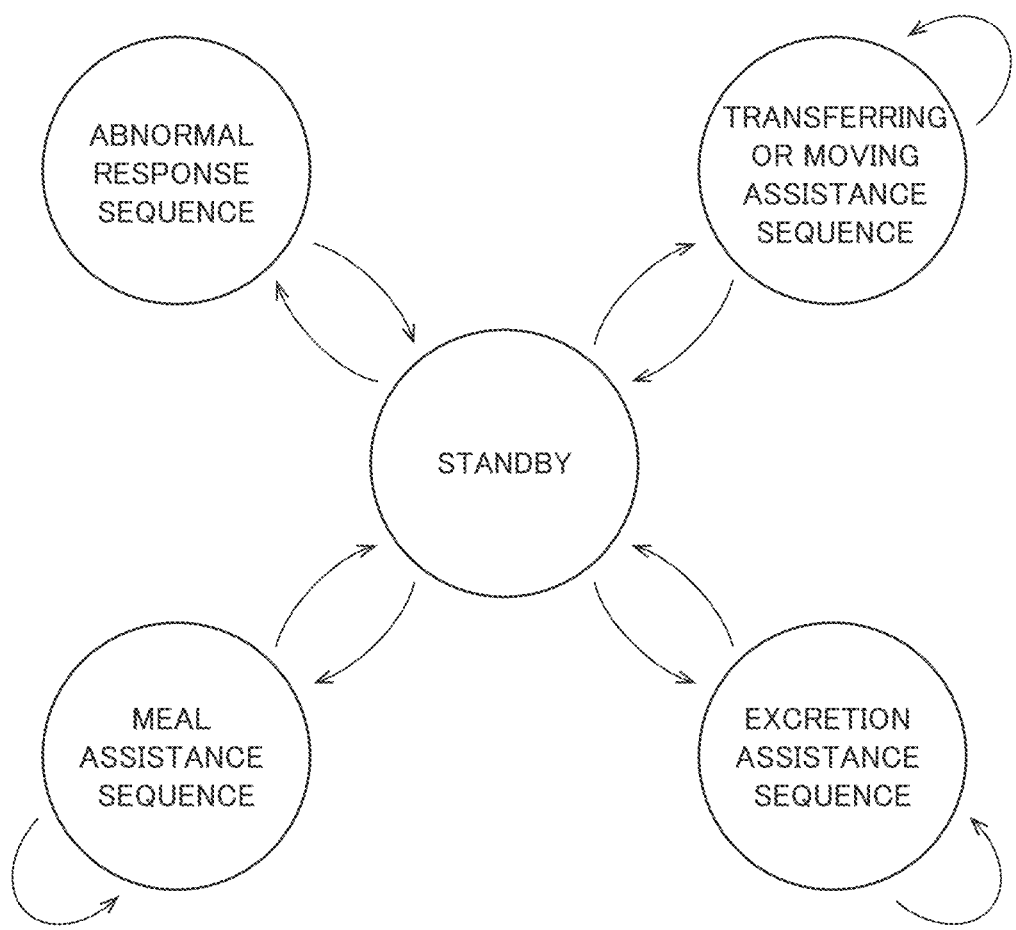
FIG. 24B is a diagram illustrating the transitions between multiple assistance sequences.

In addition, although we have shown an example in which two meal assistance sequences are executed in parallel, the method of this embodiment is not limited to this. FIG. 24B is another diagram illustrating the state transitions between the assistance sequences in this embodiment.

As shown in the FIG. 24B, various sequences such as the meal assistance sequence, the excretion assistance sequence, the transferring or moving assistance sequence, and the abnormal response sequence may be executed in parallel in this embodiment. In this case, the support information output unit 112 may control the transition between each assistance sequence shown in the FIG. 24B. In addition, the FIG. 24B shows an example of a transition from a prescribed type of assistance sequence to another type of assistance sequence via a standby state, but a direct transition may be executed between each assistance sequence. Also, as shown in the FIG. 24A, the meal assistance sequence may include multiple assistance sequences. Similarly, it is possible for other assistance sequences, such as the excretion assistance sequence to include multiple assistance sequences.

For example, suppose that a prescribed caregiver is serving a meal to the assisted person A when the assisted person A is in an abnormal state. The abnormal condition is, for example, choking. In this case, the caregiver will stop the meal assistance to the assisted person A and take an action for the abnormal condition. For example, the support information output unit 112 performs the start determination of the abnormality response sequence in the background in a same way of the steps S501 to S503 in the FIG. 20, and starts the abnormality response sequence when the abnormality of the assisted person A is detected. Although the processing of the steps S505 to S506 in the FIG. 20 may be performed, the processing of the steps S505 to S506 may be omitted in consideration of the fact that the caregiver in charge of the assisted person A is the same as the caregiver in charge of the meal assistance and that there is a possibility of high emergency.

As the result, the abnormality response sequence may be added to the assistance sequence to be performed. Then, the support information output unit 112 suspends the meal assistance sequence currently being performed and starts performing the abnormality response sequence. When the abnormality is resolved by the abnormality response sequence, the support information output unit 112 performs a transition to another assistance sequence such as resuming the suspended meal assistance sequence.

Alternatively, in some cases, when a prescribed caregiver is serving the meal to the assisted person A, the assisted person A may want to go to the restroom. In this case, the excretion assistance sequence is added to the assistance sequence to be performed. In addition, depending on the ADL of the assisted person A and the location of the toilet, a transferring or moving assistance sequence may be required. For example, the support information output unit 112 suspends the meal assistance sequence, firstly performs the transferring or moving assistance sequence to move to the toilet, then performs the excretion assistance sequence, and resumes the suspended meal assistance sequence that after completion.

The factors that the necessary assistance changes include the initiative of the assisted person, the physical condition of the assisted person, the diseases such as dementia, the medications, the environment, the seasons, the external factors, and the difference between the day's care progress and the schedule. For example, the support information output unit 112 may perform a processing to detect these factors and determine the assistance sequence to be the transition destination based on the detected factors and the assistance sequence currently being performed.

Thus, the support information output unit 112 can appropriately deal with the various situations by performing multiple assistance sequences in parallel and by controlling the state transitions between the multiple assistance sequences. For example, as noted above, even if there is a case that one caregiver deal with many assisted person, it is possible to determine the assistance should be performed and the order. Since the burden on the caregiver can be reduced, the risk of incidents such as aspiration and falling of the assisted person can be reduced. In addition, even if other assistances suddenly become necessary during performing the prescribed assistance, it is possible to reduce the burden on the caregiver and the risk to the assisted person, because the caregiver can appropriately support the assistance to be performed at that time.

Adding Data by the Users

In the above explanation, it is assumed that the support information output NN 122 is generated by the learning unit 114. For example, a provider of an information processing device may select the nursing home, etc. for learning in advance and may create the support information output NN 122 using data acquired from the nursing home, etc. When a nursing home utilizing the services provided by the information processor is newly added, for example, the existing support information output NN 122 is commonly used.

However, the method of this embodiment is not limited to this one, and a new training data may be added by the user of the nursing home, etc., and the additional machine learning may be performed using the training data.

For example, the data from each nursing home may be combined and used for machine learning while maintaining that the support information output NN 122 is common among the multiple nursing homes. This case has an advantage of increasing the number of training data because the training data can be collected from multiple nursing homes.

Alternatively, the additional machine learning may be performed for each nursing home. In this case, the support information output NN 122 is updated for each nursing home. That is, it becomes possible to make the support information output NN 122 specific to the target nursing home.

Figure 25A:
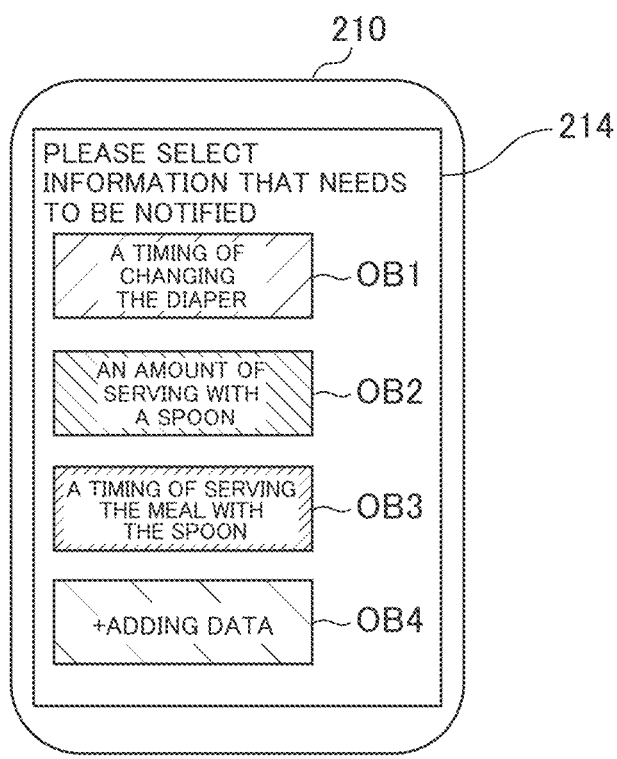
FIG. 25A shows an example of a settings screen.

FIG. 25A is an example of a screen displayed on the display unit 214 of a mobile terminal device 210, for example. In comparison with the FIG. 17, an object OB4 for adding the data is added. When the caregiver selects the object OB4, the screen changes to the screen of the FIG. 25B.

Figure 25B:
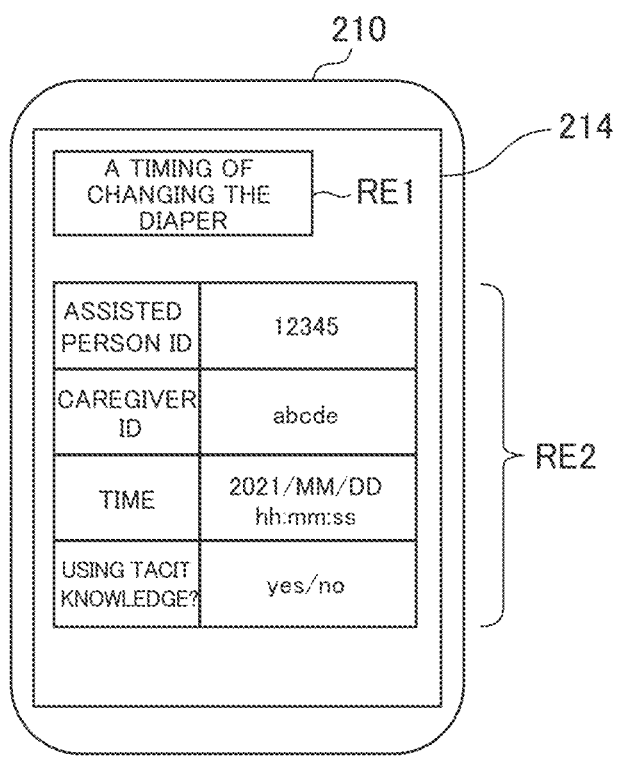
FIG. 25B shows an example of a display screen for adding data.

The FIG. 25B includes an area RE1 showing the names of the support information of the added training data, and an area RE2 which can input the assisted person ID, the caregiver ID and the output data. The assisted person ID is the information to identify the assisted person. The caregiver ID is the information to identify the caregiver. The output data is the information corresponding to the output of the support information output NN 122. Since the FIG. 25B deals with a timing of changing the diaper, an example of using time as output data is shown. However, the format of the output data can be modified in various ways according to the type of the support information, and may be an image, a voice, a number value, a binary data representing authenticity, or other formats.

The example of the FIG. 25B shows that the time of 2021/MM/DD hh:mm:ss as the timing of changing the diaper was appropriate when the caregiver whose caregiver ID is "abcde" performs the excretion assistance for the assisted person whose assisted person ID is "12345". Apart from the caregiver's operation, the input data corresponding to the timing of changing the diaper is acquired in the nursing home. That is, the data set in which the input data is associated with the output data of 2021/MM/DD hh:mm:ss may be a training data of the support information output NN 122 which outputs a timing of changing the diaper.

However, the present embodiment assumes that the tacit knowledge of the skilled assistant is converted into data and that the appropriate assistance is performed regardless of the skill level of the assistant. Therefore, even if the above data set is obtained by the input from a prescribed caregiver, it is not clear whether it is a positive data or a negative data. The positive data represents a data set with appropriate correct data associated with the input data, and the negative data represents a data set with inappropriate correct data associated with the input data.

Therefore, the learning unit 114 may store an association information in which the caregiver ID for example, is associated with the skill level of the caregiver. The level of skill may be manually input by a nursing home administrator, or it may be automatically determined based on years of experience, the qualifications, and the past nursing history. The learning unit 114 sets the data set by the highly skilled caregiver as the positive data and the data set by the less skilled caregiver as the negative data.

Alternatively, even when the assistance is provided by a skilled person, the assistance can be considered as either the case that the assistance is provided according to the defined procedure or the case the assistance is adjusted by one's own instinct. It is highly probable that the tacit knowledge of a skilled person is used when the skilled person takes the actions according to a hunch. Therefore, as shown in the FIG. 25B, the area RE2 of the display screen may be input-able whether or not a hunch was used. The caregiver inputs into the area RE2 whether or not he or she had used a hunch, for example, when determining the timing of changing the diaper. The learning unit 114 uses the data set when the corresponding input is "yes" as the positive data.

Regarding to the learning process after acquiring the training data, a detailed explanation is omitted because it is the same as the example described above using the FIG. 8.

In the example of the FIG. 25B, by updating the support information output NN 122 that outputs the timing of changing the diaper, it becomes possible to output more accurate the timing of changing the diaper. Now, we have explained an example of the timing of changing the diaper, but adding training data is equally possible for other support information.

Custom Support Information

In the above, the FIGS. 43 to 45 are illustrated as the support information that can be output. However, as we can see from the above explanation, there is a wide variety of the support required for the assistance, and it is possible that the support required for the assistance may vary depending on the nursing home or the caregiver. As a result, there may be cases in which the support information of a type not included in the existing support information is needed. Therefore, in this embodiment, the caregiver may be able to add any custom support information.

For example, in the FIG. 25B, the name of the support information displayed in the area RE1 is not fixed and may be freely editable by the caregiver. The caregiver inputs the name of the desired custom support information using text such as "a timing of performing xxxx." "xxxx" is a text that describes a detailed assistance action performed by, for example, a caregiver. In addition, when the caregiver performs the assistance action corresponding to "xxxx," the caregiver ID, the assisted person ID, the output data, whether or not the hunch was used, etc., are input. Thus, as part of the training data of the support information output NN 122 that outputs "a timing of performing xxxx," the output data and the information indicating whether the output data is the positive data or the negative data are obtained.

Figure 25C:
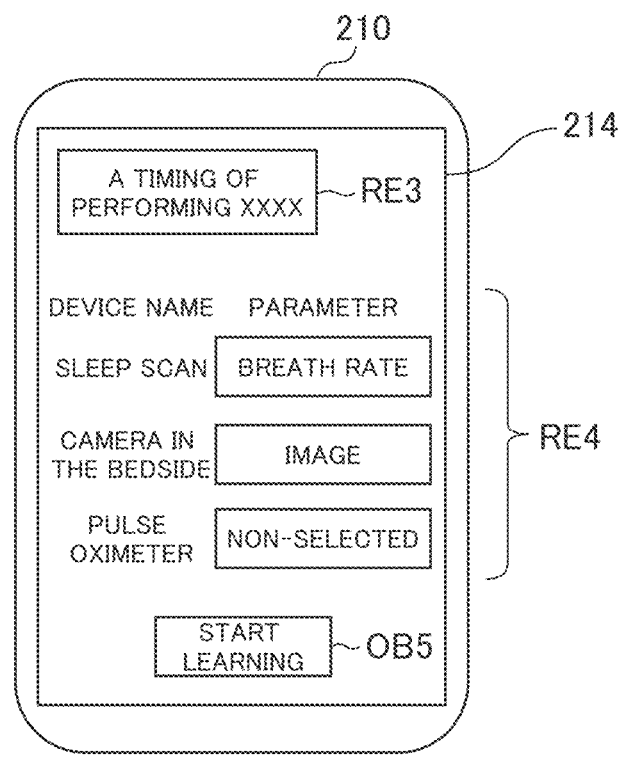
FIG. 25C shows an example of a display screen for determining an input data.

In addition, the information processing device may control to display a screen to identify the input data in the training data on the display unit 214 of the mobile terminal device 210. The FIG. 25C is an example of a display screen for specifying the input data. The screen shown in the FIG. 25C includes an area RE3 for displaying the name of the custom support information and an area RE4 where the name of the device already placed in the target nursing home or the name of the input data acquired by the device can be selected.

For example, a sleep scan is a sensing device 450 shown in the FIG. 2D, which can detect a heart rate, a respiratory rate and an activity. The caregiver selects the data available on the device that he or she wants to use as input data when obtaining the custom support information among the data which can detect by the device. The FIG. 25C shows an example that the caregiver selects to take the breathing rate from the sleep scan, to take the image arranged on the bedside camera, not to take the output of the pulse oximeter as the input data.

By using the screen shown in the FIG. 25C, the name of the custom support information is associated with the input data used to output the custom support information. The association information representing this association is transmitted to the server system 100 and stored in the storage unit 120.

The storage unit 120 of the server system 100 stores the time series of breathing rates data and the time series of the images of the bedside camera. Therefore, the learning unit 114 extracts the respiratory rate and the camera image corresponding to the output data acquired using the FIG. 25B as input data.

For example, the server system 100 keeps the timing of acquiring the output data based on the FIG. 25B, and reads the respiration rate and the camera image for a prescribed period set based on the timing from the storage unit 120. Then, the learning unit 114 performs a learning processing of the support information output NN 122 to output the custom support information based on the training data in which the read input data is associated with the output data.

Also, as shown in the FIG. 25C, the object OB5 for starting the learning operation may be displayed on the display unit 214 of the mobile terminal device 210. When it is detected that the caregiver has selected the object OB5, the learning unit 114 performs the above learning processing. Thus, a new support information output NN 122 to output the custom support information is generated. Since the learning process is the same as the above example, a detailed explanation is omitted. In addition, in the machine learning of the custom support information, it may be sufficient that the training data in which the input data is associated with the output data can be obtained, and the user interface is not limited to those described above.

Figure 26:
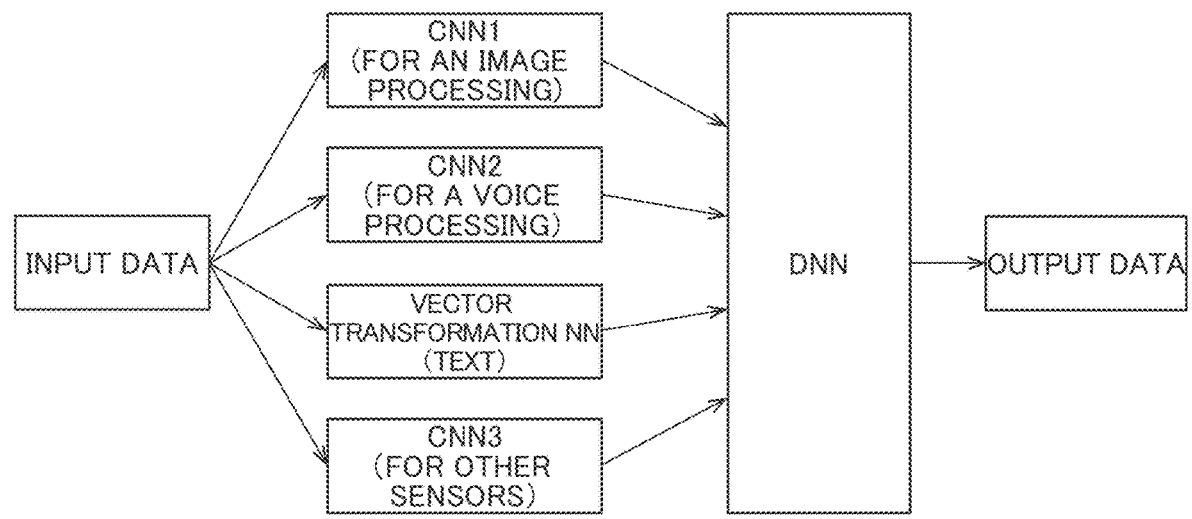
FIG. 26 shows a basic configuration example of a neural network in this embodiment.

The structure of the NN can be modified in various ways. The FIG. 26 shows the structure of the general NN. The NN shown in the FIG. 26 includes a CNN1 which extracts feature quantities using the image data as input, a CNN2 which extracts feature quantities using the voice data as input, a vector transformation NN which extracts feature quantities using text data as input, and CNN3 which extracts feature quantities using other sensor information as input. The NN in the FIG. 26 also includes a DNN (Deep Neural Network) that accepts the outputs from the CNN1, the CNN2, the vector transform NN, and the CNN3 and outputs the custom support information.

The NN shown in the FIG. 26 can accept the image, the voice, the text and other sensor information as the inputs. The input data of the custom support information can have various patterns as shown in, for example, FIG. 25C, but the NN shown in the FIG. 26 can appropriately accept data of any pattern as the input data. If the image data is not selected as input data, the input of CNN1 is treated as 0. The same applies when the voice data, the text data or other sensor information is not selected as input data, and the input of the corresponding NN among the CNN2, the vector conversion NN and the CNN3 becomes 0.

Figure 25D:
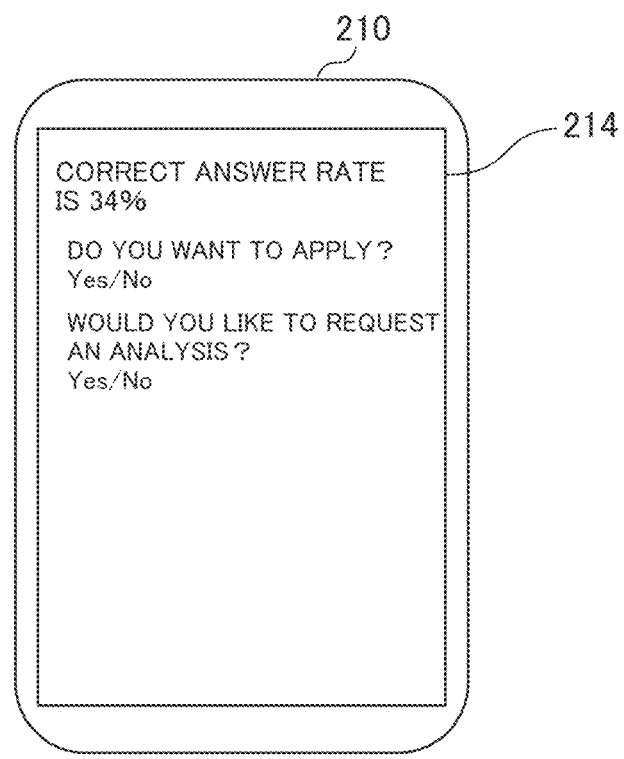
FIG. 25D shows an example of a display screen for presenting learning results.

FIG. 25D shows an example of a screen displayed on the display unit 214 of the mobile terminal device 210 after the completion of the machine learning. The display screen of the FIG. 25D displays the correct answer rate obtained using the validation data, for example, in the learning process. In the example shown in the FIG. 25D, the caregivers can choose whether or not to output the custom support information using this learning result. For example, if the caregiver selects "yes" to the question "Do you want to apply?", the custom support information can be output. For example, similar to the example described above in the FIG. 17, the custom support information can be output by setting "active" about the custom support information "a timing of performing xxxx." On the other hand, if the caregiver selects "no", no custom support information will be output.

It is also possible that caregivers want to use the target custom support information because it is important, although the target custom support information can not be adopted as is due to the low accuracy rate. In this case, it may be possible to request the analysis processing to the manager or the provider of the information processing device. For example, when the caregiver select "yes" for the question, "Would you like to request an analysis?", a changing processing of the support information output NN 122 to output the custom support information is performed on the server system 100 side.

The learning unit 114 of the server system 100 may try to improve the correct answer rate by changing the structure of the NN, for example, when the original correct answer rate is lower than a prescribed threshold. This is because the NN shown in the FIG. 26 has a configuration that considers the versatility as described above, and the accuracy rate may be improved by having a structure that is more specialized for the custom support information. If the original correct answer rate exceeds the prescribed threshold, the learning unit 114 may skip the change processing of the support information output NN 122.

For example, when there are multiple NNs with different structures from each other as the support information output NN 122 for as shown in the FIG. 10, the learning unit 114 may classify the multiple NNs into several classes.

Figure 27:
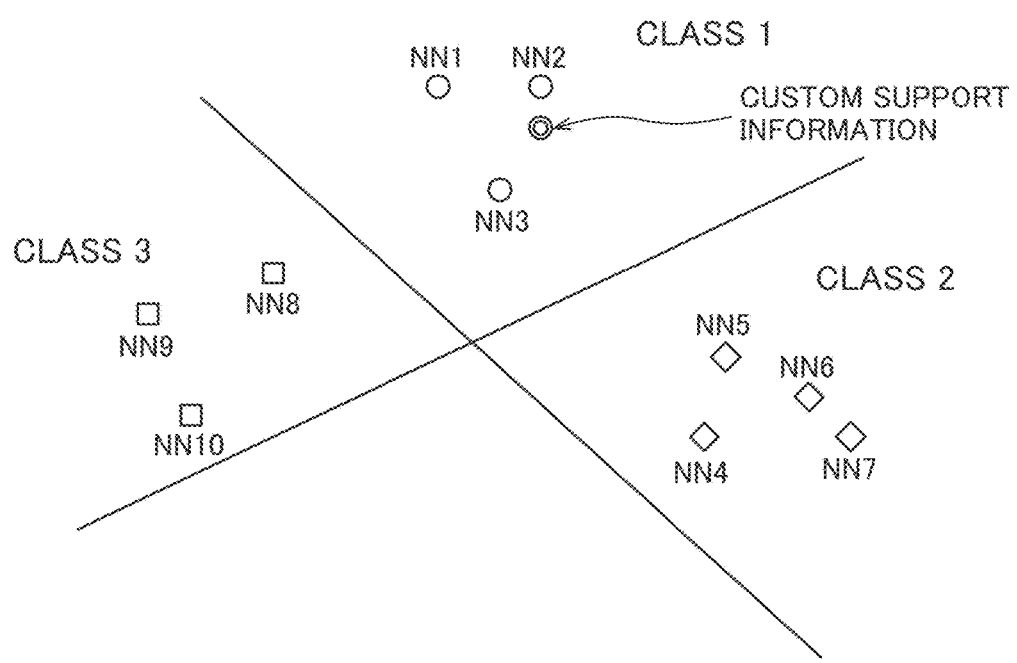
FIG. 27 illustrates a determining process to determine a structure of a neural network by classification.

FIG. 27 is a diagram to explain the classification process of the NN. For example, the learning unit 114 obtains an n-dimensional feature quantity by performing a text mining processing using text representing the name of the support information as the output, and performs a clustering processing based on the n-dimensional feature quantity. For convenience of the explanation, a two-dimensional feature plane is shown in the FIG. 27, but n may be 3 or more. For example, among a plurality of the support information output NN 122, if an NN outputting "a timing of changing the diaper" is targeted, words such as "diaper", "change" and "timing" are extracted, and an n-dimensional feature quantity of the NN outputting "a timing of changing the diaper" is obtained based on the extraction result.

The clustering processing method is not limited to the text mining processing, and the learning unit 114 may cluster multiple NNs by performing an analytical processing such as logistic regression analysis. The learning unit 114 may also assign the clustering results which are manually clustered for the part of the multiple NNs shown in the FIG. 10 and perform the clustering processing for the remaining NNs using the clustering results. In this way, the accuracy of the clustering processing can be improved.

In the example in the FIG. 27, among the multiple NNs stored by the server system 100, the NN1 to NN3 were classified as the class 1, the NN4 to NN7 were classified as the class 2, and the NN8 to NN10 were classified as the class 3. The learning unit 114 determines which class it belongs to by similarly obtaining the n-dimensional feature quantity based on the name of the custom support information. For example, the learning unit 114 extracts words such as "XXXX" and "timing" from the name of custom support information such as "a timing to performing XXXX," and obtains an n-dimensional feature quantity corresponding to the custom support information based on the extraction result. The learning unit 114 determines the structure of the NN used for the learning based on the clustering result of the custom support information.

For example, as shown in the FIG. 27, it is assumed that the custom support information is classified as the class 1. In this case, the learning unit 114 selects any one of the NN1 to NN 3 and generates a NN for the custom support information using the structure of the selected NN and the training data for the custom support information described above. Only the structure of the original NN is used, and all of the weights may be computed anew. Alternatively, a transfer learning may be performed using a part of the original NN's weights as is. For example, the learning unit 114 performs a machine learning using the respective structures of the NN1 to NN 3 and training data for the custom support information, and obtains the correct answer rate of the learned model. Then, the learning unit 114 presents the highest correct answer rate to the caregiver in the same manner as in the FIG. 25D and makes the caregiver input whether or not the learned model is applied. When the caregiver responds "yes", the corresponding support information output NN 122 is stored in the storage unit 120 to enable the output of the custom support information.

When an additional machine learning is performed, it is important that the relationship between the period of the accumulation of the training data, in other words, the period of the acquired data to be analyzed, and the ADL of the assisted person. For example, suppose that an assisted person who was able to take actions independently broke a bone in the falling and he or she need the assistance by a wheelchair. If there is a significant change in ADL, there is a significant difference in the appropriate assistance for the assisted person between before the change and after the change. Therefore, for example, the learning results used the training data before changing ADL may not be useful after changing ADL.

Therefore, although not shown in the FIG. 25C, for example, when starting performing a learning processing, it may be possible to input not only the type of the input data but also the analysis period. The caregiver designates a period of time during which the assisted person's ADL is considered to be comparable to the current one.

In this way, the support information output NN 122, which is the result of the learning processing, can support the appropriate assistance because the content of the learned model corresponds the current ADL of the assisted person. It is also assumed that the server system 100 collects the ADL of the assisted person, for example, as one of the input data. Therefore, when starting performing the learning processing, the learning unit 114 may acquire the time series change of the ADL of the target assisted person and automatically set the analysis period based on the time series change of the ADL.

Although the present embodiment has been described in detail as described above, those skilled in the art will readily understand that many modifications can be made that do not materially deviate from the novel matters and effects of the present embodiment. Therefore, all such variations shall be included in the scope of this disclosure. For example, a term appearing at least once in a description or drawing with a different term that is more broadly or synonymously may be replaced by that different term anywhere in the description or drawing. All combinations of this embodiment and variations are also included in the scope of this disclosure. Moreover, the configuration and operation of the information processing system, the server system, the mobile terminal device, etc., are not limited to those described in this embodiment, and various modifications can be performed.

What is claimed is:

1. An information processing device comprising:
   a controller configured to determine whether a behavior of an assisted person is an abnormal behavior of a dementia factor based on (1) an information on a dementia level of the assisted person and (2) at least one of an environmental information, an excretion information, and a sleep information of the assisted person, and
   a support information output unit configured to output a support information to support an assistance of the assisted person by a caregiver based on the determination result of the controller and a sensor information that is a sensing result about the assisted person or the caregiver assisting the assisted person, the support information including information how the caregiver should take an action to the assisted person in a care situation, wherein
   the support information output unit outputs the support in formation to care device,
   the information processing device controls the care device to provide assistance to the assisted person based on the outputted support information, and
   the control of the care device comprises adjusting a position of the care device based on a sensing result of the sensor information.

2. The information processing device according to the claim 1, wherein
   the support information includes an information to support at least one of a meal assistance to assist the assisted person to eat a meal, an excretion assistance to assist the assisted person to excrete, and a transferring or moving assistance to assist the assisted person to transfer or move.

3. The information processing device according to the claim 2, wherein
the support information output unit is configured to output an information indicating the amount of the meal to be served per one bite and an information indicating a timing of serving the meal per one bite in the meal assistance as the support information, and is configured to change at least one of the amount of serving and the timing of serving in comparison with a case the behavior is determined not to be the abnormal behavior of the dementia factor if the behavior is determined to be the abnormal behavior of the dementia factor.

4. The information processing device according to claim 3, wherein
the support information output unit is configured to increase a type of the sensor information in comparison with a case the behavior is determined not to be the abnormal behavior of the dementia factor if the behavior is determined to be the abnormal behavior of the dementia factor.

5. The information processing device according to the claim 2, wherein
the support information output unit is configured to output an information specifying a timing to start performing the excretion assistance as the support information, and is configured to change the timing to start performing the excretion assistance in comparison with a case the behavior is determined not to be the abnormal behavior of the dementia factor if the behavior is determined to be the abnormal behavior of the dementia factor.

6. The information processing device according to claim 5, wherein
the support information output unit is configured to increase a type of the sensor information in comparison with a case the behavior is determined not to be the abnormal behavior of the dementia factor if the behavior is determined to be the abnormal behavior of the dementia factor.

7. The information processing device according to claim 2, wherein
the support information output unit is configured to increase a type of the sensor information in comparison with a case the behavior is determined not to be the abnormal behavior of the dementia factor if the behavior is determined to be the abnormal behavior of the dementia factor.

8. The information processing device according to claim 1, wherein
the support information output unit is configured to increase a type of the sensor information in comparison with a case the behavior is determined not to be the abnormal behavior of the dementia factor if the behavior is determined to be the abnormal behavior of the dementia factor.

9. The information processing device according to the claim 8, wherein
the support information output unit is configured to determine whether or not to add a new sensor based on an information specifying one or more used sensors and a sensor information to be added when the behavior is determined to be the abnormal behavior of the dementia factor.

10. The information processing device according to claim 1, wherein the support information includes at least one of a stat timing the caregiver should take the action of the assistance, a movement and vocalization during the action of the assistance.

11. The information processing device according to claim 1, wherein the controller is configured to determine whether the assisted person and the caregiver have moved to a position where the assisted person will eat, then get a minimum amount of the meal the assisted person should eat, and determine a timing of serving a meal with a tableware and the amount served with the tableware.

12. The information processing device according to claim 1, wherein the controller is configured to determine whether the caregiver has moved to a position to assist excretion, then determine whether the movement of the caregiver in removing the diaper is appropriate.

13. The information processing device according to claim 1, wherein the controller is configured to determine whether a lift is necessary for the transferring or moving assistance of the assisted person, then determine whether the usage of the caregiver's body in transferring by manual is appropriate.

14. The information processing device according to claim 13, wherein the controller is configured to instruct the caregiver to lock the wheelchair before determining whether the usage of the caregiver's body in transferring by manual is appropriate.

15. An information processing method comprising:
a factor determining step to determine whether a behavior of an assisted person is an abnormal behavior of a dementia factor based on (1) an information on a dementia level of the assisted person and (2) at least one of an environmental information, an excretion information, and a sleep information of the assisted person,
an outputting step to output a support information to support an assistance of the assisted person by a caregiver and a care device, based on the determination result of the factor determining step and a sensor information that is a sensing result about the assisted person or the caregiver assisting the assisted person, the support information including how the caregiver should take an action to the assisted person in a care situation, and
an assistance step to control the care device to provide assistance to the assisted person based on the outputted support information, wherein
the control of the care device comprises adjusting a position of the care device based on a sensing result of the sensor information.

* * * * *